(12) United States Patent
Brooks

(10) Patent No.: US 7,349,556 B2
(45) Date of Patent: Mar. 25, 2008

(54) GENERATION AND DETECTION OF INDUCED ACOUSTIC ENERGY USING ELECTRIC OR MAGNETIC ENERGY

(75) Inventor: Juliana H. J. Brooks, Columbus, OH (US)

(73) Assignee: GR Intellectual Reserve, LLC, Havre de Grace, MD (US)

( * ) Notice: Subject to any disclaimer, the term of this patent is extended or adjusted under 35 U.S.C. 154(b) by 0 days.

(21) Appl. No.: 10/152,187

(22) Filed: May 20, 2002

(65) Prior Publication Data

US 2003/0133596 A1 Jul. 17, 2003

Related U.S. Application Data

(62) Division of application No. 09/151,581, filed on Sep. 11, 1998, now Pat. No. 6,507,662.

(51) Int. Cl.
*G06K 9/00* (2006.01)
(52) U.S. Cl. .................................................... 382/115
(58) Field of Classification Search ............... 382/115, 382/118, 128; 902/3–6; 235/379, 380, 381, 235/382; 73/579, 585, 587; 600/559; 128/746, 128/920, 630, 647, 660.01; 340/5.53, 5.83
See application file for complete search history.

(56) References Cited

U.S. PATENT DOCUMENTS

| 4,385,634 | A | | 5/1983 | Bowen |
| 5,868,682 | A | * | 2/1999 | Combs et al. .............. 600/559 |
| 6,460,413 | B1 | | 10/2002 | Diebold |
| 6,645,144 | B1 | | 11/2003 | Wen et al. |

OTHER PUBLICATIONS

Digital image processing, by Gregory Baxes (p. 218-219) 1994.*
H. Wen and R.S. Balaban, "The Potential for Hall Effect Breast Imaging", *Breast Disease* 10(3,4) IOS Press (1998) pp. 191-195.
H. Wen and R.S. Balaban, "Ultrasonic imaging of the electroacoustic effect in macromolecular gels", *Ultrasonic imaging* Oct. 1998; 20(4): pp. 288-297.
H. Wen, J. Shah and R. Balaban, "Hall Effect Imaging", *IEEE Transactions on Biomedical Engineering*, 45(1) Jan. 1998; pp. 119-124.

* cited by examiner

*Primary Examiner*—Vikkram Bali
(74) *Attorney, Agent, or Firm*—Mark G. Mortenson

(57) ABSTRACT

A method and apparatus for detecting electric and/or magnetic properties of an individual living organism injects electric and/or magnetic energy into the organism and detects acoustic energy which represents the electric and/or magnetic properties of the organism.

20 Claims, 50 Drawing Sheets

DETECTOR CAN BE A PHASE SENSITIVE DETECTOR

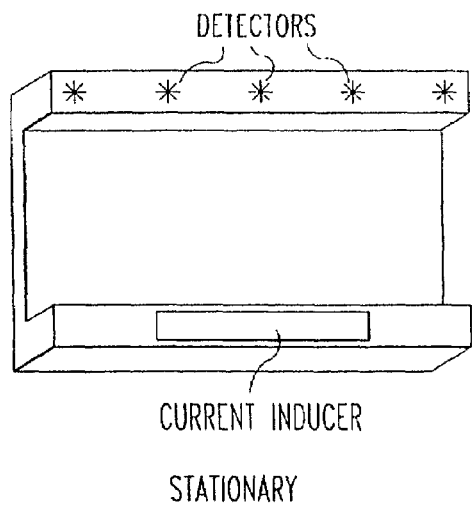
FIG.17a STATIONARY HAND
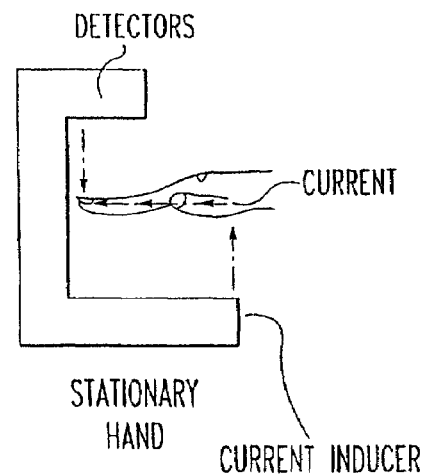
FIG.17b STATIONARY HAND
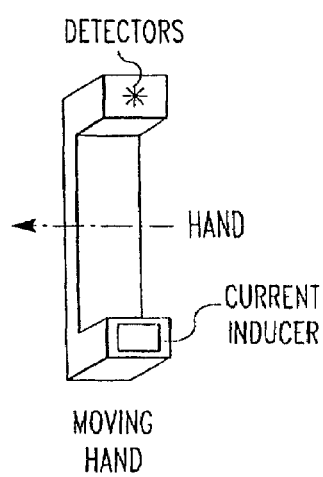
FIG.18a MOVING HAND
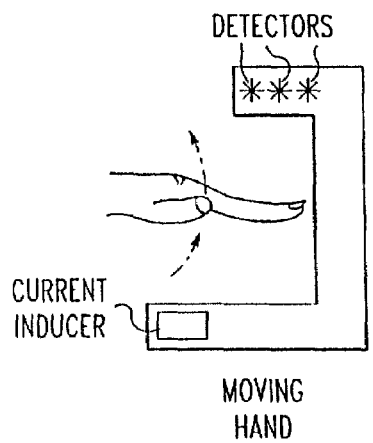
FIG.18b MOVING HAND U₁ = 78L05ACLP    POSITIVE 5 VOLT REGULATOR
U₂ = 79L05CLP     NEGATIVE 5 VOLT REGULATOR
S₁ = DPST

POWER SUPPLY REGULATORS $U_3$ = LT1058CN
HANDPIECE AMPLIFIER 1 THROUGH 4

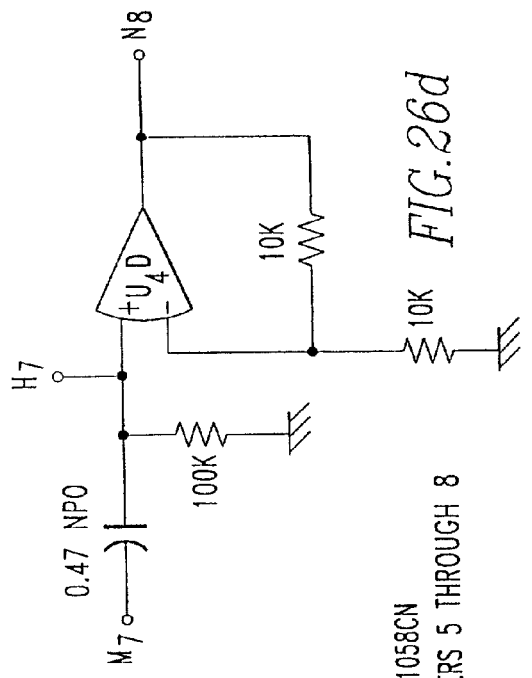
FIG.26c
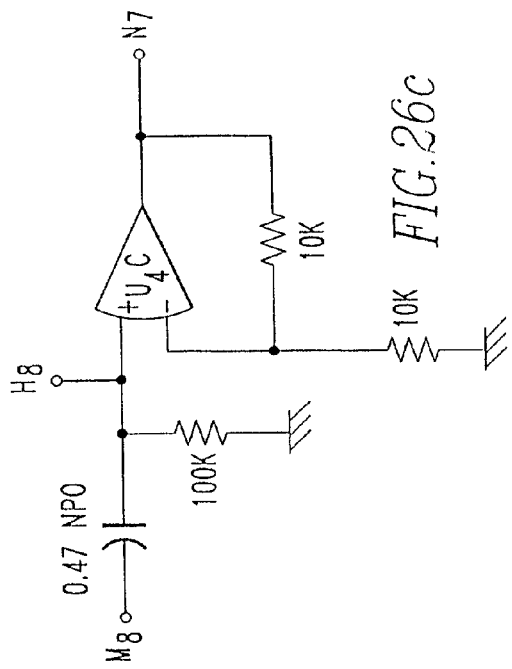
FIG.26d
$U_4$ = LT1058CN
HANDPIECE AMPLIFIERS 5 THROUGH 8
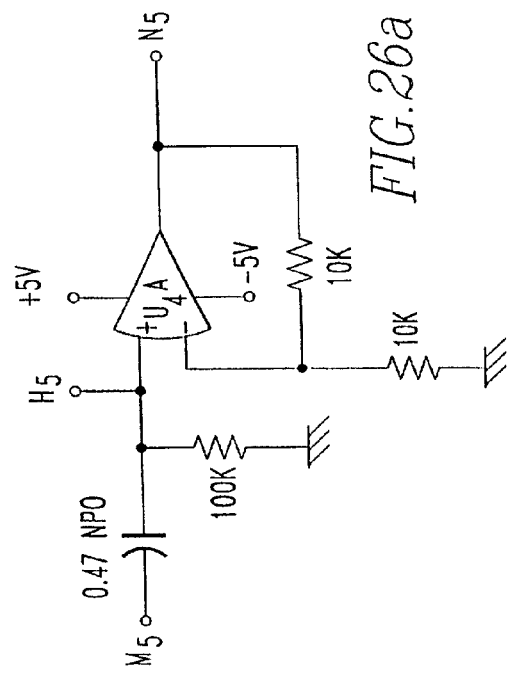
FIG.26a
FIG.26b

OUTPUT MUX LOAD RESISTORS

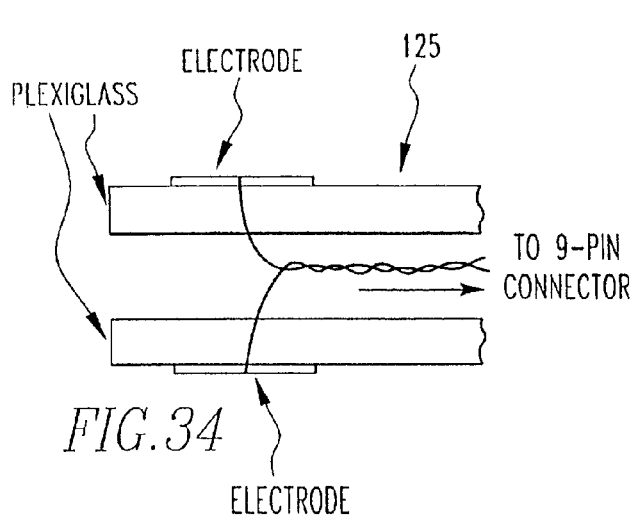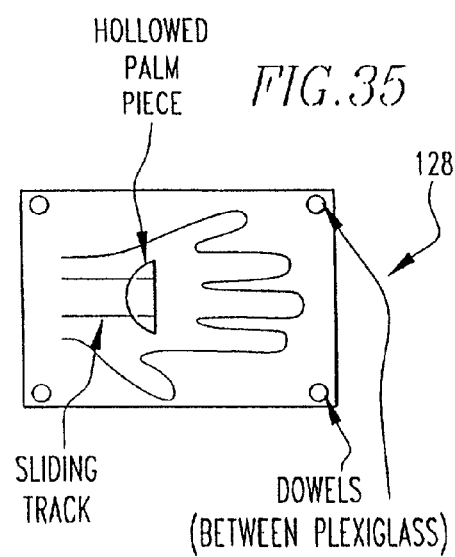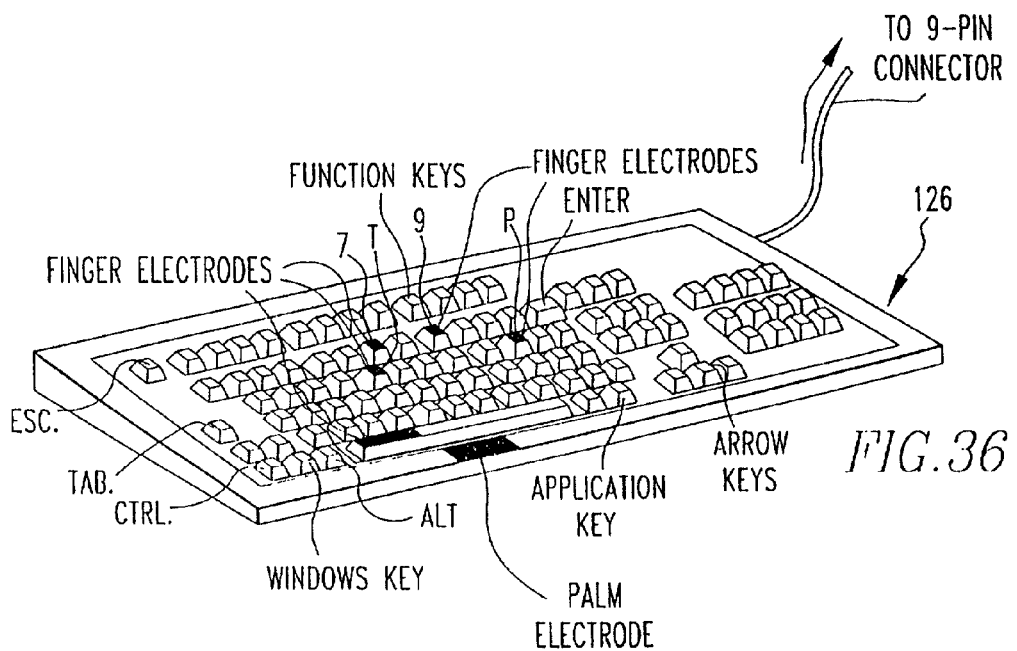

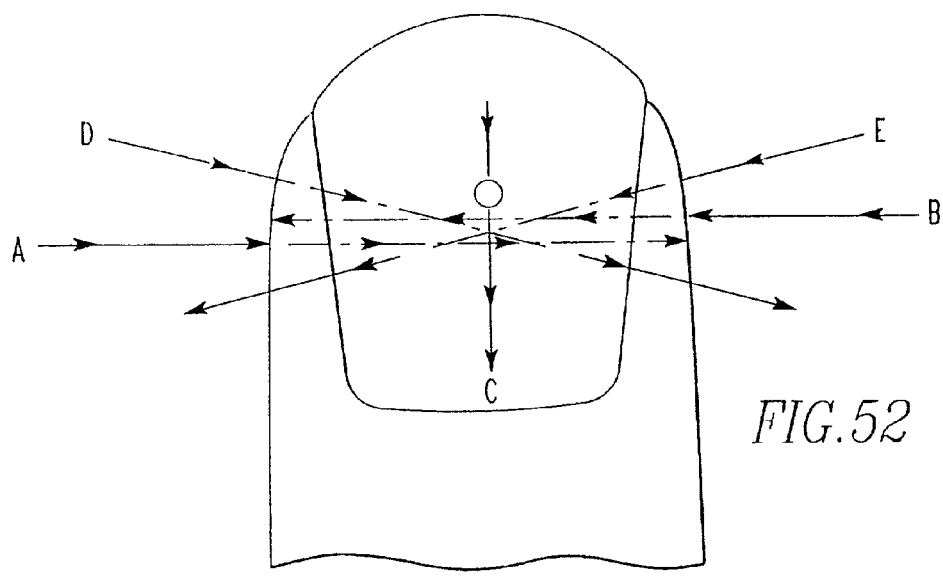
FIG.52
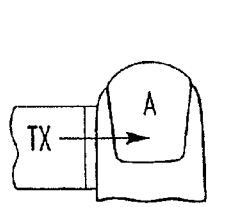 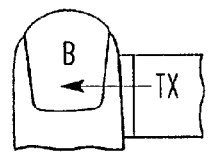 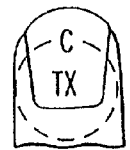 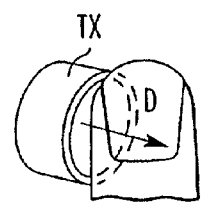
FIG.52a  FIG.52b  FIG.52c  FIG.52d
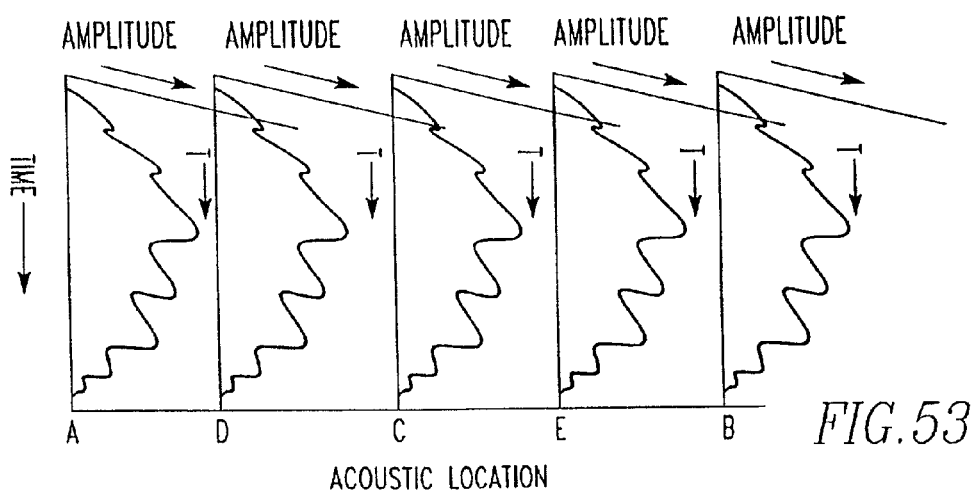
FIG.53

1. NON-CONDUCTIVE RIM
2. CONDUCTIVE ELECTRODE
3. NON-CONDUCTIVE DIVIDER
4. CONNECTOR TO ANALYZER
5. CONNECTOR TO GENERATOR

GENERATION AND DETECTION OF INDUCED ACOUSTIC ENERGY USING ELECTRIC OR MAGNETIC ENERGY

CROSS-REFERENCE TO RELATED APPLICATIONS

This application is a division of U.S. patent application Ser. No. 09/151,581, filed Sep. 11, 1998 now U.S. Pat. No. 6,507,662.

Patent Application PCT/US98/24766, published as WO 99/27489, titled "Method and System for Biometric Recognition Using Unique Internal Distinguishing Characteristics", by Juliana H. J. Brooks, is incorporated by reference herein.

Patent Application PCT/US99/20776, published as WO 00/15097, titled "Methods For Using Resonant Acoustic Energy To Detect or Effect Structures", by Juliana H. J. Brooks, is incorporated by reference herein.

FIELD OF THE INVENTION

The present invention relates generally to the detection of electric and/or magnetic properties in an individual living organism. More specifically, the present invention relates to biometric recognition wherein electric and/or magnetic properties of an organism are used to recognize the organism.

BACKGROUND OF INVENTION

Security methods based on memory data encoded into magnetic cards such as personal identification numbers or passwords are widely used in today's business, industrial, and governmental communities. With the increase in electronic transactions and verification there has also been an increase in lost or stolen cards, and forgotten, shared, or observed identification numbers or passwords. Because the magnetic cards offer little security against fraud or theft there has been a movement towards developing more secure methods of automated recognition based on unique, externally detectable, personal physical anatomic characteristics such as fingerprints, iris pigment pattern and retina prints, or external behavior characteristics; for example, writing style and voice patterns. Known as biometrics, such techniques are effective in increasing the reliability of recognition systems by identifying a person by characteristics that are unique to that individual. Some representative techniques include fingerprint recognition focusing on external personal skin patterns, hand geometry concentrating on personal hand shape and dimensions, retina scanning defining a person's unique blood vessel arrangement in the retina of the eye, voice verification distinguishing an individual's distinct sound waves, and signature verification.

Biometric applications may include but are not limited to, for instance physical access to restricted areas or applications; and access to computer systems containing sensitive information used by the military services, intelligence agencies, and other security-critical Federal organizations. Also, there are law enforcement applications which include home incarceration, parole programs, and physical access into jails or prisons. Also, government sponsored entitlement programs that rely on the Automated Fingerprint Identification System(AFIS) for access are important to deter fraud in social service programs by reducing duplicate benefits or even continued benefits after a recipient's demise.

Biometric recognition can be used in "identification mode", where the biometric system identifies a person from the entire enrolled population by searching a database for a match. A system can also be used in "verification mode", where the biometric system authenticates a person's claimed identity from his/her previously enrolled pattern of biometric data. In many biometric applications there is little margin for any inaccuracy n either the identification mode or the verification mode.

Current commercially available biometric methods and systems are limited because they use only externally visible distinguishing characteristics for identification; for example, fingerprints, iris patterns, hand geometry and blood vessel patterns. To date, the most widely used method is fingerprinting but there are several problems which have been encountered including false negative identifications due to dirt, moisture and grease on the print being scanned. Additionally, some individuals have insufficient detail of the ridge pattern on their prong due to trauma or a wearing down of the ridge structure. More important, some individuals are reluctant to have their fingerprint patterns memorialized because of the ever increasing accessibility to personal information.

Other techniques, currently in use are iris pigment patterns and retina scanning. These methods are being introduced in many bank systems, but not without controversy. There are health concerns that subjecting eyes to electromagnetic radiation may be harmful and could present unidentified risks.

Another limitation of current biometric systems, is the relative ease with which external physical features can be photographed, copied or lifted. This easy copying of external characteristics lends itself quite readily to unauthorized duplication of fingerprints, eye scans, and other biometric patterns. With the advancement of cameras, videos, lasers and synthetic polymers there is technology available to reproduce a human body part with the requisite unique physical patterns and traits of a particular individual. In high level security systems, where presentation of a unique skin or body pattern needs to be verified for entry, a counterfeit model could be produced, thereby allowing unauthorized entry into a secured facility by an imposter. As these capabilities evolve and expand there is a greater need to verify whether the body part offered for identification purposes is a counterfeit reproduction or the severed or lifeless body part of an authorized individual.

U.S. Pat. No. 5,719,950 (Osten), incorporated by reference herein, suggests that verifying an exterior specific characteristic of an individual such as fingerprint in correlation with a non-specific characteristic such as oxygen level in the blood can determine if the person seeking authentication is actually present. This method may be effective but still relies on exterior characteristics for verification of the individual. Also, the instrumentation is complicated having dual operations which introduce more variables to be checked before identity is verified.

Current biometric systems are also limited in size. For example, a fingerprint scanner must be at least as big as the fingerprint it is scanning. Other limitations include the lack of moldability and flexibility of some systems which prevents incorporation into flexible and moving objects. Finally, the complex scanning systems in current biometric methods are expensive and this high cost prevents the widespread use of these systems in all manner of keyless entry applications.

Accordingly, there is a need for more compact, moldable, flexible, economical and reliable automated biometric recognition methods and systems which use non-visible physical characteristics which are not easily copied, photographed, or duplicated. This would eliminate concerns regarding fingerprints that are unidentifiable due to dirt, grease, moisture or external surface deterioration; potential risks involved in eye scanning; costly instrumentation that depends on external characteristics, and the possibility of deceiving a system with an artificial reproduction of a unique external characteristic used for identification.

SUMMARY OF INVENTION

The present invention pertains to an apparatus for recognition of an individual living organism's identity. The apparatus comprises a sensing mechanism for sensing electric and/or magnetic properties of the organism. The apparatus comprises a mechanism for recognizing the organism. The recognizing mechanism is in communication with the sensing mechanism.

The present invention pertains to a method for recognition of an individual living organism's identity. The method comprises the steps of sensing electric and/or magnetic properties of the organism. Then there is the step of recognizing the organism from the property.

The present invention pertains to an apparatus for recognition of an individual living organism's identity. The apparatus comprises a sensing mechanism having a contact area of less than 2.0 centimeters squared to identify an attribute of the organism. The sensing mechanism produces a signal corresponding to the attribute. The apparatus comprises a mechanism for recognizing the organism from the attribute. The sensing mechanism, is in communication with the recognizing mechanism so the recognizing mechanism receives the signal from the sensing mechanism.

The present invention pertains to an apparatus for recognition of an individual living organism's identity. The apparatus comprises a sensing mechanism having a thickness of less than 0.2 centimeters to identify an attribute of the organism. The sensing mechanism produces a signal corresponding to the attribute. The apparatus comprises a mechanism for recognizing the organism from the attribute. The sensing mechanism is in communication with the recognizing mechanism so the recognizing mechanism receives t signal from the sensing mechanism.

The present invention pertains to an apparatus for recognition of an individual living organism's identity. The apparatus comprises a sensing mechanism for sensing an attribute of the organism. The sensing mechanism produces a signal corresponding to the attribute. The apparatus comprises a mechanism for recognizing the organism from the attribute with an accuracy of greater than one in a billion.

The present invention pertains to an apparatus for recognition of an individual living organism's identity. The apparatus comprises a sensing mechanism which is moldable into a shape having a non-flat surface. The sensing mechanism senses an attribute of the organism and produces a signal corresponding to the attribute. The apparatus comprises a mechanism for recognizing the organism from the attribute. The recognizing mechanism is in communication with the sensing mechanism. In the preferred embodiment, the electrodes can be concave, flat, convex, or a combination thereof, lending them to molding into numerous devices. The electrode simply needs to contact the skin of the subject individual.

Characteristics of an organism can be detected by its electrical/magnetic properties, and a individual organism has unique electrical/magnetic properties.
  I. The properties can be measured using any mechanism which measures the properties.
    A. The properties can be measured using any mechanism which uses a DC, AC, electric field, magnetic field, and/or EM field.
    B. The properties can be measured using contact and/or non-contact methods.
    C. The properties can be measured by positioning the organism in relation to the applied energy:
      1. as part of an energy flow
      2. interrupting an energy flow
      3. responding to an energy field by generating its own energy flow
    The properties can be measured using induced currents.
    D. The properties can be measured for a single body segment or for multiple segments. Multiple segments can be compared with each other, i.e., a measured segment from the left hand can be compared to a measured segment on the right hand.
    E. The properties can be measured using one or more frequencies.
    F. The properties can be measured using one or more waveform shapes.
    G. The properties can be measured generating 3 or more dimensional matrices.
    H. The properties can be measured using unique sensors.
      1. Size
      2. Flexibility
      3. Moldability
    I. The properties can be measured to one in one billion accuracy or greater.
  II. An individual organism can be recognized by its electrical/magnetic properties. Any of the mechanisms described in I. can be used for this. Altough the absolute measurements will vary slightly from day to day, the relative ratios of the measurements will remain constant enough to derive a biometric pattern.
  III. Diagnostic characteristics of an organism can we detected by its electrical/magnetic properties. Positioning the organism in relation to the applied energy as part of an energy flow, and interrupting an energy flow are described in the prior art. An organism responding to an energy field by generating its own energy flow, such as an induced current is not. Induced currents can be used to measure the electrical/magnetic properties of an organism to determine diagnostic characteristics such as:
    A. Presence or absence of bone trauma
    B. Presence or absence of tumors
    C. Presence or absence of toxins
    D. Levels of metabolites The present invention pertains to an apparatus for identifying electric and/or magnetic properties of an individual living organism. The apparatus comprises a sensing mechanism for sensing the electric and/or magnetic properties. The apparatus comprises a mechanism for forming matrices corresponding to the organism having at least four-dimensions.

The present invention pertains to a method for sensing an induced current in an individual living organism. The method comprises the steps of inducing current in the organism. Then there is the step of detecting the current induced in the organism.

The present invention pertains to an apparatus for sensing an induced current in an individual living organism. The apparatus comprises a mechanism for inducing current in the organism. The apparatus comprises a mechanism for detecting the current induced in the organism.

The present invention pertains to an apparatus for diagnosing a bone. The apparatus comprises a mechanism for inducing a current in the bone. The apparatus comprises a mechanism for detecting a fracture or break in the bone.

The present invention pertains to a method for diagnosing a bone. The method comprises he steps of inducing a current in the bone. Then there is the step of detecting the induced current in the bone. Next there is the step of detecting a fracture or break in the bone.

The present invention pertains to an apparatus for sensing the electric and/or magnetic properties of an individual living organism. The apparatus comprises a mechanism for transmitting electric and/or magnetic energy into the organism. The apparatus comprises a mechanism for receiving the electric and/or magnetic energy after it has passed through the organism.

The present invention pertains to a method for using a computer. The method comprises the steps of sensing a non-visible attribute of an individual. Then there is the step of recognizing the individual. Next there is the step of accessing the computer by the individual.

The present invention pertains to a method for secure communication between an individual at a first location and a second location. The method comprises the steps of sensing a non-visible attribute of an individual. Then there is the step of recognizing the individual. Next there is the step of allowing the individual to communicate with the second location.

BRIEF DESCRIPTION OF THE DRAWINGS

In order that the invention may readily be carried into practice, one embodiment will now be described in detail, by way of non-limiting example only, with reference to the accompanying drawings in which:

FIGS. 17a and 17b are schematic representations of an apparatus for the measurement of induced current in regard to a stationary hand.

FIGS. 18a and 18b are schematic representations of an apparatus for the measurement of induced current in regard to a moving hand.

FIGS. 24, 25a-25d, 26a-d, 27, 28, 29, 30, 31, 32 and 33 are circuit diagrams for an apparatus for sensing electric or magnetic properties of a hand piece or mouse or keyboard.

FIG. 34 is a schematic representation of a side view of a hand unit.

FIG. 35 is a schematic representation of an overhead view of a hand unit.

FIG. 36 is a schematic representation of a keyboard having electrodes.

FIGS. 52, 52a, 52b, 52c and 52d are schematic representations of acoustic energy at a single frequency passing through the side, center and other side of the thumb by varying the location of the thumb relative to the acoustic energy.

FIG. 53 is a three-dimensional plot regarding FIG. 52.

Finger 57 is a six-dimensional plot with sine, ramped and square wave forms at three different frequencies from electrode to electrode for each finger.

Figure 58:
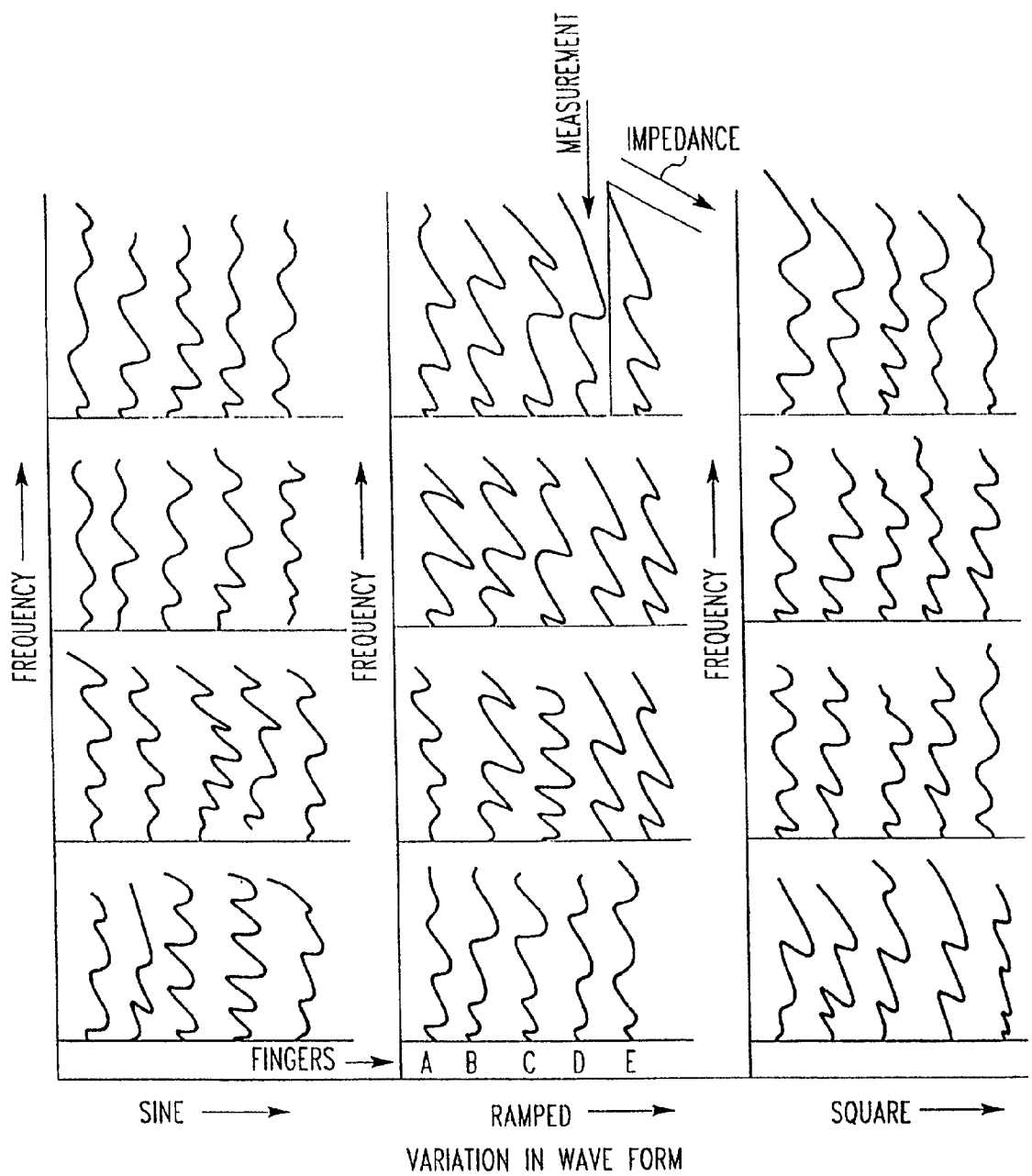

FIG. 58 is a five-dimensional plot with sine, square and ramped waveforms at four different frequencies from the palm to each finger-tip.

Figure 59:
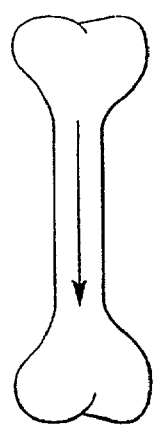

FIG. 59 is a picture of a bone with an arrow representing normal current in a bone.

Figure 60:
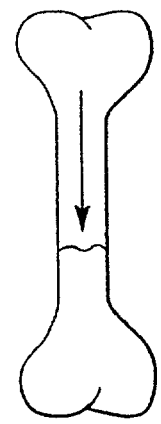

FIG. 60 is a picture of a bone having a fracture or break with current interrupted due to the fracture or break.

Figure 61:
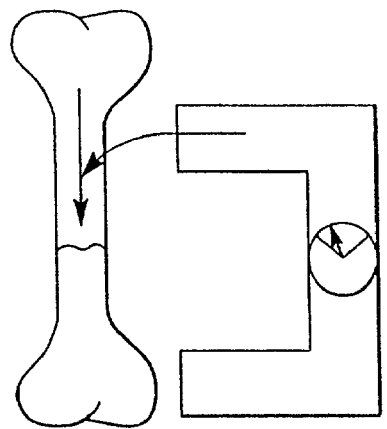

FIG. 61 is a schematic representation of a galvanometer at 0 current reading relative to a bone having a fracture or break where the current has been induced by an apparatus which induces current in a bone.

Figure 62:
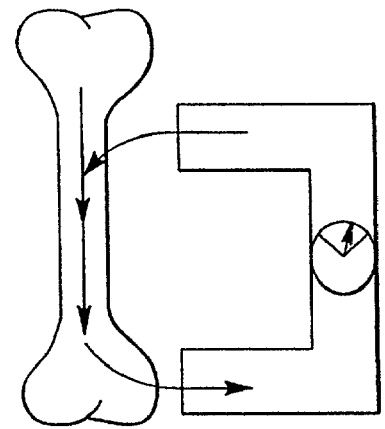

FIG. 62 is a schematic representation of a galvanometer showing normal current in a healthy bone where the current has been induced by an apparatus which induces current in a bone.

Figure 63:
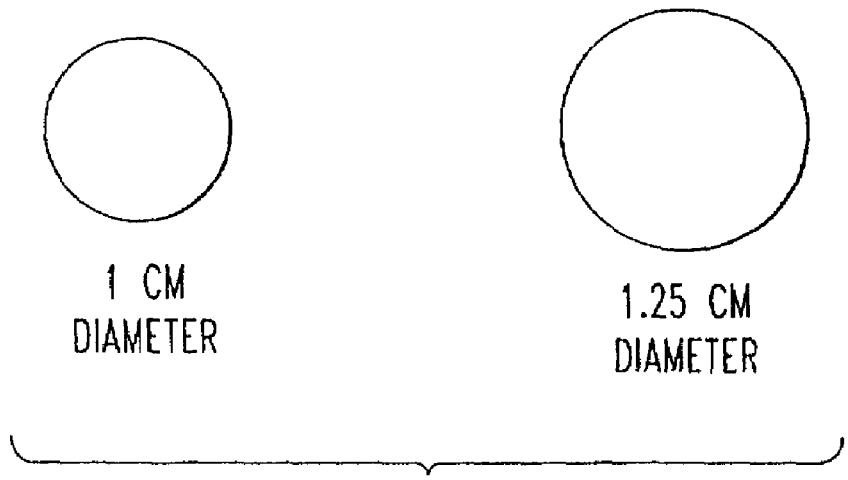

FIG. 63 is a drawing, actual size, of a 1 cm and 1.25 cm diameter electrode.

Figure 64:
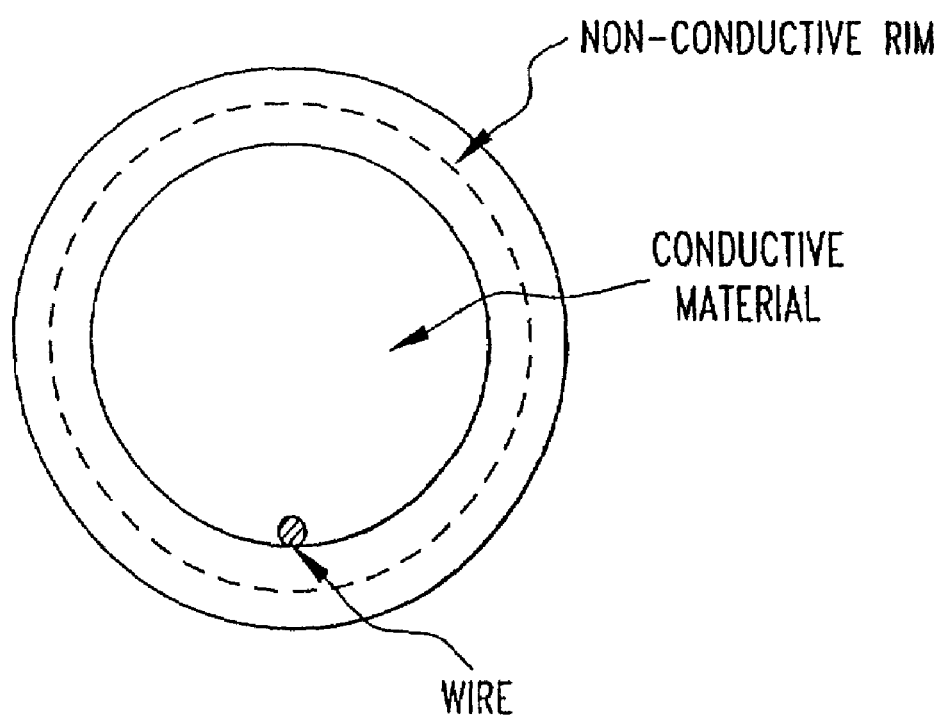

FIG. 64 is a schematic representation of a cross-sectional enlarged view of an electrode.

Figure 65:
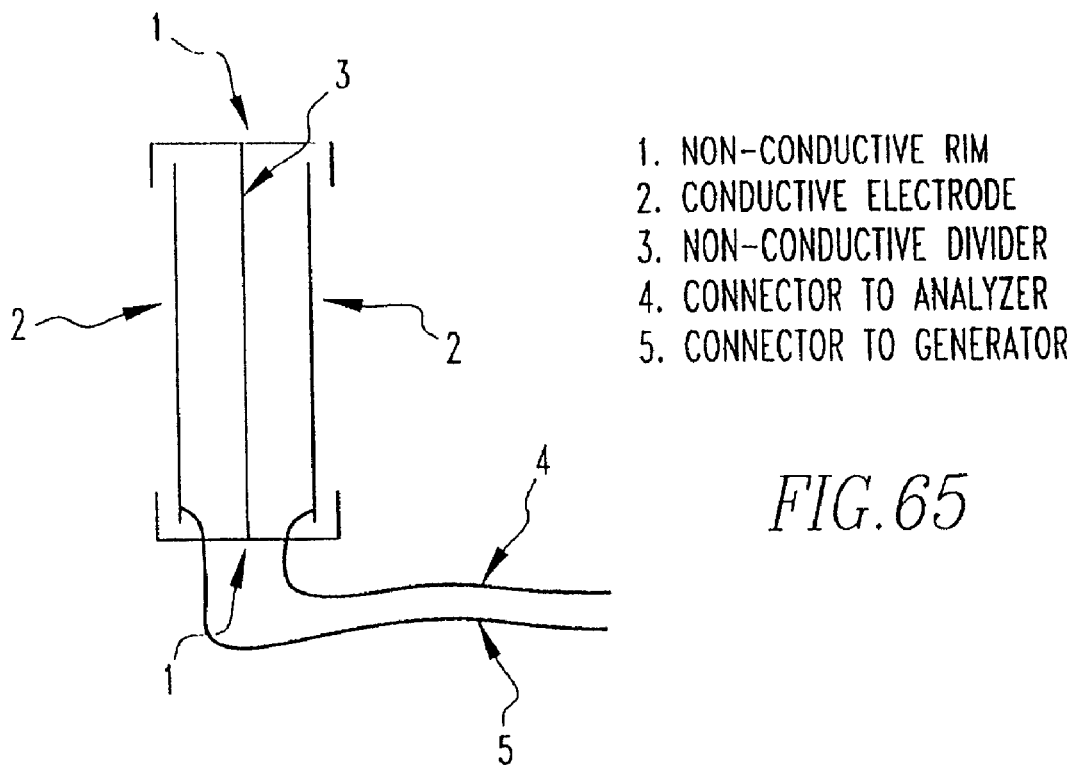

FIG. 65 is a side view of an electrode.

Figure 66:
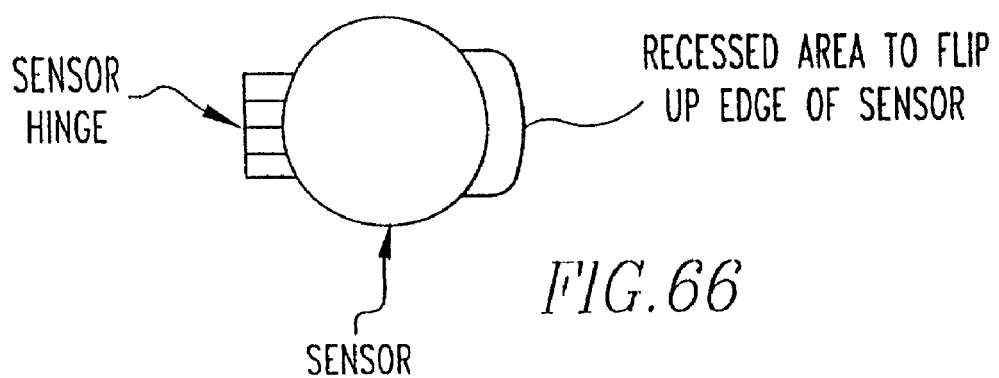

FIG. 66 shows a flip-up sensor.

Figure 67:
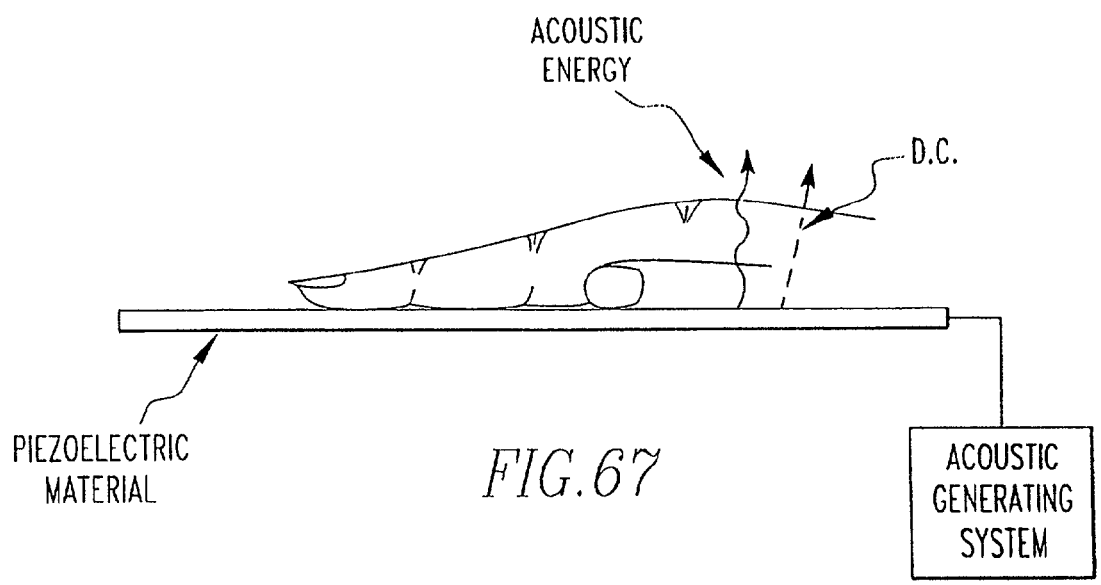

FIG. 67 shows an acoustic mechanism for generation of direct current.

Figure 68:
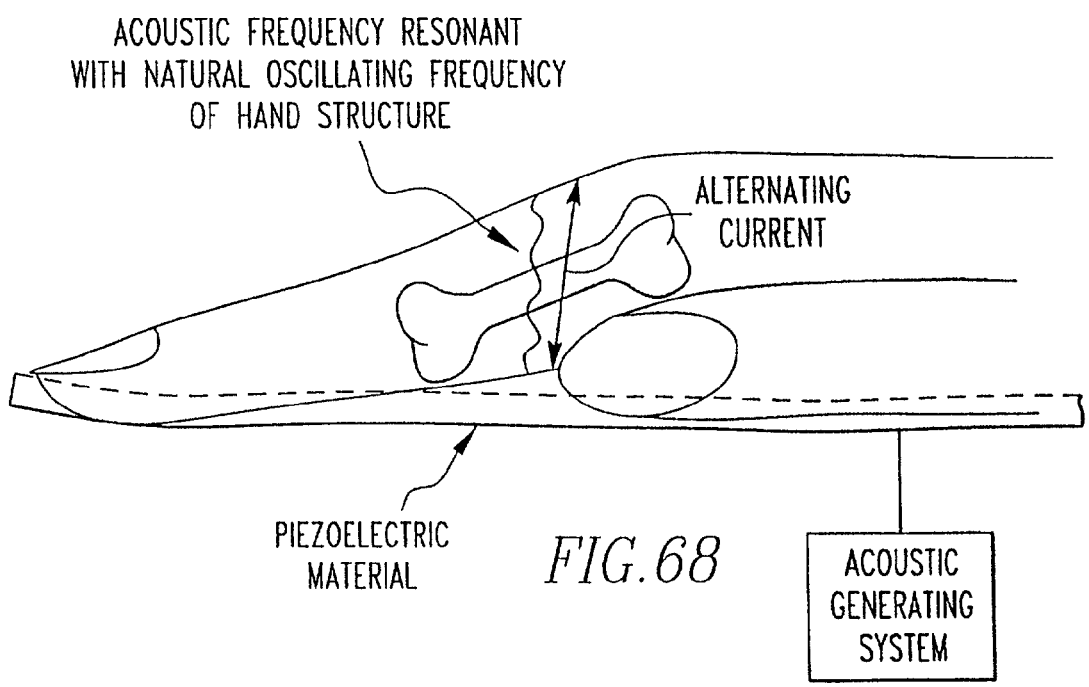

FIG. 68 shows an acoustic apparatus for the generation of alternating current and magnetic fields.

Figure 69:
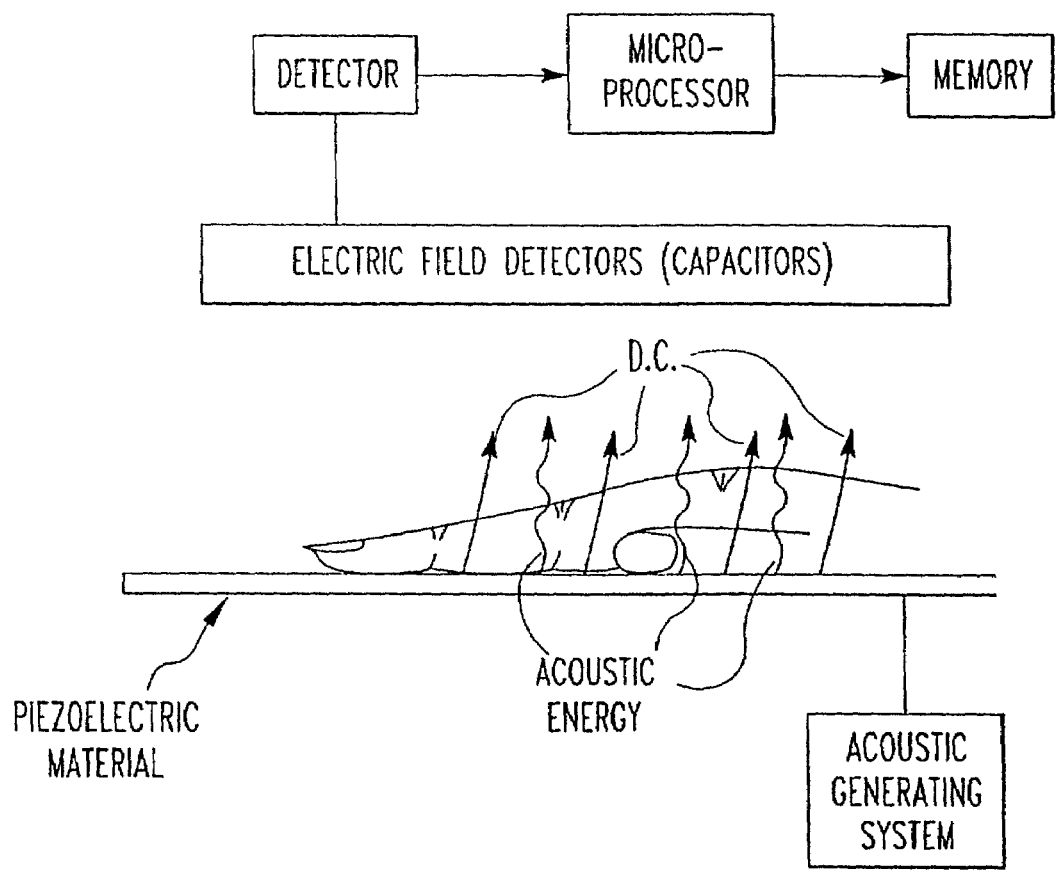

FIG. 69 shows an apparatus for detection c: direct current or alternating current induced by acoustic energy.

Figure 70:
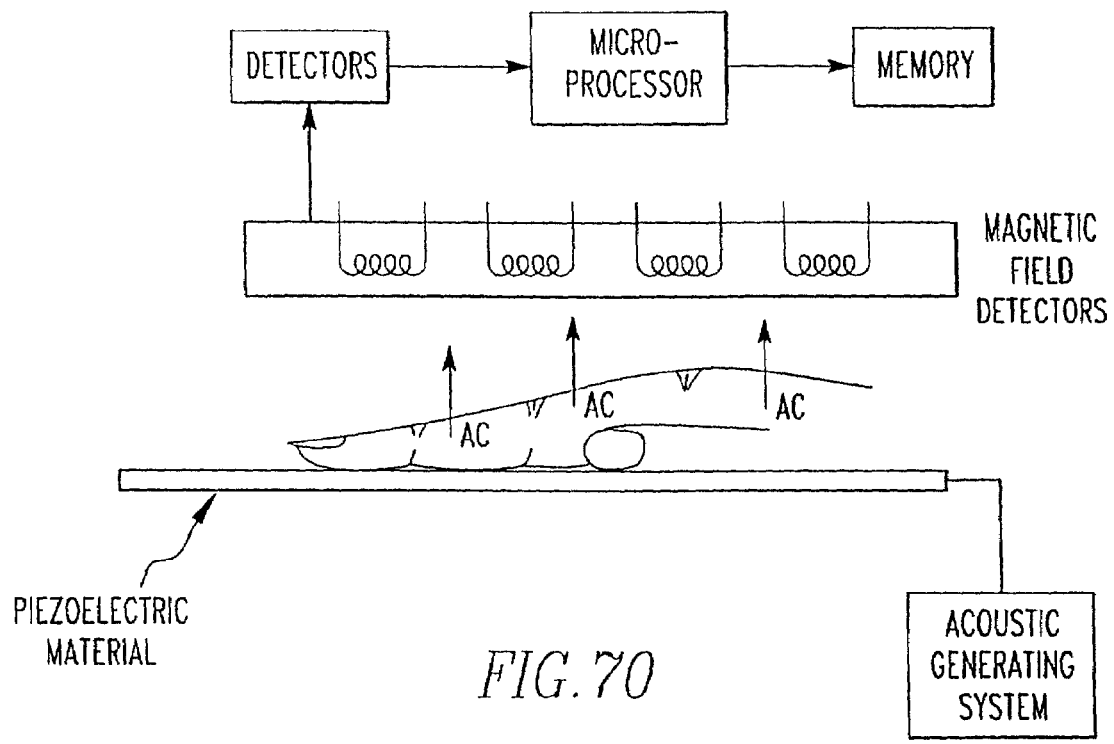

FIG. 70 shows an apparatus for the detection of alternating current induced by acoustic energy.

Figure 71:
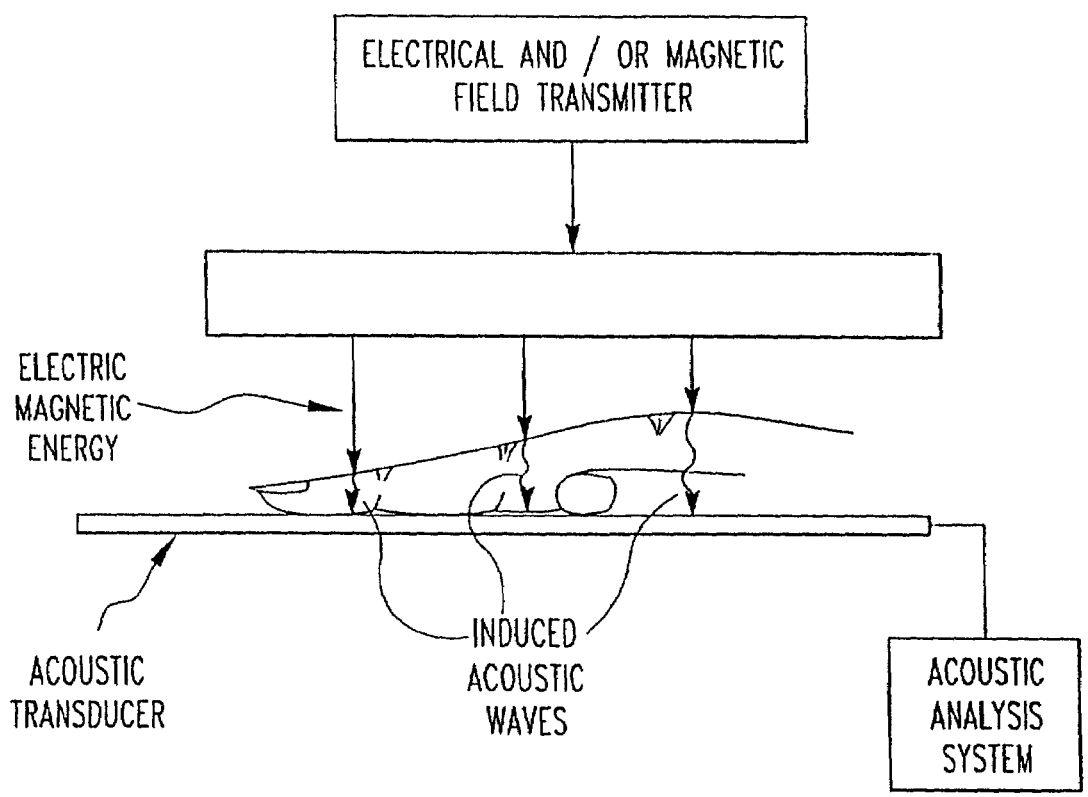

FIG. 71 shows an apparatus which produces an acoustic wave by electric and/or magnetic energy.

DESCRIPTION OF THE PREFERRED EMBODIMENT

The preferred embodiments of the present invention and their advantages are best understood by referring to FIGS. 1-11 of the drawings, like numerals being used for like and corresponding parts of the various drawings.

Before explaining the present invention in its best mode, a general explanation of electrical and magnetic properties will help to provide a better understanding of the invention. For purposes herein the term "field" herein includes but is not limited to waves, current, flux, resistance, potential, radiation or any physical phenomena including those obtainable or derivable from the Maxwell equations, incorporated by reference herein.

The electrical conductivity of a body segment depends upon a number of factors including the length and cross-sectional area of a segment of tissue and the composition of tissue including lean and fatty tissue. There may be day to day variations it conductivity and other electrical measurements due to body weight adjustments and changes in body fluids and electrolyte composition but the changes are fairly consistent through the different body segments being analyzed because of the systemic physical characteristics of each organism. For instance, it is well known in regard to clinical impedance measurements that the impedance variations in a subject due to physiological changes, are smaller than the variability among normal subjects. See "CRC Handbook of Biological Effects of Electromagnetic Fields", generally and specifically page 8, 9 and 76, incorporated by reference herein.

When measuring electrical and/or magnetic properties of an individual for biometric recognition purposes whether applying energy by the contact method or by the non-contract method, several different measurements may be utilized such as, impedance, resistance, reactance, phase angle; current, or voltage differential, across a measured body segment. For instance, impedance is a function of two components, that being the resistance of the tissue to the flow of current and reactance which is additional opposition to the current due to capacitant effect of membranes, tissue interfaces, and other biocapacitant tissue.

Many bioimpedance measurements in the prior art depend on the assumption that the relationship of body composition such as body fluid and tissue mass is dynamic, and that fluctuations occur. As fluids increase in the tissue, the bioimpedance signal decreases in value because the segment being measured has an increase in conductive potential due to the increase in fluid volume. Increases in segmental fluid volume will decrease bioimpedance values. Decreases in segmental fluid will decrease the conductive potential and thus increase the bioimpedance value. However, it is known for the operation of the present invention that the daily fluctuation is consistent systemically through the bogy and the overall ratio between impedance values taken from different segments of a body part will remain constant.

Figure 1:
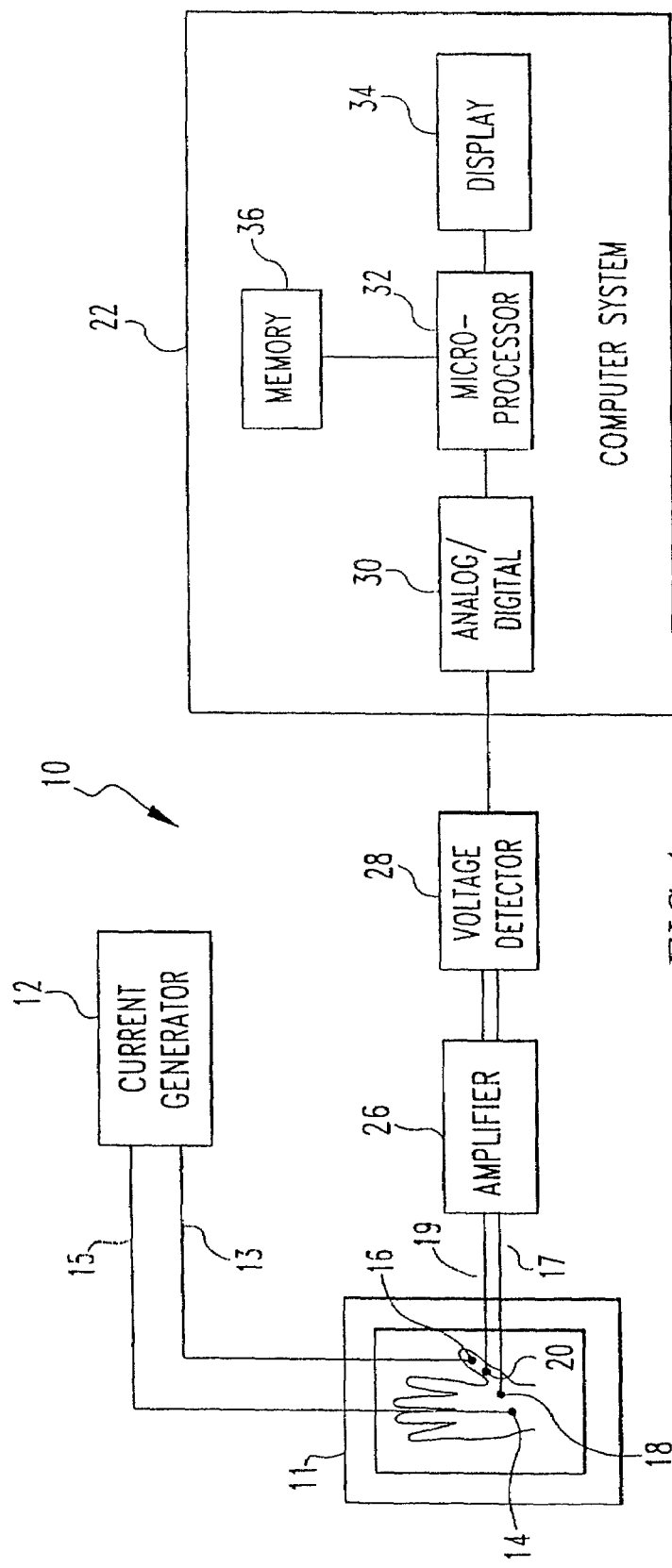
FIG. 1 comprises a block diagram illustrating one preferred embodiment of the present invention.

Referring now to the drawings, FIG. 1 describes a preferred embodiment utilizing an electrical current applied directly to the body part of a testing individual through surface contacting electrodes for generating a biometric pattern of the testing organism. Biometric recognition system 10 is a device wherein the electric and/or magnetic properties of a body segment is measured by applying an input electrical signal in the form of a constant magnitude current to the body segment tissue and measuring the resulting voltage. Since R=V/I, the measured voltage yields either a relative or calculated resistance. The voltage or resistance pattern is unique for an individual.

It is also contemplated in the present invention that a constant magnitude voltage signal is applied to the tissue and the resulting current is used to determine the bioelectrical characteristics of the testing segment.

For purposes of description, the contact system of the present invention described below uses a constant magnitude alternating current source, but direct current may be used especially in some devices that may require the introduction of an internal battery for a power source. In the event direct current is used in the contact system, an oscillator may be used to convert the direct current to an alternating current. The system 10 comprises a current generator 12 which is connected to excitation electrodes 14, 16 positioned on a body part of a testing individual, such as a hand shown in FIGS. 1 and 2. System 10 further comprises an analyzer 22 which is connected and receives an output voltage signal from receiver electrodes 18 and 20. The analyzer 22 receives the voltage output signal which is produced between electrodes caused by a flow of current between electrodes 18 and 20 in response to the current flowing from current generator 12. The current generator comprises a current source for generating a constant magnitude current. The identification system of the present invention may utilize a continuous, constant magnitude current or periodic, constant magnitude current. Periodic signals may include sinusoidal, square wave, ramp and sawtooth. Generally, the constant current magnitude ranges from about 1 microamp to 4 milliamps. Typically, the signal frequency may be between about 40 Hz to about 400 MHZ which is a frequency magnitude range within accepted risk standards for electrically susceptible humans. The present invention may utilize a single, predetermined frequency or multiple, variable frequencies within the above disclosed range. It should be noted that any frequency other than that described above may also be used in the present invention as long as electrical and/or magnetic properties of the tissue can be measured accurately. A disadvantage to using frequencies below 40 Hz can be that the measurements take longer and longer fractions of a second to complete. This can lengthen the overall time required to obtain a biometric pattern.

Each different frequency applied in the system has a different effect in the body segment due to membrane physiology, and tissue structure and composition, with accompanying changes in capacitance and inductance. When using multiple frequencies during the testing mode the output signals provide a unique biometric measurement pattern that is predictive of the individual being tested. The same is also true for changing waveform, angular frequency, capacitance and inductance at a singular frequency, as additional examples.

Figure 2:
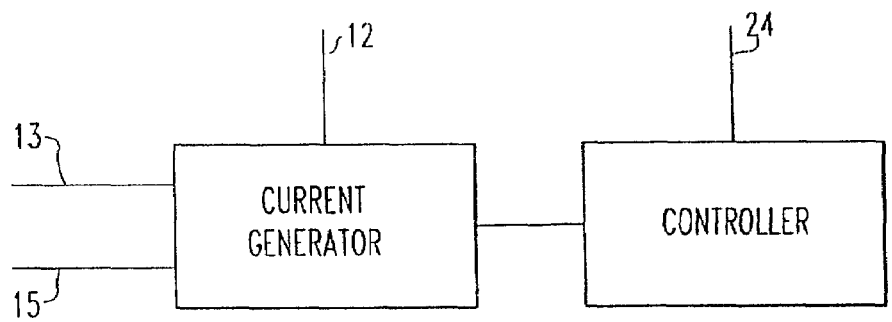
FIG. 2 is a block diagram illustrating a periodic controller connected to a current generator.
Figure 3:
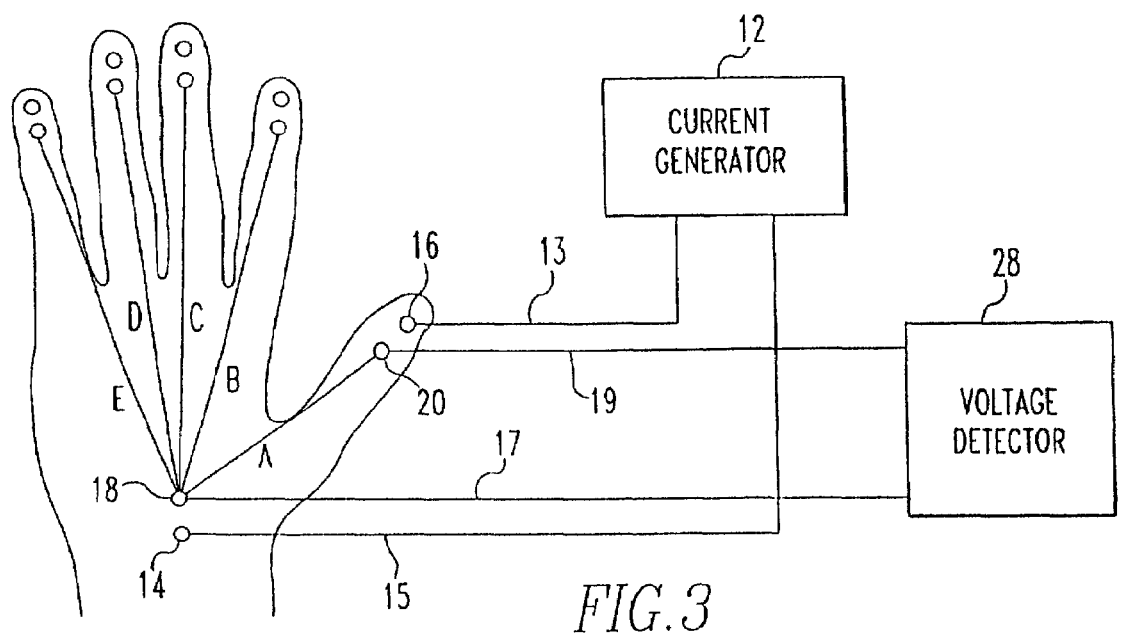
FIG. 3 is a pictorial representation of a hand attached to a biometric system of the present invention.

If a periodic, constant magnitude current is Preferred, current generator 12 may be connected to a controller 24 which is capable of generating periodic output signal to control the current generator as shown in FIG. 2. Bioimpedance measurement systems using a periodic constant current are well known in the art and described in U.S. Pat. No. 5,503,157, the disclosure of which is incorporated by reference herein.

The output signal of the current generator, is transmitted to excitation electrodes 14 and 16 through connectors 15 and 13 respectively. For purposes of illustration, FIG. 1 shows a tetrapolar electrode placement in which two of the electrodes are active for injecting the current while two electrodes are passive for detecting the resultant signal. It is contemplated that a bipolar setup or two electrodes may be utilizer in the present invention especially in systems having minimum surface area for placement of electrodes.

In the tetrapolar electrode system the first excitation electrode 14 may be positioned on the palm heel of the hand while the second excitation electrode 16 is positioned on the palmar tip of the thumb. Similar electrode pairs may be placed and spaced a sufficient distance from each other to provide a drop in voltage on the remaining four digits so that the hand will have at least five distinct segments to be tested. This is by way of example only since other electrode configurations may also be used with the present method.

The present invention prefers the tetrapolar setup of electrodes to overcome the inconsistency that may occur in the impedance measurement values due to external contact resistance. External resistance may change significantly with certain specific changes such as those due to skin moisture. As such, this can be improved by using a tetrapolar system. The tetrapolar electrode system is superior to other electrode systems in that it eliminates both electrode polarization and also contact resistance effects between the electrodes and the body part being measured. Contact resistance is variable with the motion of the subject and creates motion artifacts which interfere with measurement of electrical parameters of the body. By applying the current to the subject through one pair of electrodes and measuring voltage differences through another pair of electrodes, the contact resistance and the inherent voltage drop is eliminated from the voltage measurement. The path the energy takes is not critical, except that it should approximate the path taken for obtaining the reference pattern.

It should be understood that in some systems of the present invention, the injection of current and the sensing of the voltage may be accomplished with two electrodes for the bioelectric measurements. However, as stated earlier, with the bipolar setup the measured voltages are the voltage drops along the current pathway which include both the internal impedance and the boundary contact impedance. The voltage drop across the contact impedance can be significant compared with the voltage drop across the internal impedance. To overcome this problem when using a two-electrode system a compound electrode may be used. A compound electrode is a single electrode that incorporates an outer electrode to inject the current and an inner electrode to measure the voltage. A suitable compound electrode, for example, is disclosed by Ping Hua, 1993, Electrical Impedance Tomograpy, *IEEE Trans. Biomed. Eng.*, Jan. 40 (1), 29-34, which is incorporated herein by reference in its entirety. It should be noted that tetrapolar or compound electrodes are not necessary because switching can be used so that transmission and reception from the same electrode does not occur al the same time.

A variety of electrodes are commercially available and well known in the art such that structure and application will not be described in detail. Typically, any type of electrode known in the art that conducts an electrical signal may be used in the present invention. Of particular utility are the current synthetic conductive polymers, including polyacetylene, polypyrrole, poly-3,4-ethylene dioxythiophene, conductive adhesive polymers, semiconducting polymers, conductive silicone rubbers, and conductive rubbers all of which may be used to fabricate conductive inserts in a biometric recognition system such as shown in FIGS. 7-10.

Unit 11, shown in FIG. 1, provides a surface for placing the measured body part, such as a hand. This unit may be constructed so that the conductive electrodes are mounted on the flat surface of the holder for contact with the fingers, thumb and the palm heel. It should be understood that Unit 11 is only one embodiment envisioned by the inventor.

Since the bioelectrical measurements that are used to recognize an individual include the application or generation of current in the subject, the question of safety arises. As such, the biometric system of the present invention may further introduce the use of a transformer between the signal source generator and contacting electrodes thereby isolating the individual from potential electrical hazard. Any transformer that will transmit the required frequency associated with the constant current but will not conduct 300 cycles and preferably 60 cycles or higher of voltage in current may be utilized in this system.

Impedance to the current flow in the body segment generates a voltage difference across the body segment. The amplitude of the voltage is modulated by changes in the body segment's electrical conductivity caused by differences in tissues and structures. Receiving electrodes 18 and 20, positioned between the excitation electrodes, in this embodiment, are used to measure the voltage difference produced by the injected current through the measured segment of the body part. The receiving electrodes are generally the same types as that used for excitation electrodes. A voltage signal proportional to the body segments' impedance is generated within the body segment and the voltage difference measured between electrode 18 and 20 is an alternating voltage produced in response to the constant magnitude alternating current. The voltage detector 28 may be any type well known to designers of electronic circuitry such as a voltmeter, potentiometer and the like.

Voltage detector 28 can be of the type that detects the magnitude of the voltage signal and also detects the phase relation between the alternating voltage and the alternating current producing the voltage. Therefore, both the resistive and reactive components of impedance may be measured. This type of detector is well known to electrical designers and often termed synchronous detectors. Impedance measuring systems utilizing synchronous detectors are described in U.S. Pat. Nos. 3,871,359 and 5,063,937, the contents of which are incorporated by reference herein.

Before the voltage signal is received by the voltage detector 28 and depending on the strength of the signal, an amplifier 26 may be connected between the signal received from the receiver electrodes 18 and 20 and the voltage detector. The amplifiers which can be advantageously used in the present invention are well known and widely used in electronic circuitry art. A suitable amplifier to be used in the present invention will take a signal less than a millivolt and amplify it to volts, will produce a large voltage gain without significantly altering the shape or frequencies present, and provide accurate measurements.

It is further contemplated in the present invention to provide a means to eliminate noise from the signal. As such, a differential amplifier may be used in the present invention to remove background noise. If a differential amplifier is used another electrode will need to be added to the bioimpedance system to serve as a common ground.

Figure 4:
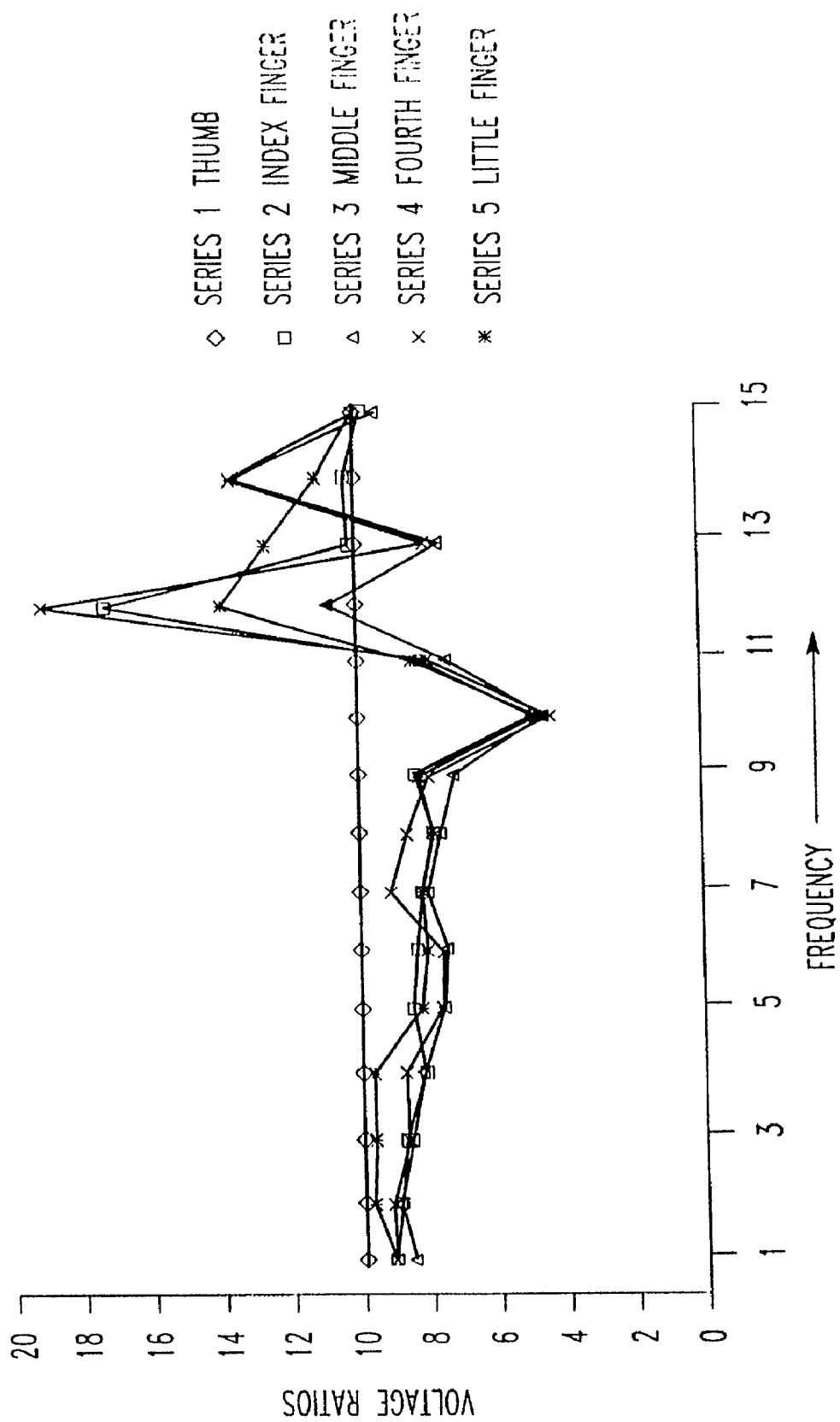
FIG. 4 is a representative graph of resistance measurement values plotted against multi-frequencies.
Figure 5A:
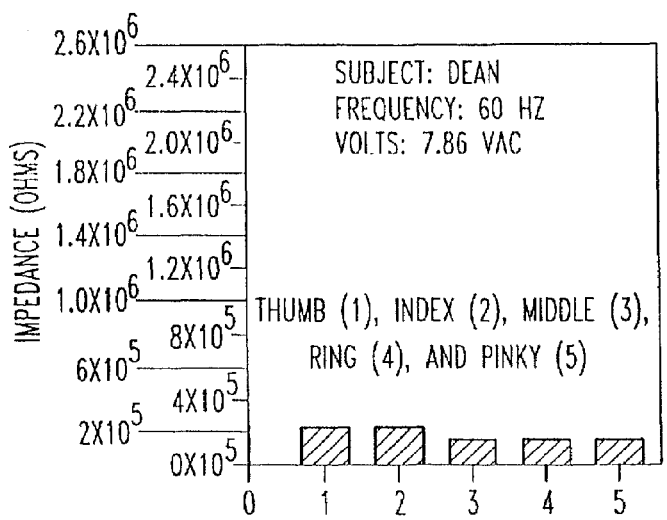
FIGS. 5a-5f are charts of subjects regarding impedance and finger.
Figure 5B:
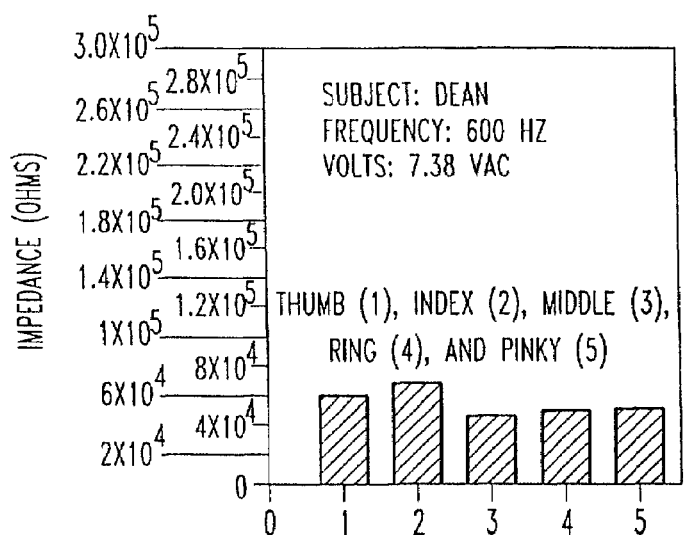
Figure 5C:
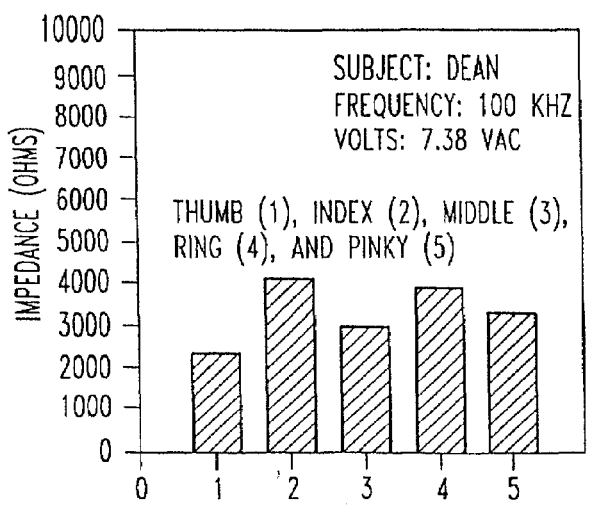
Figure 5D:
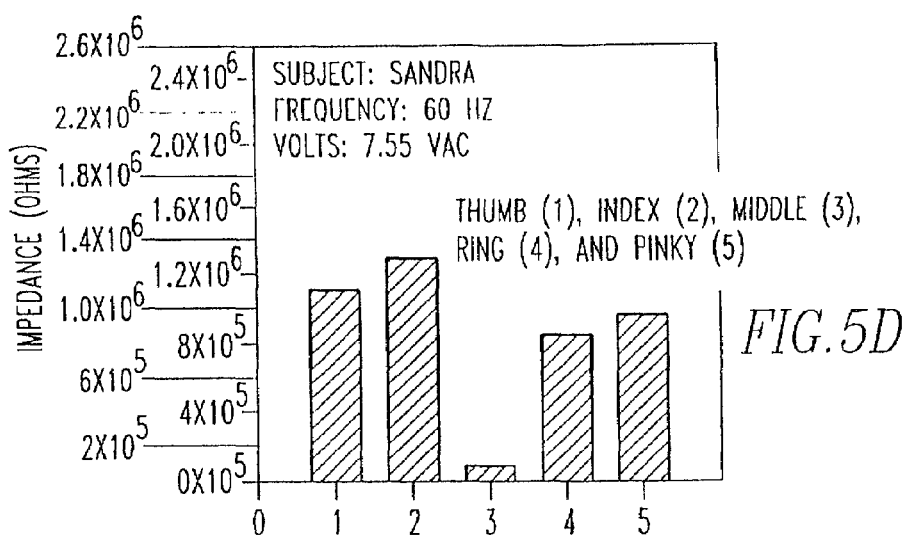
Figure 5E:
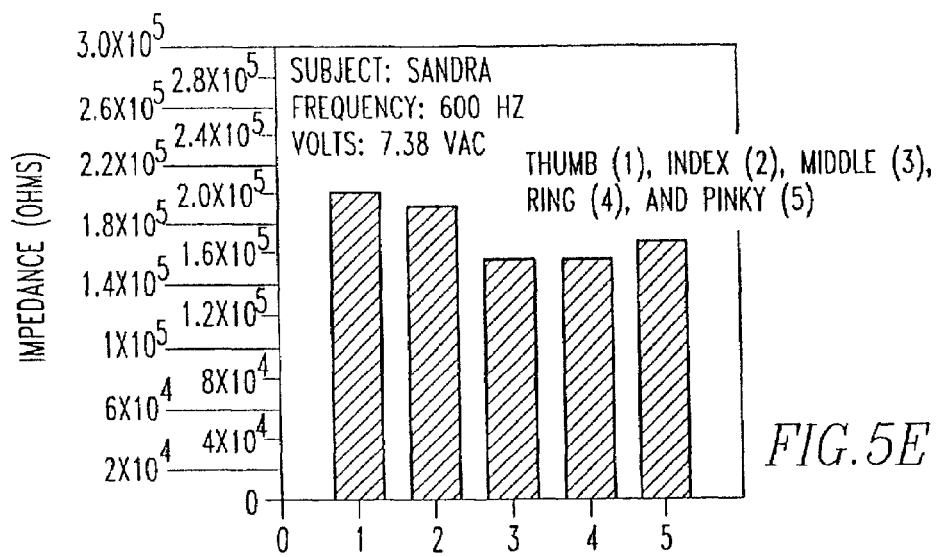
Figure 5F:
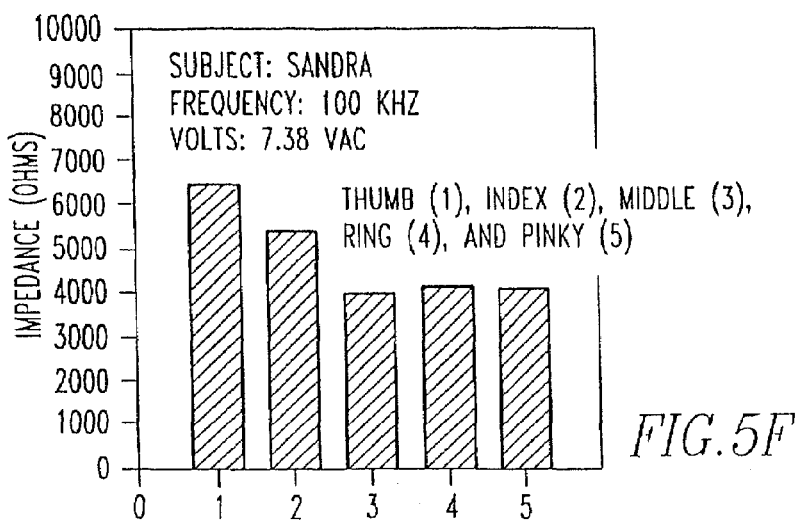
Figure 6A:
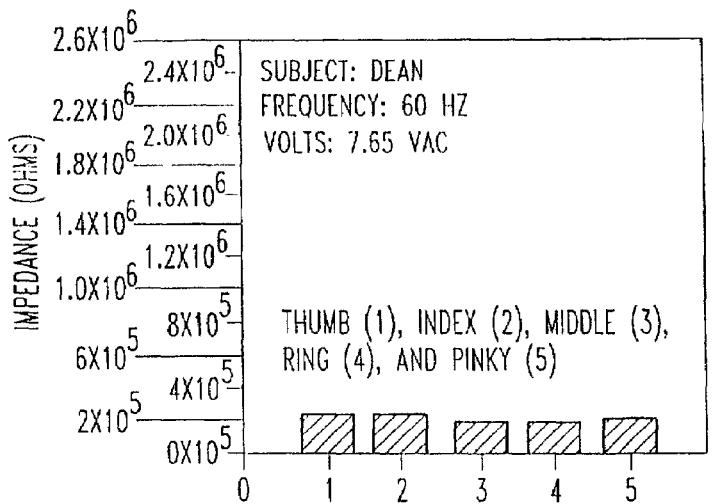
FIGS. 6a-6e are charts of subjects regarding impedance and finger.
Figure 6B:
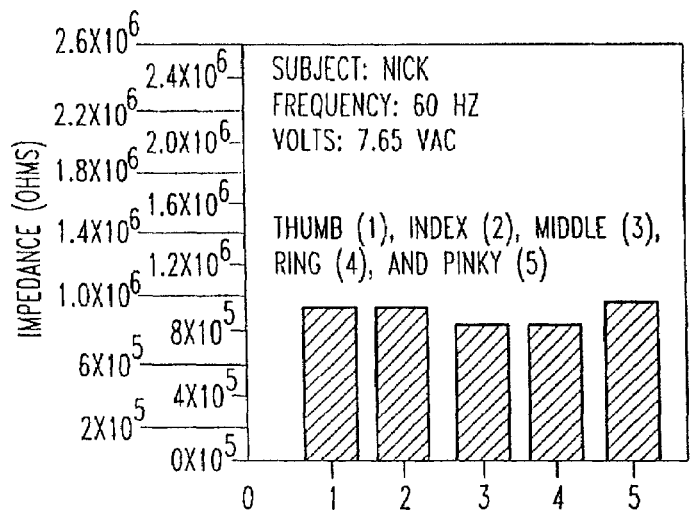
Figure 6C:
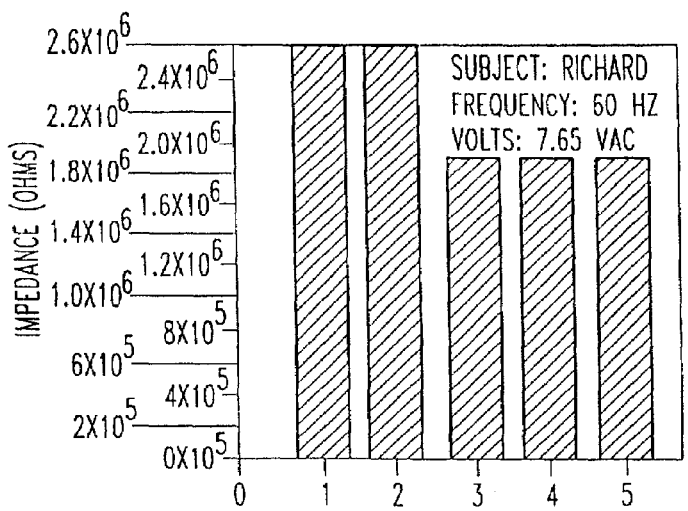
Figure 6D:
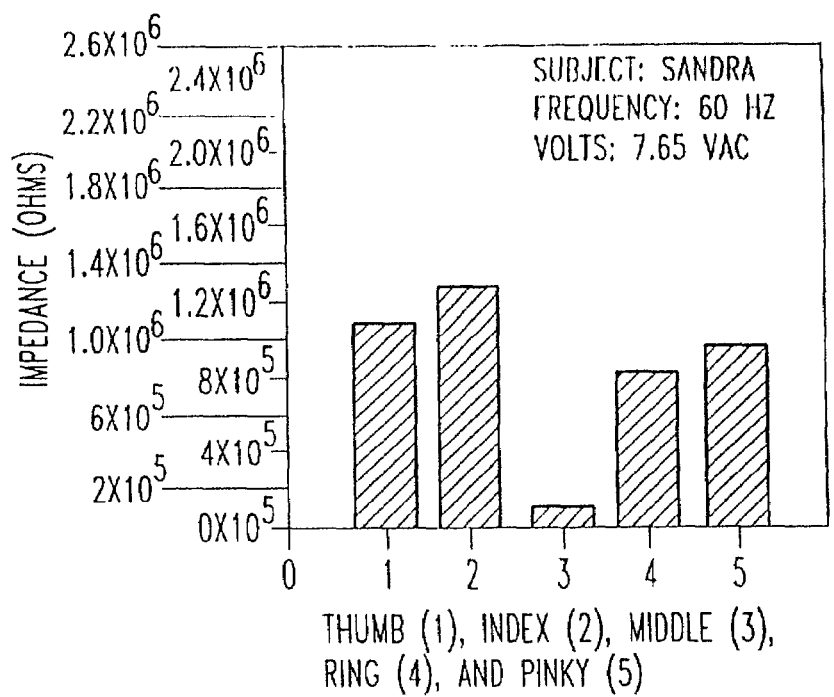
Figure 6E:
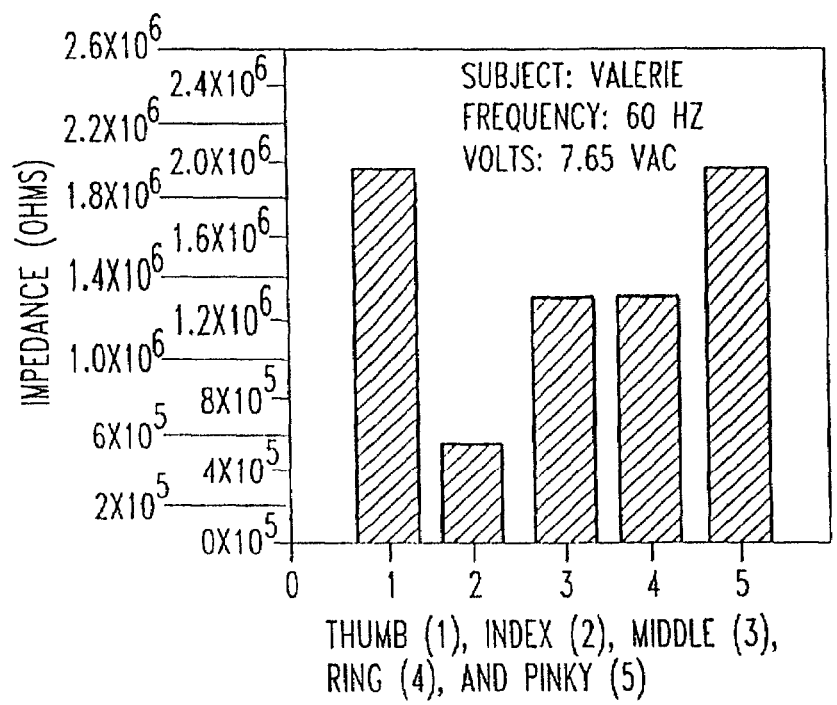

Once the voltage signal is measured, the signal may be directed through an analog to digital converter 30 and the digital signal is directed into a microprocessor 32 which can automatically and instantaneously calculate impedance or any of the other bioelectrical characteristics of the body segment. Any general purpose computer or one capable of performing various mathematical operations on the voltage input information may be used in the present invention. A typical mathematical operation contemplated on the signal within the scope of this invention is the division of one impedance value by a subsequent detected impedance value from a second segment of a body part to compute a comparative ratio. The computation of a representative bioimpedance measurement pastern is illustrated by referring to FIG. 3. The voltage difference in each of five different segments that being A, B, C, D, and E are detected and subsequently a comparative ratio is determined by dividing one signal detected by a subsequent detected value. As an example A/A, B/A, C/A, D/A and E/A are computed and the resultant values give four comparative ratios for the body part for a predetermined frequency. This yields a ratio of each finger to the thumb, for instance. Then when measurements are taken on another day, even though the absolute measurements will vary, the ratios are still the same (to within 0-6%). If the frequency is then changed, another set of comparative ratios may be determined for the same body part. The more frequencies applied the larger the set of comparative ratios which may be used as a unique representative bioimpedance measurement pattern. FIG. 4 shows a set of the comparative ratios identified above, with series 1 (the thumb) set to 10. The frequencies measured were in Hz (on the horizontal axis 1-15):

10
20
50
100
200
500
1,000
2,000
5,000
10,000
20,000
50,000
100,000
200,000
500,000.

Frequency #10 (10,000 Hz) is an impedance resonance point for the thumb, while the fingers have resonance points around 50,000 Hz.

FIGS. 5a-5f are charts of subjects showing impedance versus the fingers of the same subjects at different frequencies. FIGS. 6a-6e are charts of subjects showing impedance versus the fingers of several subjects at the same frequency.

Another operation contemplated is the computation of impedance values or any of the other bioelectrical and/or magnetic characteristics for each segment for a plurality of frequencies. The results of these values plotted against the range of multi-frequencies will provide a representative bioelectric measurement pattern in the form of a unique curve for each body segment, for example FIG. 4 shows a plot for segment A of FIG. 3 over range of multi-frequencies.

The results of the computations are compared with a previously stored reference pattern stored in memory 36 to determine a match within an acceptable error range.

The results from the comparison are displayed on display unit 34 which may be a digital display component of the microprocessor.

While the present invention has been described using the flat hand detector, it should be appreciated that other embodiments of the described system and it elements may be used in other devices to gain access to or activate certain secure systems. For example, FIGS. 7, 8, 9, and 10 illustrate just a few of the contemplated setups and uses for the biometric recognition utilizing unique electrical conductivity values of an individual.

Figure 7:
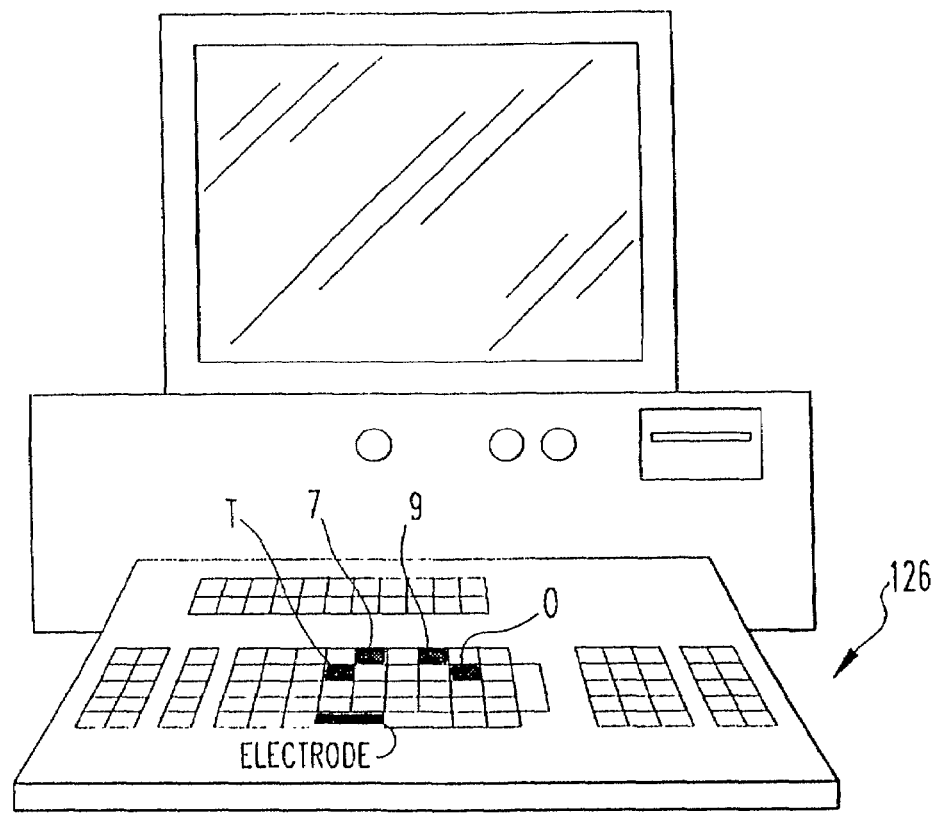
FIGS. 7 and 8 show alternative embodiments illustrating the biometric recognition system utilized in a keyboard and mouse.

FIG. 7 illustrates a computer keyboard having electrodes imbedded in specific keys for generating bioelectrical conductivity values. If the user's bioelectrical pattern matches that of an authorized individual the computer is activated and the person is allowed to log on.

Figure 8:
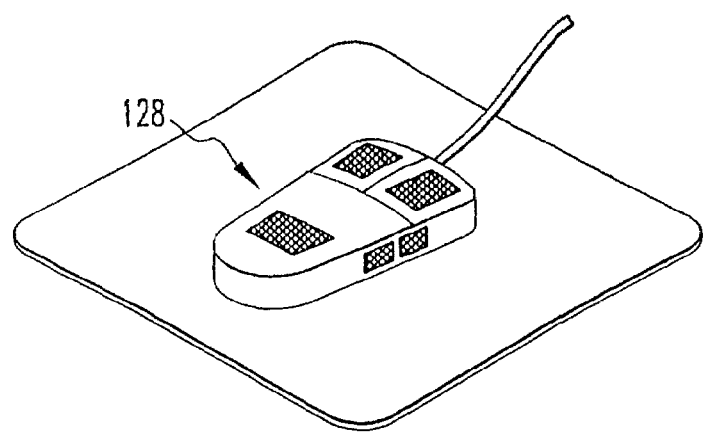

FIG. 8 illustrates another embodiment for access to a secure system using the mouse of a microprocessor. This system will recognize authorized users and prevent others from gaining access to the system.

Figure 9:
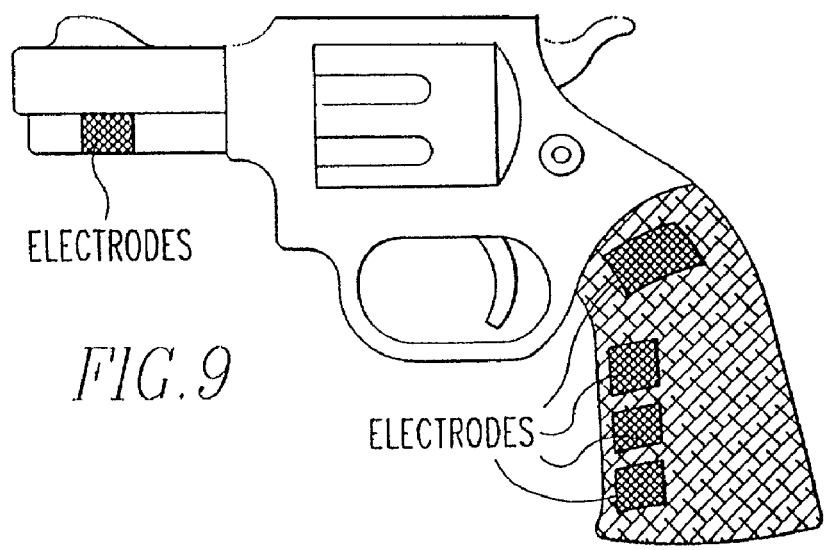
FIG. 9 is an illustration showing the biometric recognition system of the present invention incorporated into the handpiece of a firearm.

FIG. 9 provides a system to limit the use of a weapon such as a firearm to only the authorized user. If an unauthorized individual attempts to discharge the weapon, the system will not recognize the individual thereby preventing the activation of the firing mechanism.

Figure 10:
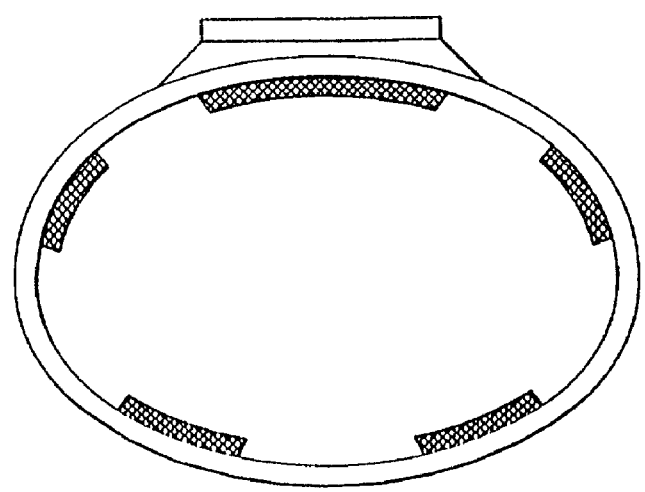
FIG. 10 is an illustration showing the biometric recognition system incorporated into a wrist watchband.
Figure 11:
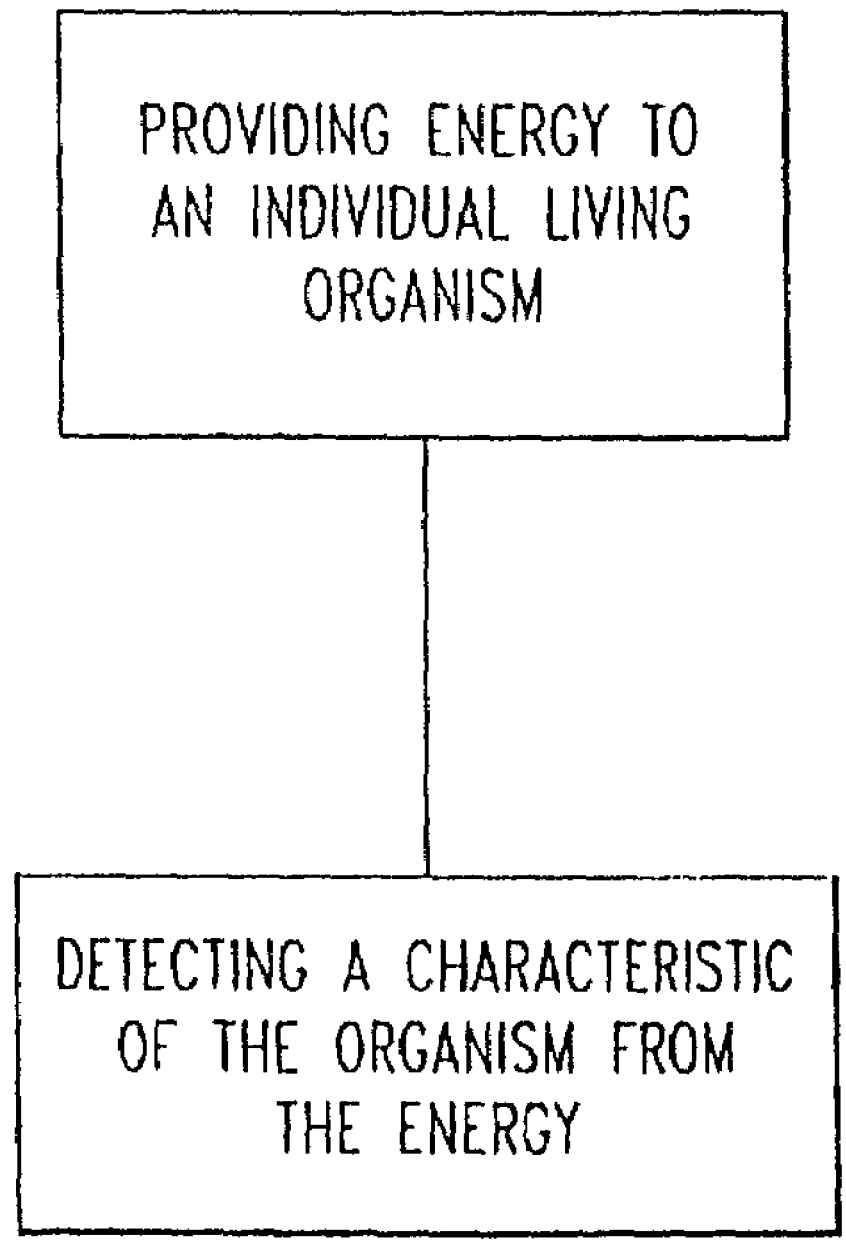
FIG. 11 is a flow chart of a method of the invention.

FIG. 10 provides for a simple recognition system that merely provides an individual's biometric characteristic pattern. The measurement electrodes are contained within the watchband wherein conductivity and/or other electrical values are measured in the wrist of an individual. An auxiliary receiving system recognizes the pattern sent from the watch and verifies the identity of the user. This watch, emitting a unique pattern may be used to open an electronic door lock and replaces the need for a keypad or a remote control unit. FIG. 11 is a flow chart of a method of the invention.

Figure 12A:
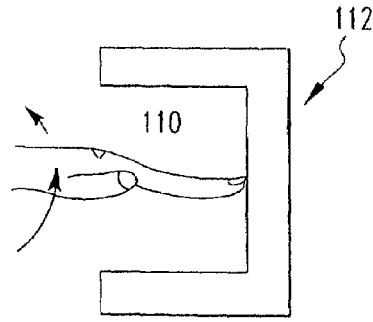
FIGS. 12a and 12b are side and overhead views of a non-contact apparatus for the interruption of an electric field of the present invention.
Figure 12B:
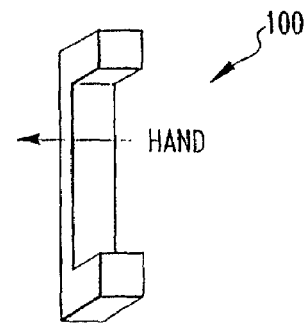
Figure 13:
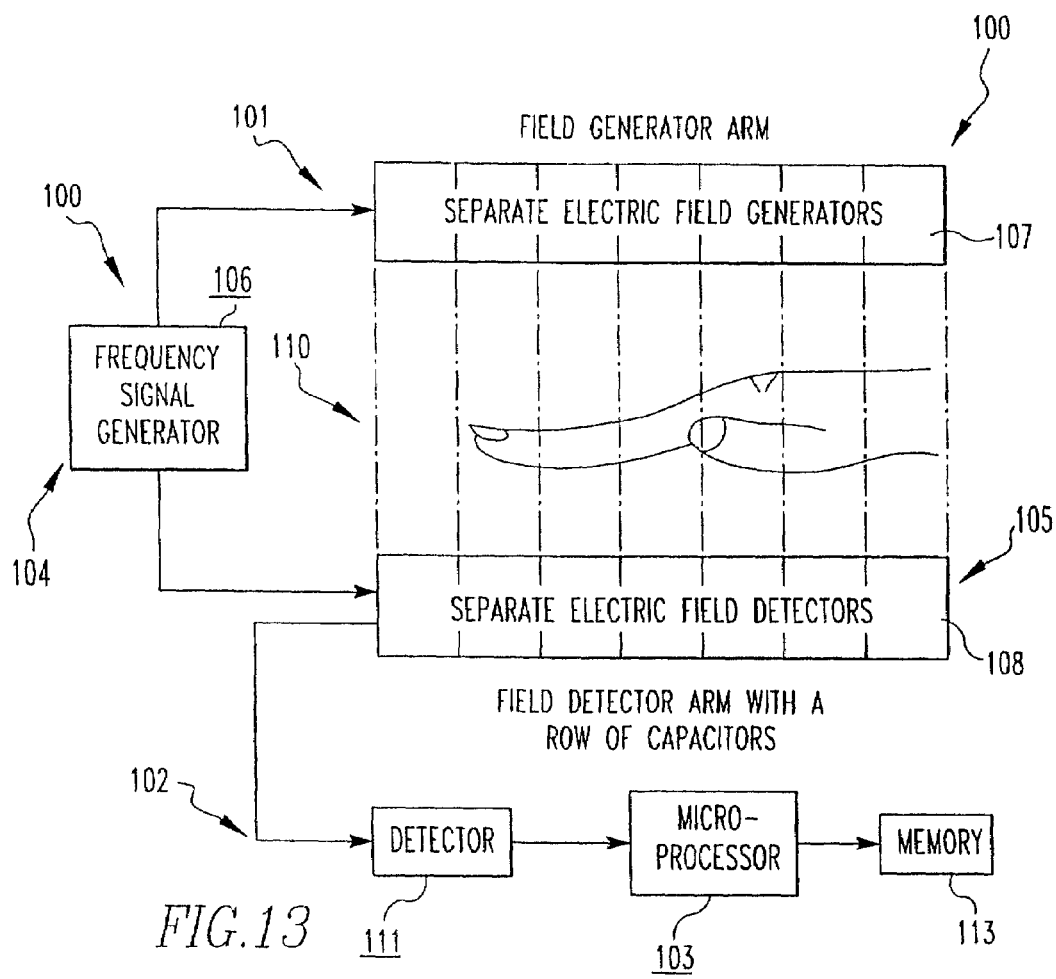
FIG. 13 is a schematic representation of an apparatus for sensing electric or magnetic properties of an organism.
Figure 14:
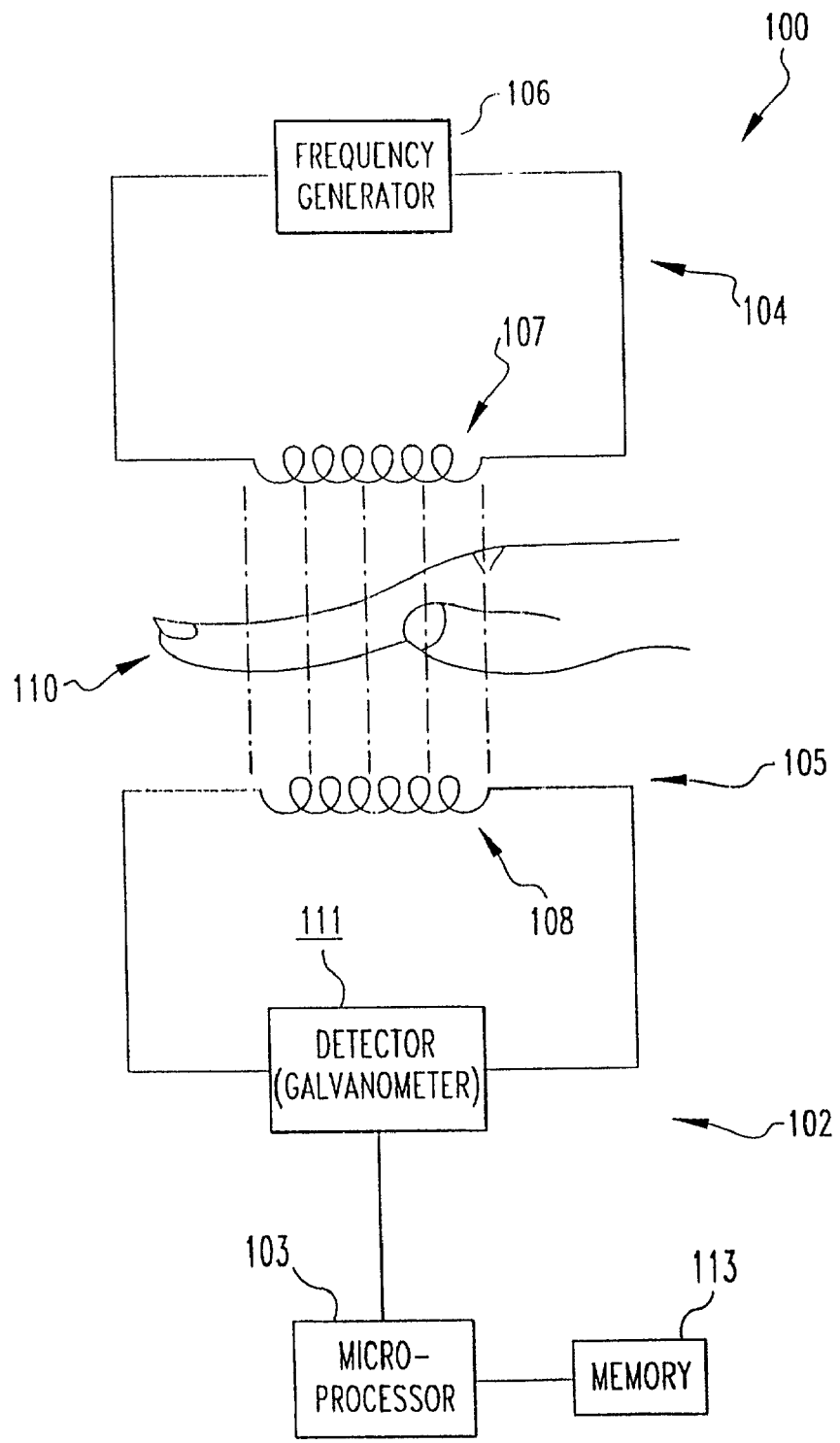
FIG. 14 is a schematic representation of an apparatus for sensing the magnetic properties of an organism.
Figure 15:
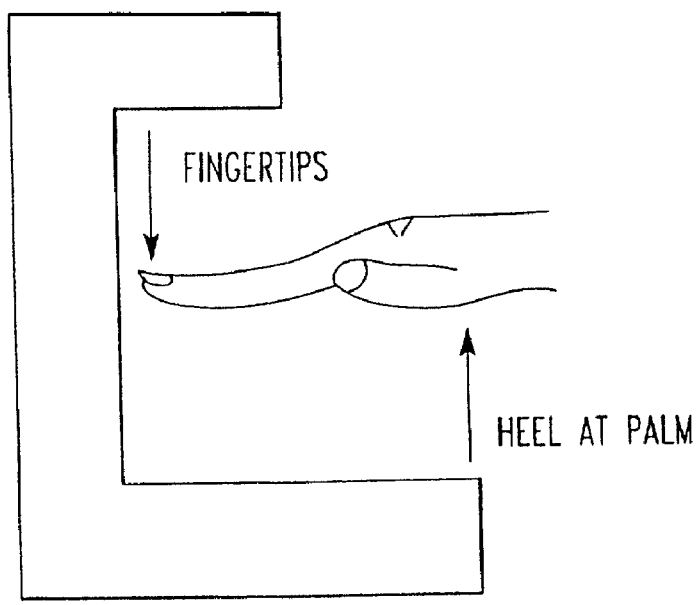
FIG. 15 is a schematic representation of an apparatus for inducing current longwise in an organism.
Figure 16:
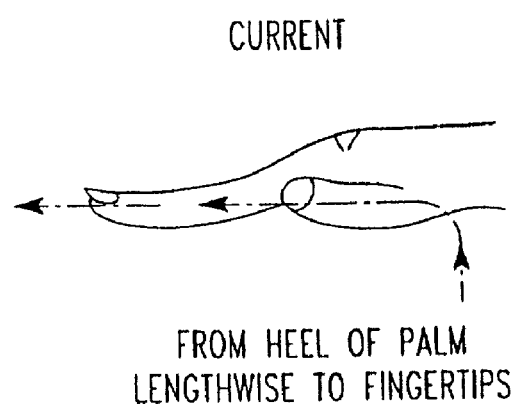
FIG. 16 is a schematic representation of the flow of induced current from the heel of the palm lengthwise to She finger tips.
Figure 19:
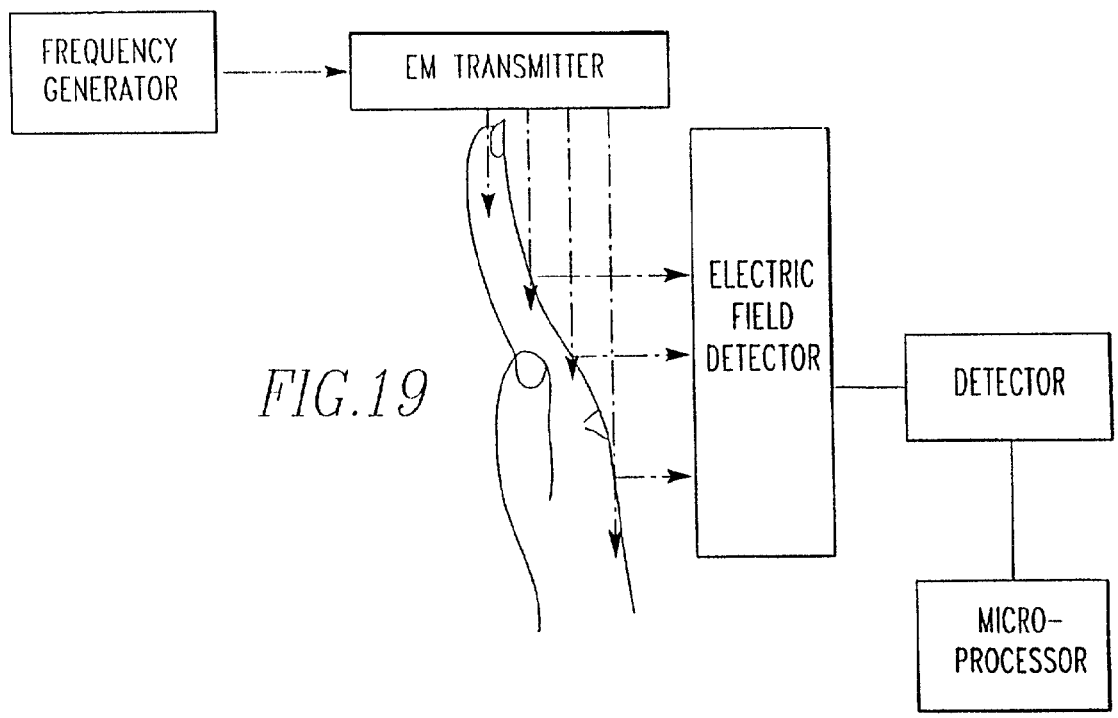
FIG. 19 is a schematic representation of an apparatus for inducing current in an organism using an electromagnetic field.
Figure 20:
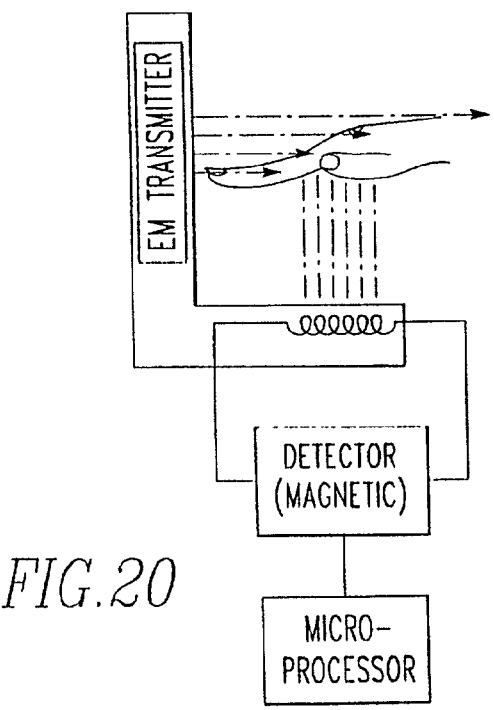
FIG. 20 is alternative embodiment of an apparatus for inducing current in an organism with an electric and/or magnetic field.

Referring to FIGS. 12, 13 and 14, the present invention pertains to an apparatus 100 for recognition of an individual living organism's identity. The apparatus 100 comprises a sensing mechanism 101 for sensing electric and/or magnetic properties of the organism. The apparatus 100 comprises a mechanism 102 for recognizing the organism. The recognizing mechanism 102 is in communication with the sensing mechanism 101.

Preferably, the recognizing mechanism includes a microprocessor 103 having a known electric and/or magnetic property of the individual organism. The sensing mechanism 101 preferably includes a mechanism 104 for producing an electric field and/or magnetic field in the organism, and a mechanism 105 for receiving the electric field and/or magnetic field. Preferably, the producing mechanism includes a frequency generator 106 and an electric field transmitter 107 and/or magnetic field transmitter 107 transmitter connected to the frequency generator 106, and the receiving mechanism 105 includes an electric field receiver 108 and/or magnetic field receiver 108 disposed adjacent to the electric field transmitter 108 or magnetic field transmitter and defining a test zone 110 with the electric field or magnetic field in which a portion of the individual organism is placed for sensing the electric or magnetic properties of the individual organism, and a detector 111 connected to the electric field or magnetic field receiver 108 and the microprocessor 103.

The detector mechanism, preferably measures phase or amplitude or frequency or waveform of the electric filed or magnetic field or acoustic field which extends through the test zone received by the receiver. The apparatus 100 can include a housing 112, and the transmitter and receiver are disposed in the housing. See also U.S. Pat. No. 4,602,639 incorporated by reference, herein.

In operation, a standard frequency generator, well known to one skilled in the art, is connected to an electric and/or magnetic field transmitter, well known to one skilled in the art. For a complete discussion of designing magnetic and electric fields, see "Introduction to Electromagnetic Fields and Waves" by Erik V. Bohn, Addison-Wesley Publishing Co. (1968), incorporated by reference herein. The frequency generator controls and drives the electric and/or magnetic field transmitter which produces an electric and/or magnetic field. Opposing the electric and/or magnetic field transmitter in one embodiment, is an electric and/or magnetic field receiver. Between the electric and/or magnetic field transmitter and the electric and/or magnetic field receiver is a test zone defined by the transmitter's and receiver's location. The test zone is where the individual organism places a portion of himself or herself, such as a hand, so the hand is in the electric and/or magnetic field that exists between the electric and/or magnetic field transmitter and the electric and/or magnetic field receiver. The presence of the hand, or other portion, causes the electric field and/or magnetic field to extend through the hand and the energy of the electric and/or magnetic field is affected in a unique way corresponding to the individual organism.

The electric and/or magnetic field receiver receives the electric and/or magnetic field. The detector produces a signal corresponding to the electric field and/or magnetic field received by the receiver and provides the signal to the microprocessor. The microprocessor has stored in its memory 113 a known electric and/or magnetic field signal for the individual organism. The microprocessor calls up the stored known signal and compares it to the signal provided to the microprocessor from the detector. If the known signal and the signal from the detector are substantially similar, then the individual organism is recognized.

The detector can measure phase, amplitude, frequency, waveform, etc., of the electric and/or magnetic field which extends through the test zone and the portion of the individual organism in the test zone. Either an electric field by itself, or a magnetic field by itself or a combination of both can be present for the test zone. If frequency is used for recognition, then preferably the frequency is DC to 500,000 Hertz. If current is used for recognition, then preferably the current is 1 microamp to 4 maAmp. If potential energy is used for recognition, then the voltage is preferably 0.1 to 15 volts. If waveforms are used for recognition, then sine, ramped, square, or combinations thereof can be used. In regard to the use of an electric field for recognition, preferably an electric field of 20 to 700V/m squared is used. In regard to the magnetic field for recognition, a magnetic field of between 100 mGauss to 10 Gauss is preferred.

Basically, the hand or other portion interrupts a steady electric and/or magnetic field, and the detector measures the amount of interruption. See, U.S. Pat. Nos. 4,493,039; 4,263,551; 4,370,611; and 4,881,025, incorporated by reference herein. For an electric field, the measurements could be from the back of the hand straight through to the palmar surface, although it would depend on how the transmitter and receiver are positioned. If a sweeping motion of the hand is used through the test zone, straight through measurements would be obtained first for the thumb, and then for each of the fingers in sequence. This results in five sets of data. In regard to the magnetic field, placement of the hand in the test zone would interrupt the current induced in the secondary coil from the magnetic flux created by the primary coil, as shown in FIG. 14.

Preferably, the hand is used as an essential part of the current path. A current is induced by placement of the heel of the palm over a magnetic and/or electric field as shown in FIGS. 15, 16, 17, and 18 in the embodiment of the apparatus 10, and the induced currents at the finger tips are detected, either with a magnetic and/or electric field sensor.

The present invention pertains to a method for recognition of an individual living organism's identity. The method comprises the steps of sensing electric and/or magnetic properties of the organism. Then there is the step of recognizing the organism from the properties.

The different embodiments described herein revolve about the fact that a subject organism by being somehow present in, or more specifically part of, a circuit that is either electrically based or magnetically based or a combination of both, interferes or affects the energy in that circuit in a unique way. By knowing how the subject individual interferes or affects the energy in the circuit a priori, and then testing again under essentially the same conditions how the subject individual interferes or affects the energy in the circuit, the test information can be compared to the previously identified information, and the identity of she subject individual can be either confirmed or rejected.

Figure 21:
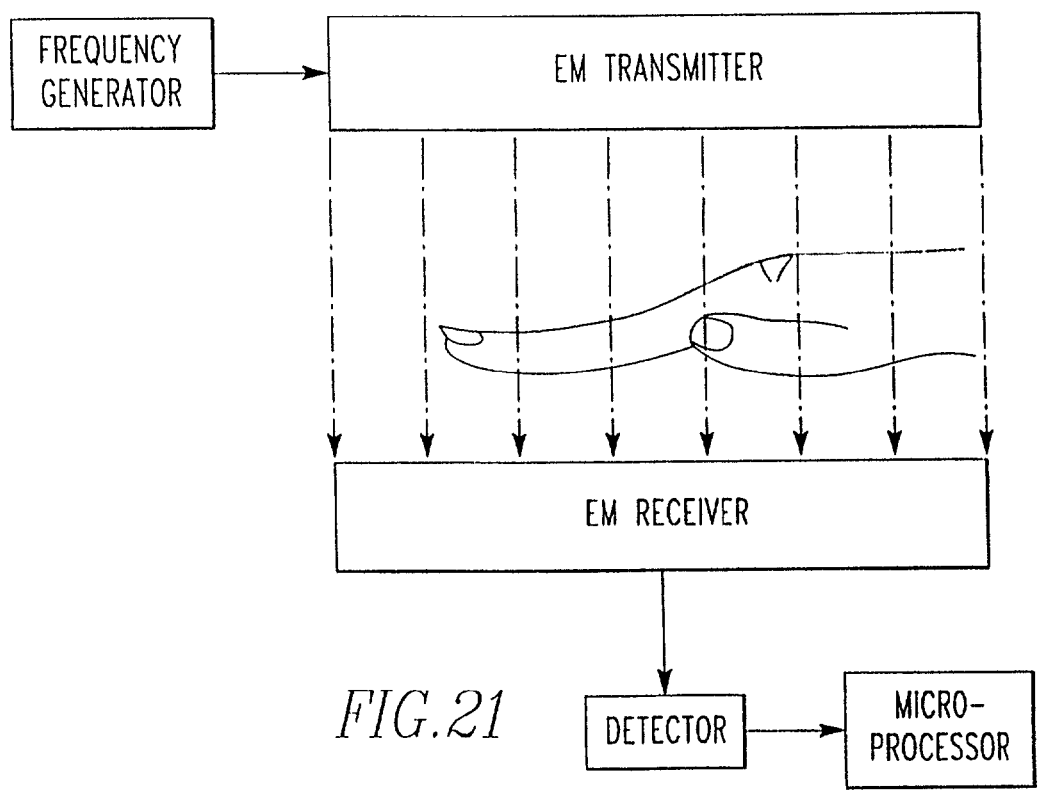
FIG. 21 is a schematic representation of an apparatus for sensing the interruption of an electromagnetic field.
Figure 22:
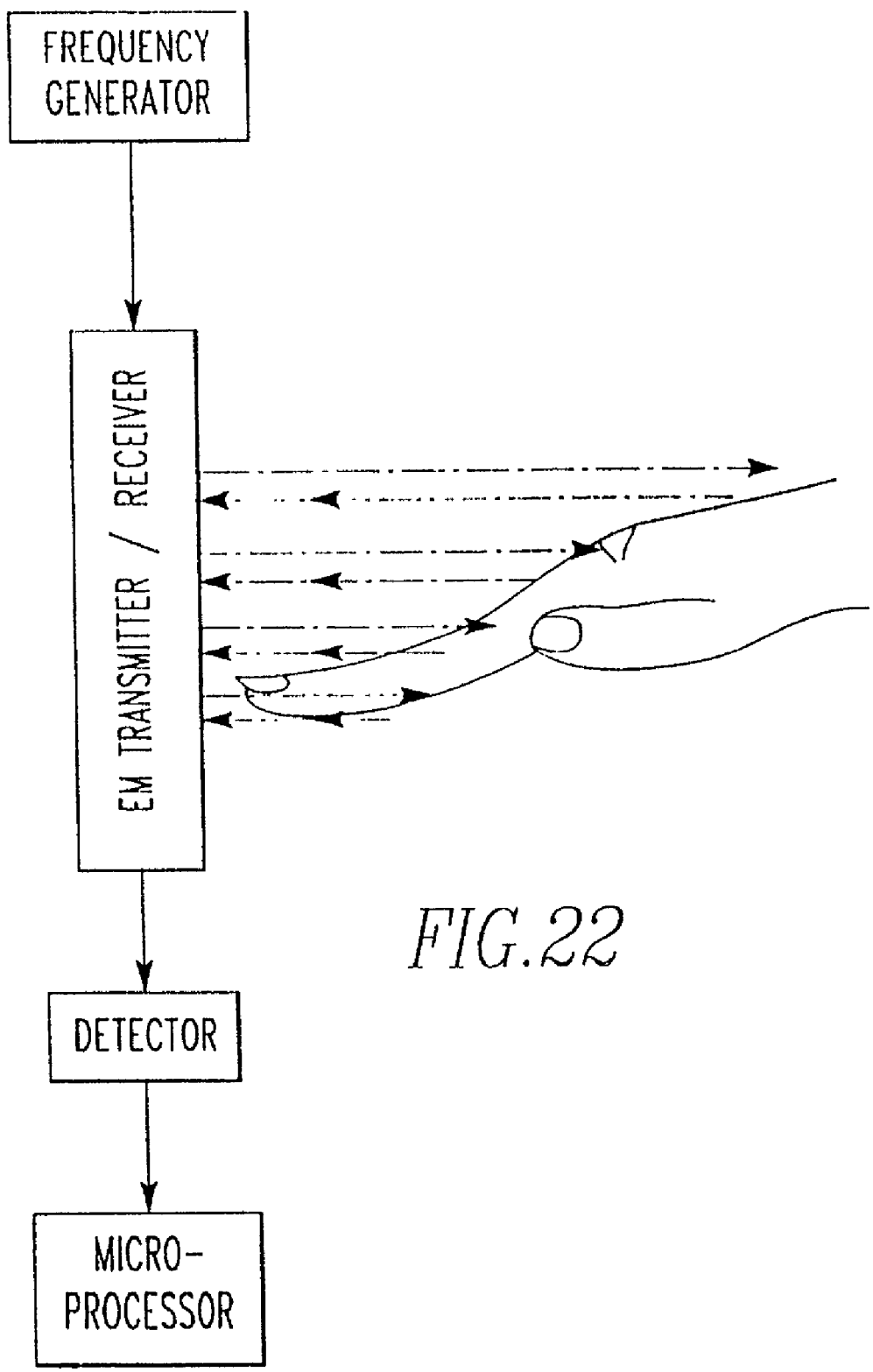
FIG. 22 is a schematic representation of sensing electric and/or magnetic properties based upon reflection of electromagnetic radiation from an organism.
Figure 23:
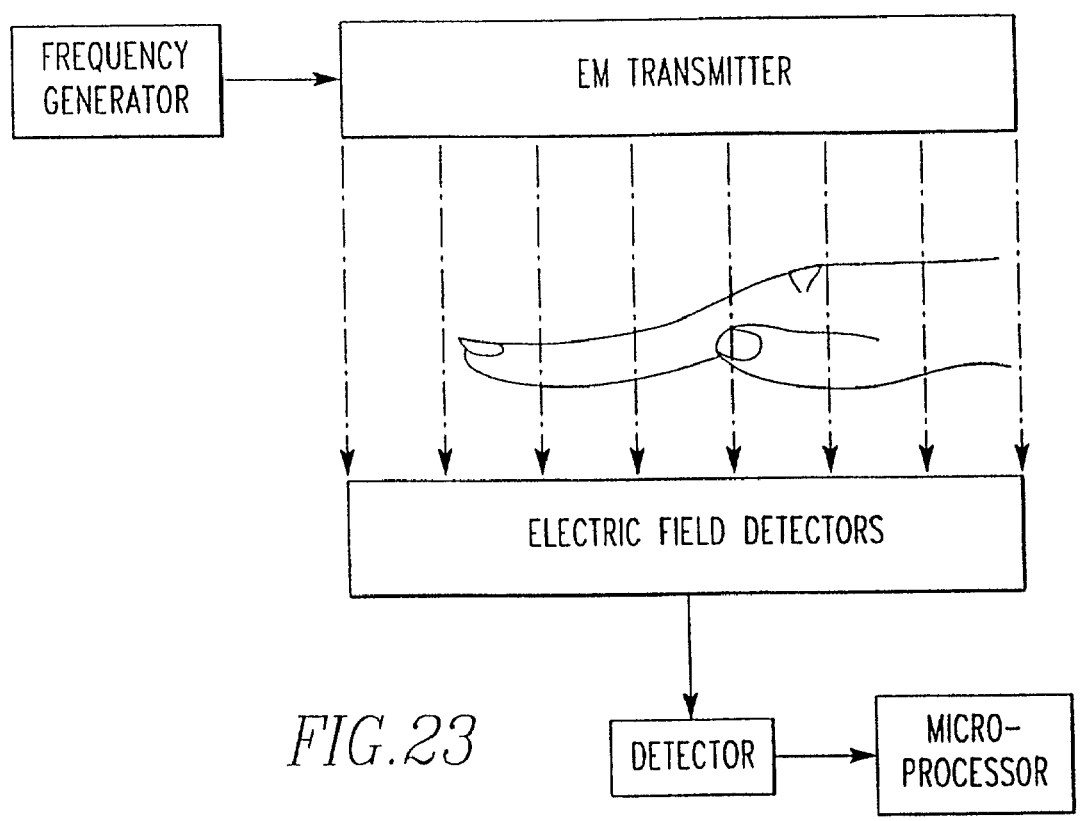
FIG. 23 is a schematic representation of an apparatus for measuring the interruption of an electromagnetic field by measuring only the electric field.
Figure 24:
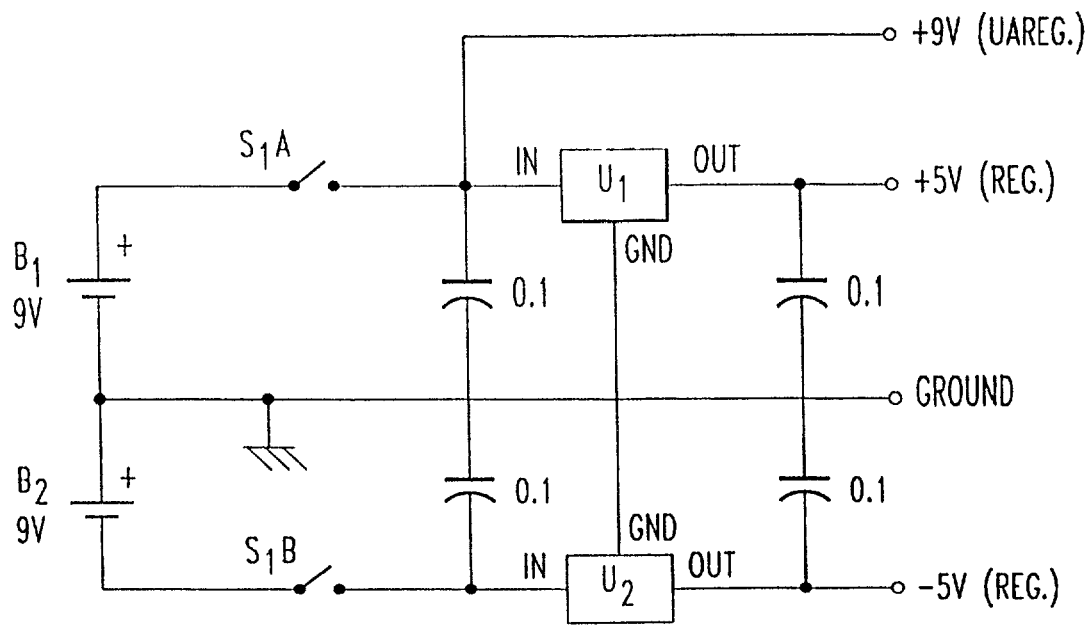
Figure 25A:
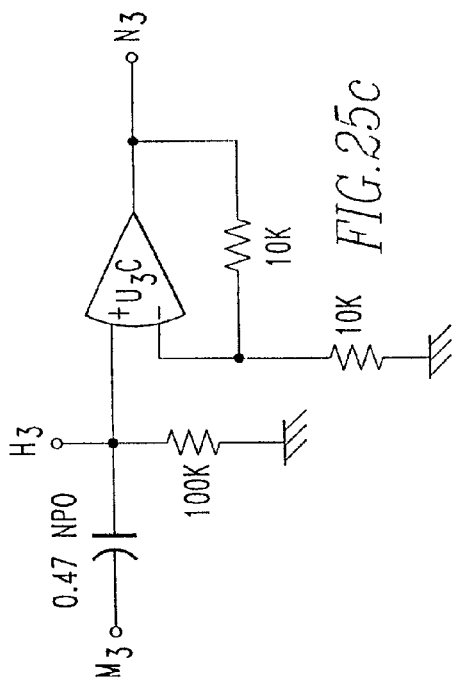
Figure 25B:
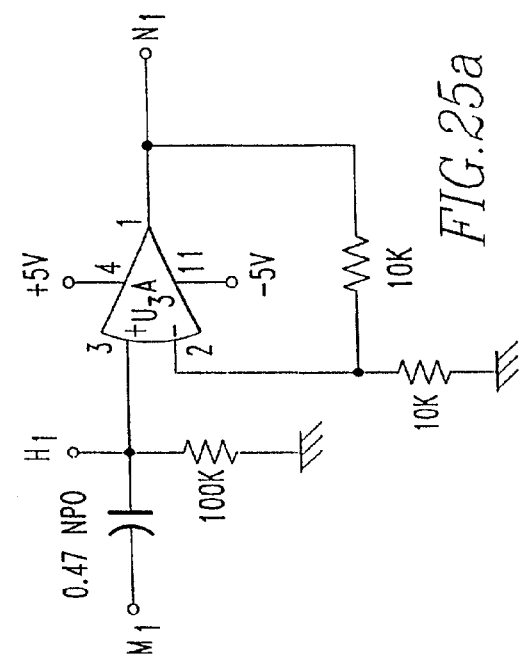
Figure 25C:
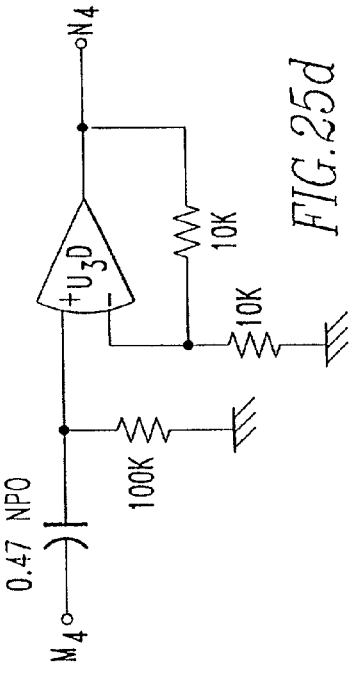
Figure 25D:
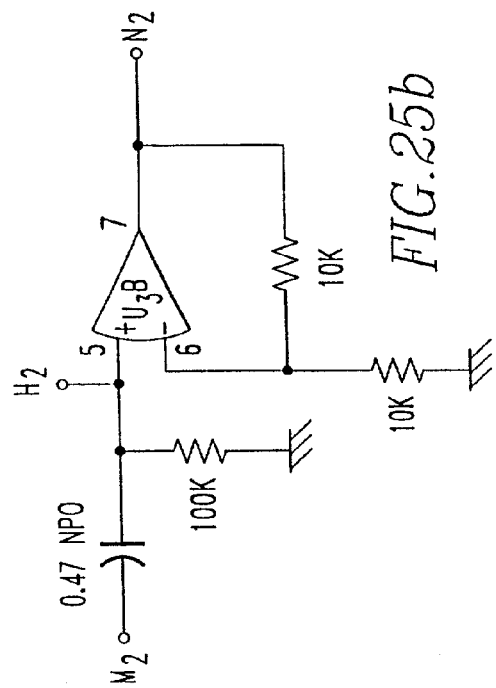
Figure 27:
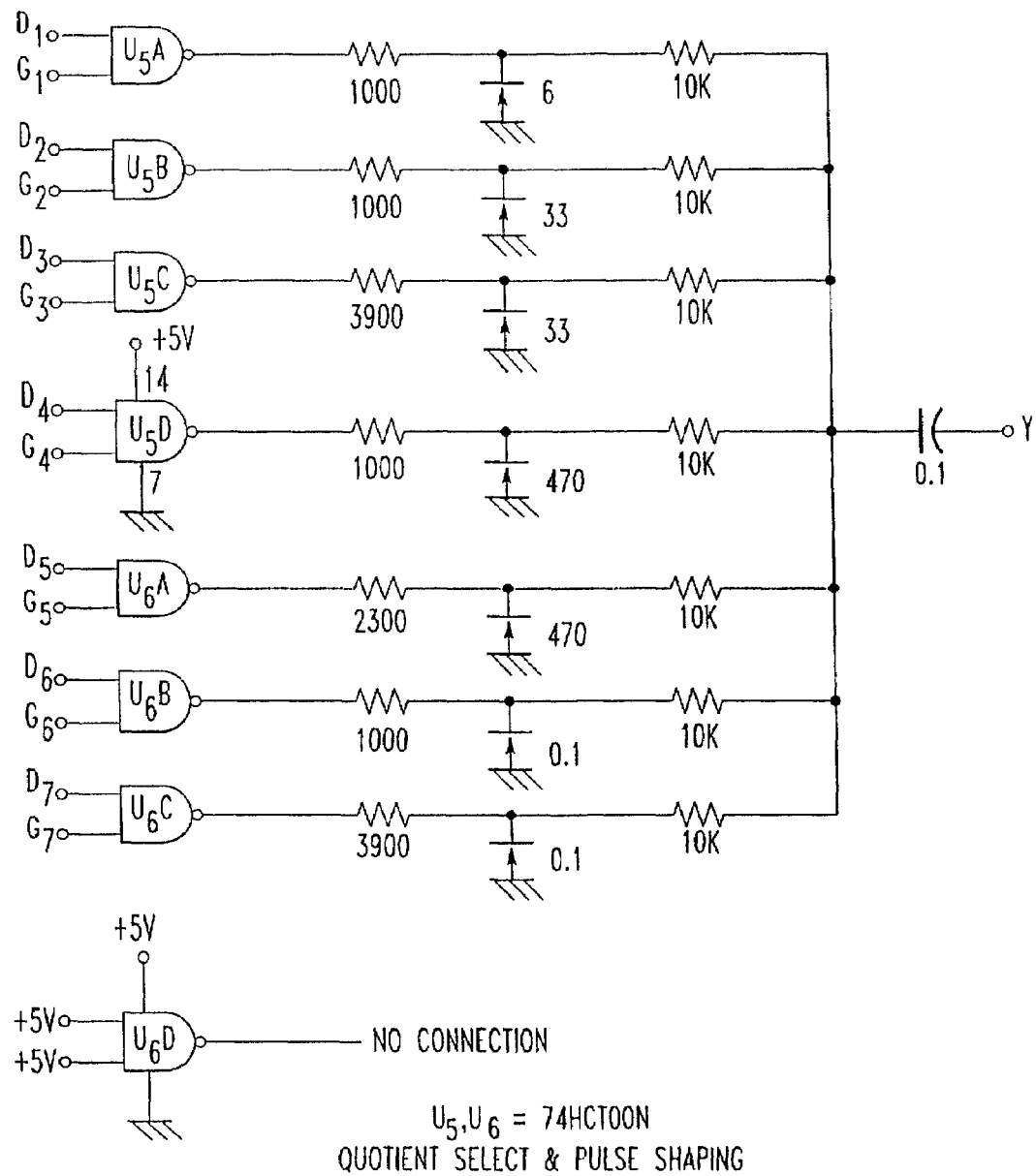
Figure 28:
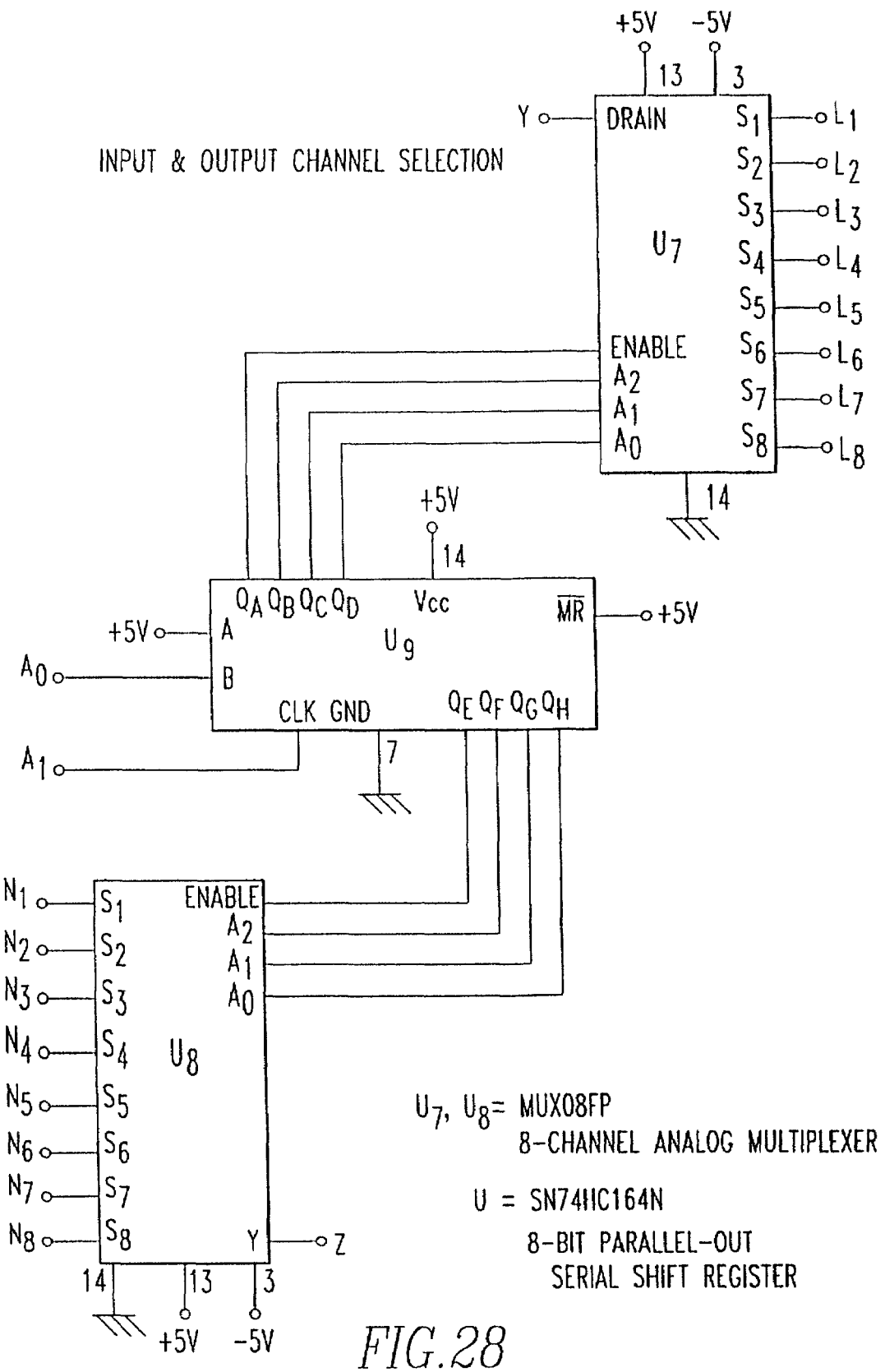
Figure 29:
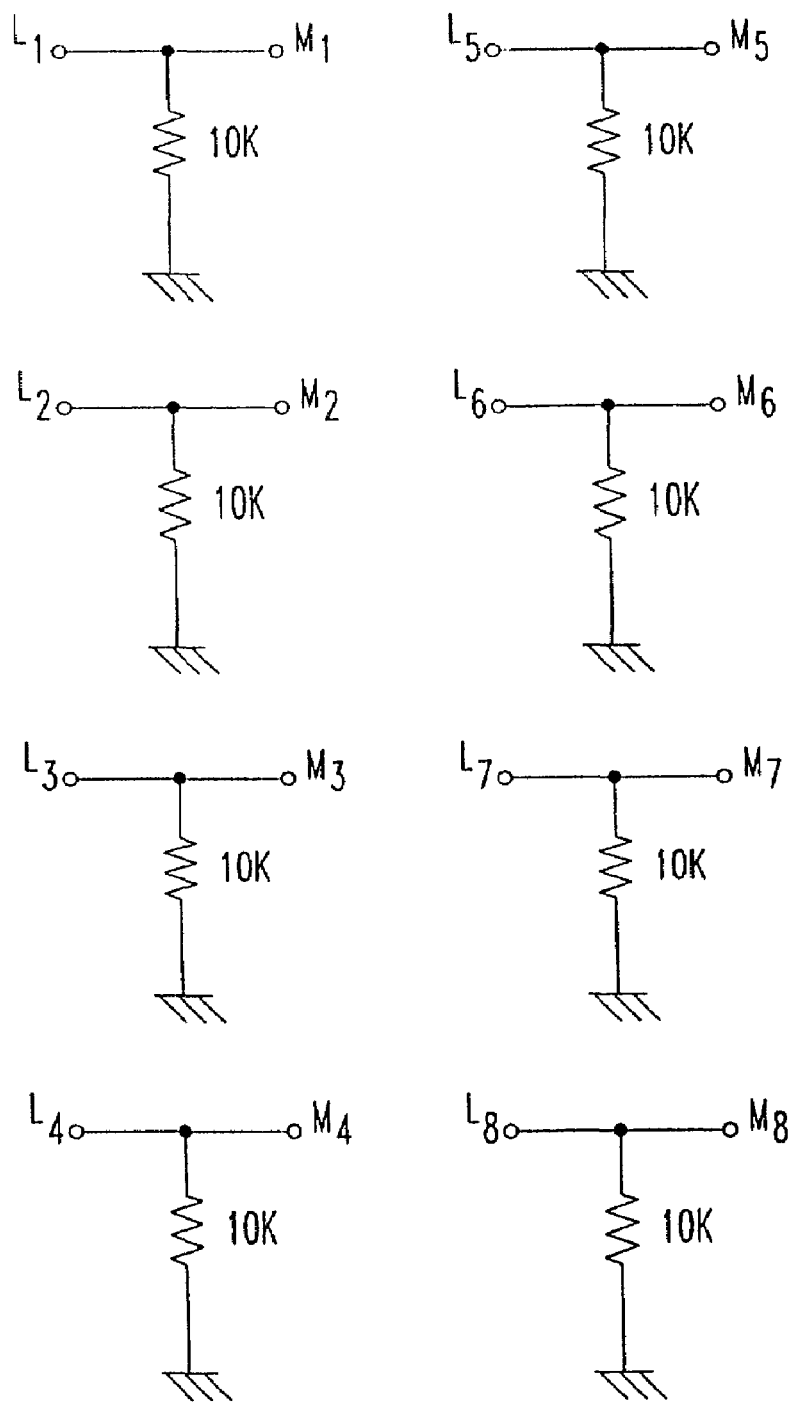
Figure 30:
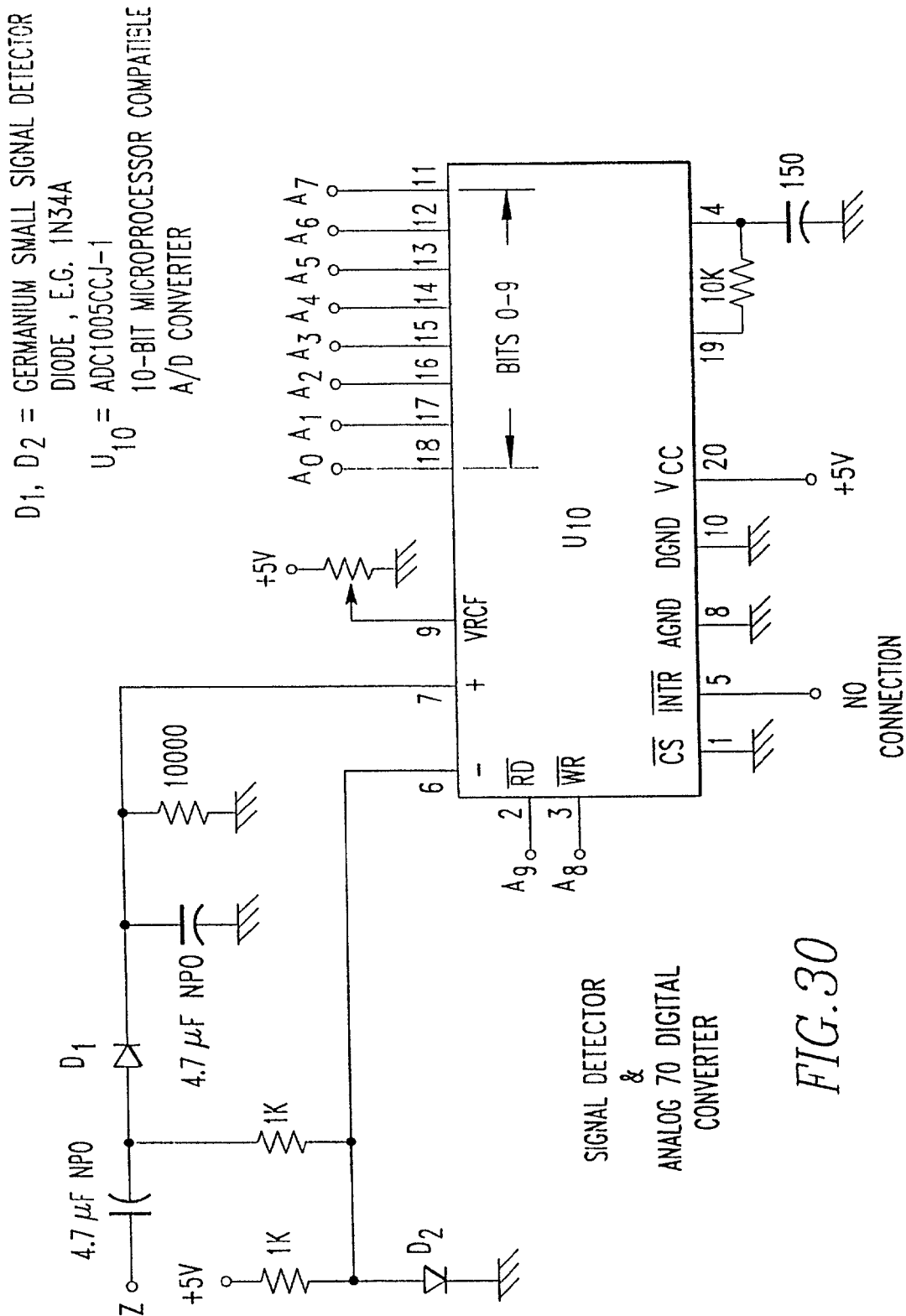
Figure 31:
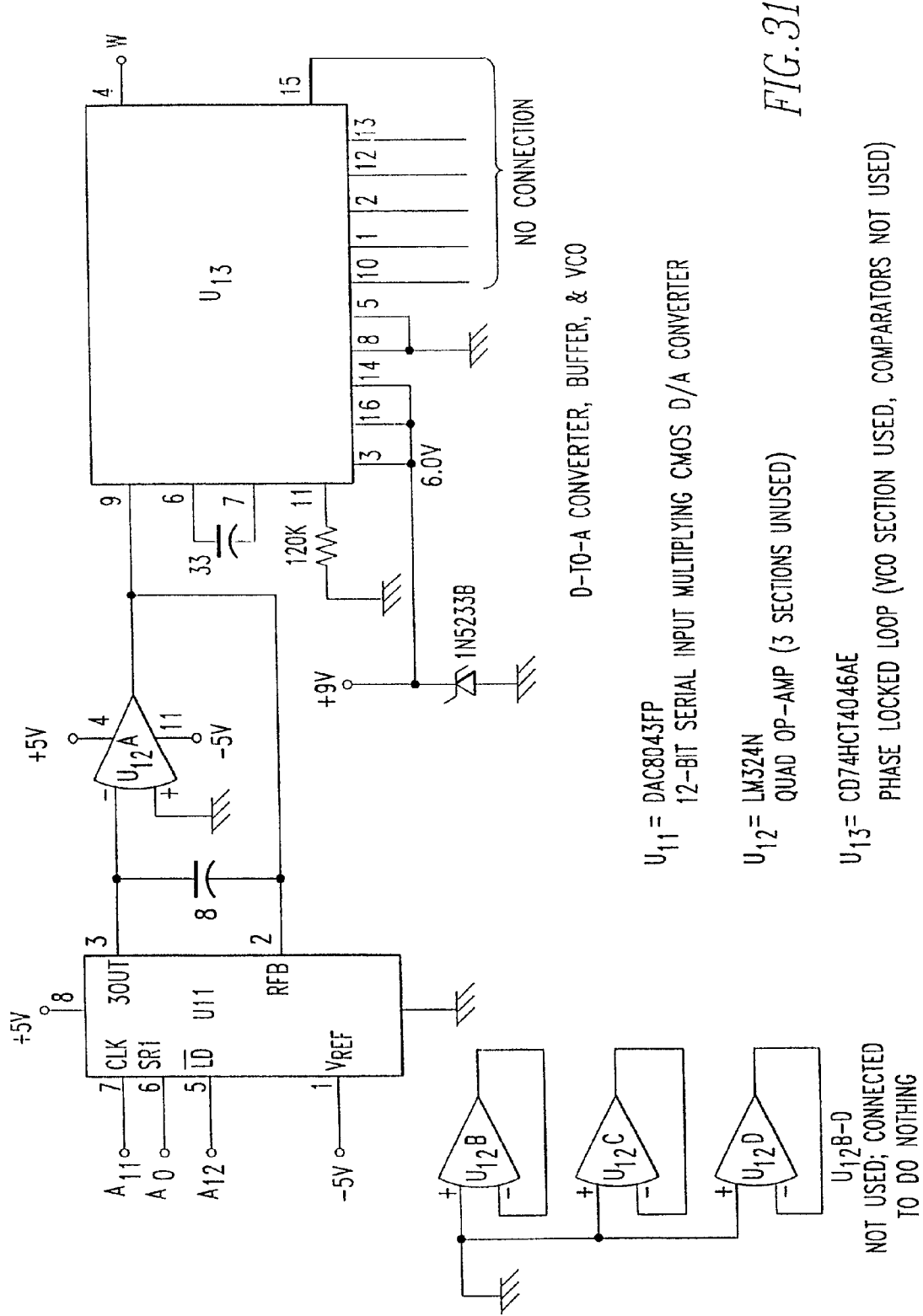
Figure 32:
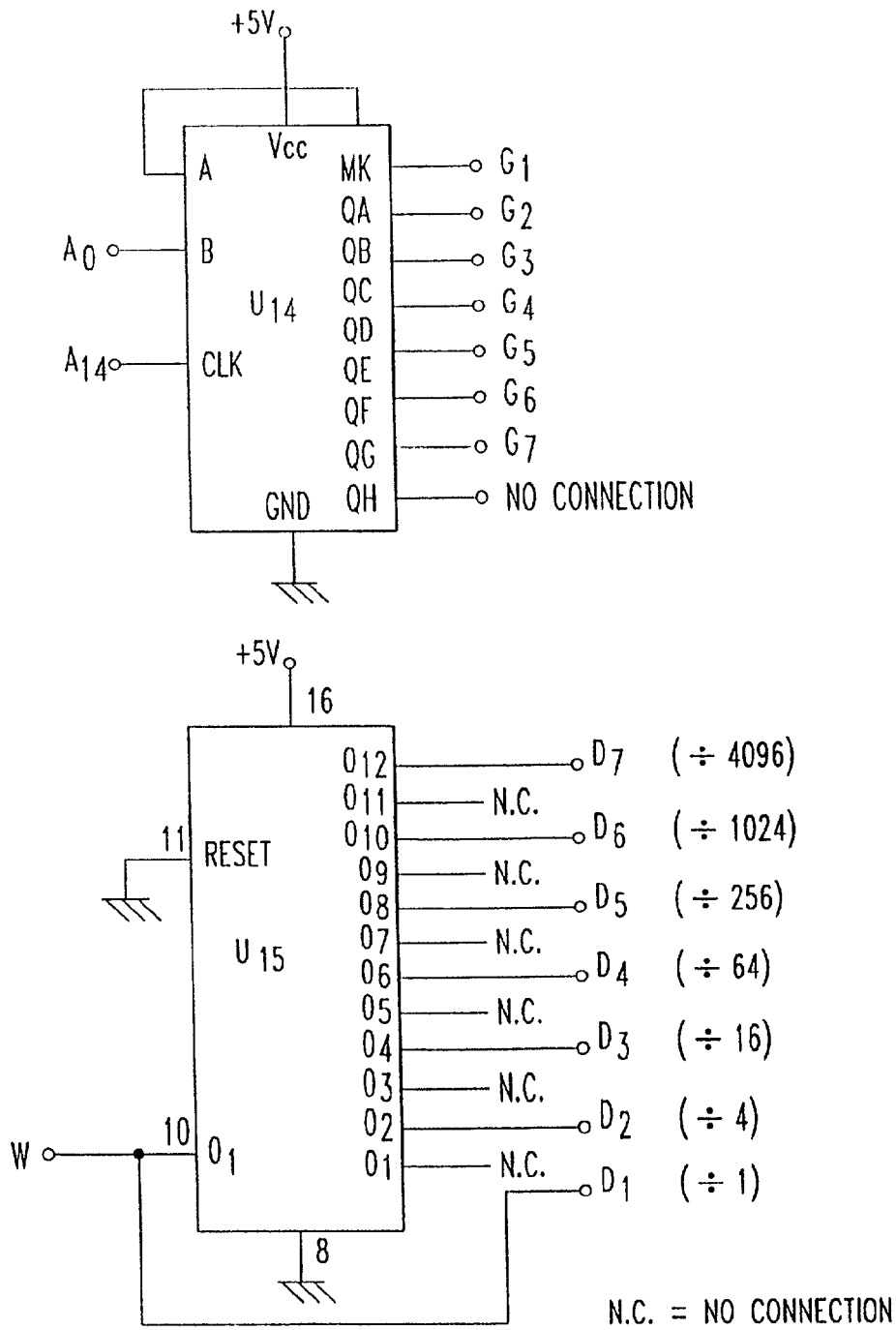
Figure 33:
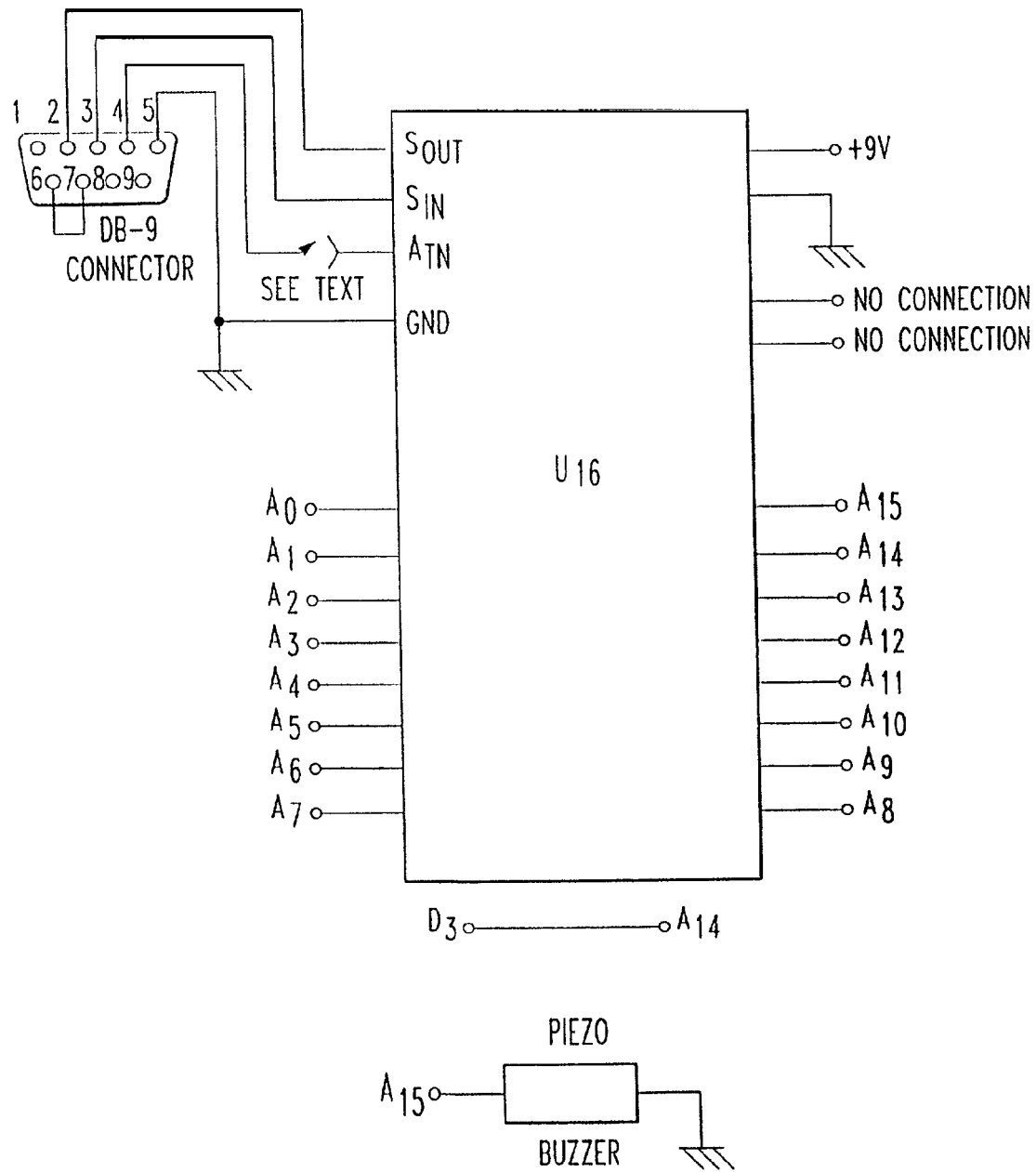

There are many ways this can be accomplished as described above. To summarize, these include but are not limited to the following. A contact technique which measures the electrical properties of the subject individual can be used. A contact technique which measures the magnetic properties of the subject organism can be used. A non-contact technique which measures the electric and/or magnetic properties using steady electrical and/or magnetic field interruption can be used, as shown in FIGS. 12, 13, 14 and 21. A non-contact technique which measures the electric/magnetic properties using induced currents from an electric or magnetic field can be used, as shown in FIGS. 15, 16, 17, 18, 20 and 22. A non-contact technique which measures the elecric/magnetic properties using steady electromagnetic field interruption can be used, as shown in FIG. 21. The non-contact method which measures the electric/magnetic properties by reflection of an electromagnetic field can be used, as shown in FIG. 22, and where only one field is detected as shown in FIG. 23. A non-contact technique which measures the electric/magnetic properties using induced current from an electromagnetic field can be used or an acoustic field as shown in FIGS. 67-71. These are but some examples of how electrical or magnetic properties of an individual can be determined for recognition purposes.

The present invention pertains to an apparatus for recognition of an individual living organism's identity. The apparatus comprises a sensing mechanism having a contact area of less than 2.0 centimeters squared to identify an attribute of the organism. The sensing mechanism produces a signal corresponding to the attribute. The apparatus comprises a mechanism for recognizing the organism from the attribute. The sensing mechanism is in communication with the recognizing mechanism so the recognizing mechanism receives the signal from the sensing mechanism. Preferably, the recognizing mechanism is in contact with the sensing mechanism. The contact area of the sensing mechanism is preferably less than 0.2 centimeters thick. In the preferred embodiment, a single acoustic transducer having about 1.5 $cm^2$ surface area was used to detect a biometric recognition pattern. The acoustic transducer surface is less than 2 mm in thickness.

FIG. 63 shows an actual size of a 1 cm diameter and 1.25 cm diameter thin electrode for sequential grasping between the thumb and fingers. FIG. 64 shows a cross-sectional view of the electrode. FIG. 65 shows a side view of the electrode.

FIG. 66 shows a flip-up sensor. This sensor can be only as thick as two pieces of metal foil and an insulator. It can be on a hinge so that it is flush with a surface until it is used. Then it is flipped up at right angles to the surface.

The present invention pertains to an apparatus for recognition of an individual living organism's identity. The apparatus comprises a sensing mechanism having a thickness of less than 0.2 centimeters to identify an attribute of the organism. The sensing mechanism produces a signal corresponding to the attribute. The apparatus comprises a mechanism for recognizing the organism from the attribute. The sensing mechanism is in communication with the recognizing mechanism so the recognizing mechanism receives the signal from the sensing mechanism.

The present invention pertains to an apparatus for recognition of an individual living organism's identity. The apparatus comprises a sensing mechanism for sensing an attribute of the organism. The sensing mechanism produces a signal corresponding to the attribute. The apparatus comprises a mechanism for recognizing the organism from the attribute with an accuracy of greater than one in a billion.

In the preferred embodiment, 9 out of 10 imposters can be eliminated with a single frequency scan. There are significant electric/magnetic pattern differences at least every 50 Hertz. Scanning from 50 Hertz up to 500,000 Hertz, yields 10,000 significant patterns. If a different 9 out of 10 imposters are eliminated at every different frequency, then an accuracy is attained of 1 in 1 times 10 to the 10,000 power of people. The entire world population is only 8 times 10 to the 9 power of people, rounding to 1 times 10 to the 10 power. Accordingly, an accuracy for 1,000 times the planet's population is attained. However, only a different 9 out of 10 imposters at 10 different frequencies are needed to be eliminated in order to be accurate for the entire world. The present invention is able to eliminate a different 9 out of 10 imposters for at least 25 different frequencies.

The present invent-on pertains to an apparatus for recognition of an individual living organism's identity. The apparatus comprises a sensing mechanism which is moldable into a shape having a non-flat surface. The sensing mechanism senses an attribute of the organism and produces a signal corresponding to the attribute. The apparatus comprises a mechanism for recognizing the organism from the attribute. The recognizing mechanism is in communication with the sensing mechanism. In the preferred embodiment, the sensing mechanism can be concave, flat, convex, or a combination thereof, lending them to molding into numerous devices. The sensing mechanism simply needs to contact the skin of subject individual. In a preferred embodiment, plastic piezoelectric material was used for the molded surface. Piezoelectric film sensors can be purchased from the AMP Piezo Film Sensor Unit in Valley Forge, Pa., incorporated by references herein. Alternatively, see "Piezocomposite Transducers—A milszone in ultrasonic testing" by G. Splitt, incorporated by reference herein. In addition, rigid acoustic transducers can be curved concave, or curved convex, or beveled or faceted surfaces can also be used.

The present invention pertains to an apparatus for recognition of an individual living organism's identity. The apparatus comprises a sensing mechanism which is flexible. The sensing mechanism senses an attribute of the organism and produces a signal corresponding to the attribute. The apparatus comprises a mechanism for recognizing the organism from the attribute. The recognizing mechanism is in communication with the sensing mechanism. In a preferred embodiment, an acoustic biometric sensor made of plastic-type piezoelectric material, as identified above, can be used which results in a flexible sensing mechanism.

Preferably, the sensing mechanism is made of rubber, plastic, metal, mineral or ceramic or composites. Because an electrode need only to be able to contact the skin of the subject individual, the electrode surface can be flexible. By being able to bend or compress, flexible electrodes can be built into a watch and its bands or jewelry or items of clothing, leather luggage or plastic credit cards without any affect on the functionality of the article being attached with the flexible electrode. For instance, there can be a plastic identity card with a name and picture, and a thumb electrode on one side and two or three finger electrodes on the other side. The card can be slid one quarter inch down into a reader and the electrodes grasped. The reader compares the pattern of the subject individual who is contacting the thumb electrode and two or three finger electrodes to the pattern stored on the card.

Referring to FIGS. 24-33, there are shown the circuit diagrams regarding a preferred embodiment of the apparatus for recognition that can be connected to sensors or electrodes. Except as indicated, all decimal capacitance values are in μF, and all whole-number capacitances are in pF. All resistances are in ohms.

The system contains a waveform-generation stage, a waveform-detection stage, and associated digital logic. The system allows up to 8 connections to a person for measurement.

The frequency range of the waveform-generation stage is approximately 75 Hz to 1.2 MHZ. To generate this signal, a voltage-controlled oscillator (U13) is used. The voltage used to tune the oscillator is generated by U11, a 12-bit D/A converter. This converter conveniently uses a serial input, so only 3 wires are required from the microcontroller to set the voltage output instead of the customary 12. The VCO tunes from approximately 300 kHz to 1.2 MHZ, a coverage range of approximately 1 to 4. Output from the VCO is approximately a square wave.

The VCO is fed into a 12-bit ripple counter, U15, in order to make lower frequencies available. The ripple counter is wired to divide the VCO output frequency by powers of 4; e.g., the output frequency is divided by 1, 4, 16, 64, 256, 1024, or 4096. One of these outputs is selected by quad NAND gates U5 and U6. Each possible divisor is assigned to one input of its own NAND gate. The other input from each gate is set by the microcontroller to enable the correct divisor only. As the microcontroller has a limited number of pins, an 8-bit parallel output serial shift register, U14, is used to reduce the number of connections required from 7 to 2 by allowing the NAND gate mask to be transmitted serially from the microcontroller.

As the D/A and VCO sections may exhibit some frequency drift over time, one of the divider outputs is connected to one of the microcontroller I/O pins. This permits the microcontroller, which contains a time reference which is locked to a ceramic resonator, to determine the actual VCO frequency for calibration purposes. The accuracy of this determination is limited by the resonator's tolerance and is 1% or better.

The outputs of the NAND gates are shaped with RC filters to limit the spectrum of the output waveform to what is intended. As square waves contain a very high-frequency component as the tire of each state transition, the wave shapes are modified so that they are somewhat rounded. This ensures that the frequency being measured by the waveform-measurement stage is the frequency which was intended for measurement.

After the RC filters, the frequency-divided outputs are summed to a common point and passed through a capacitor to remove the DC bias. Note that only one output should be transmitted at a time (although it is possible to program the microprocessor to output multiple frequencies, this is not normal operation). The signal is fed, with the DC bias removed, to a CMOS analog multiplexer, U7, to distribute the signal to a point on the subject's hand; e.g., a finger or the wrist. The signal at this stage is approximately 1 volt peak to peak. U7, by the way, takes its address and enable inputs from another parallel output serial shift register, U9, for the same reasons that U14 is present elsewhere.

The waveform-measurement stage begins with a set of eight input amplifiers based on the LT1058 quad JFET input precision high-speed op-amp (U3, U4). Its pin-compatible with many other quad op-amps including the LM324. The LM324 cuts off around 20 kHz, and response past 1 MHZ is needed. The voltage gain is set at 2:1 but can be adjusted by altering resistor values. The issue is ensuring that sensitivity is adequate without overloading the analog MUX inputs on U8. Remember that the full output of the waveform-generation stage will be on one of the MUX pins, while the low level at another pin is being routed to the detector.

The CMOS analog multiplexor, U8, is used to route the signal from the appropriate hand connection (e.g., finger or wrist) to the detector. The address and enable inputs for this MUX also come from U9.

A half-wave diode detector is used to rectify the AF or RF signal and provide a DC level which is usable by the A/D converter. Because the diode has a forward voltage drop of around 0.3 V, a 0.3 V bias voltage is used to keep the diode at the threshold of conduction for small signal detection. The bias voltage is generated by reference to an identical diode.

The A/D converter, U10, is microprocessor compatible meaning that its outputs can be switched to high impedance. This permits the same connections to be used for other purposes. Of the eight output pins, seven are dedicated to the A/D converter, but one doubles as the data pin for the serial input chips, U9, U11, and U14. This works because the microcontroller lines are bidirectional, and the serial input chips are not clocked during A/D transfers to the microcontroller. To further complicate things, the ten A/D output bits are stuffed into eight wires, meaning two wires are used to read two bits each. This is accomplished by initiating two read cycles from the microcontroller.

The microcontroller, U16, is a BASIC Stamp II from Parallax, Inc. It has a built-in serial interface with a line receiver, "fakes" a line transmitter with a resister (works for most computers, but some might have trouble as the logic levels aren't standard-see the documentation from Parallax), 16 I/O lines, 26 bytes RAM, 2048 bytes EEPROM, and a BASIC interpreter in ROM. The controller is very easy to use and programs in a BASIC dialect. It should be noted: pin 3 of U16 must be connected when programming the microcontroller, but must be disconnected immediately after programming and prior to use. This disconnection is shown on FIG. 33.

To read an impedance, the following steps must be performed by the microcontroller. This is generally in communication with a host computer such as a notebook computer running Windows 98 and appropriate software. The microcontroller software is already written, and serves to accept commands from the host computer and return readings as appropriate.

1. Set the D/A converter to output a voltage which causes the VCO to oscillate at the desired frequency. This is within a range of 300 kHz to 1.2 MHZ. This step is performed by sending a 12-bit signal to the D/A converter via the 3-wire serial interface A0, A11, and A12.
2. The frequency output by the VCO should be measurer by counting the pulses on the appropriate microcontroller pin (A13) over a fixed period of time. The D/A converter output can be adjusted as necessary to ensure that the correct frequency is produced.
   (This step can be done either in real time, or more preferably as a pre-operation sequence to produce a frequency calibration curve. The unit will not drift appreciably during a usage session, but might over weeks or months. It also requires this frequency calibration prior to being placed in service. This step can be entirely user-transparent.)
3. The input and output MUX channels (fingers or wrist) must be selected. This is done by sending an 8-bit signal to U9 via the 2-wire serial interface A0 and A10.
4. The appropriate frequency divider output (1, 4, 16, 64, 256, 1024, or 4096) must be selected. This is done by sending an 8-bit signal (7 bits are used) to U14 via the 2-wire serial interface A0 and A14.
5. A brief settling time (10 ms is adequate) should occur to allow the capacitor in the signal detector to reach equilibrium with the new measured value.
6. The A/D converter is read. This is accomplished using A0 through A7 for data, A8 and A9 for control. The chip is actually read twice to obtain all ten bits of the result; refer to the manufacturer's documentation. Do not forget to set A0 as an input pin for this step; it is used at other times as an output pin for serial data.

The data read by the A/D converter will require numeric adjustment via some calibration curve to represent an actual impedance. This curve will be sensitive to frequency on account of the RC filters and frequency response of the input amplifiers, MUK, and signal detector circuit. A "calibration plug" with fixed impedances in place of a handpiece has been fabricated to allow the system to produce calibration curves for this purpose.
7. A15 is connected to a piezo buzzer to allow the microcontroller to make appropriate noises as desired by the programmer. Alternatively, A15 may be used to drive a small speaker through appropriate circuitry-the microcontroller can generate as many as two audio frequencies at a time on this pin using pulse width modulation.

For a discussion regarding transducers and acoustics generally, see "Encyclopedia of Acoustics" by Malcolm J. Crocker, John W. Ley & Sons, Inc., incorporated by reference herein.

There are various embodiments for biometric units such as hand units 125 that are used for recognition purposes. These hand units can be used as a key to start or allow access to a computer, vehicle or other object. A signature signal is sent by wiring, or by transmission, to a computer. The computer processes the signal and either compares it to a known signature signal of the organism already stored in the computer's memory, or prepares it for further transmission to a remote location, or both. Alternatively, instead of simply allowing access or activating a computer once recognition is attained, a constant signal of the person holding or operating the hand unit, mouse or the keyboard can be sent from the computer through a modem either directly to a remote party or through the Internet to assure the party at the remote site that the person at the keyboard or mouse who is in communication with the remote party, is the desired person. In this latter scenario, the assurance is then maintained over time that the person who has the proper recognition to activate the computer does not then turn the control of the computer over to a third party who does not otherwise have access to the computer, and appropriate the computer for subsequent operations under the authorized persons name, such as sending or obtaining information or purchasing goods or services from a remote location which requires the identity of the authorized person. The computer can also keep a log of who accessed a site and when.

Generally, six electrodes are used for hand units. All connections are made through the 9 pin connector that is standard on the back of a computer tower or desktop, although the 25 pin printer port can also be used. The pins used on the 9 pin connector are the same ones for each hand unit. The electrodes can be conductive metallic foil, plastic, or rubber. They can be flat (about 2 centimeters times 2 centimeters) or molded for finger tips (taking into account the large variations in size). For a simple hand unit that will be used for recognition, a flat reversible hand unit can be used for the right or left hand as shown in FIGS. 34 and 35. Electrodes are placed in the following regions: 1) heel of the palm (a long electrode strip or a single small electrode movable on a spring); 2) thumb tip; 3) index finger tip; 4) middle finger tip; 5) ring finger tip; 6) little finger. The hand unit must be adaptable for large or small hands. It is made out of clear plexiglass for each surface. There is a hollowed out area for the heel of the palm to fit into, and also for the finger tips. The entire hand area could be hollowed out a little to produce more consistent hand placement. The hand piece is fabricated using brass inserts pressed through plastic sheets for the electrodes.

In regard to a keyboard 126 as shown in FIG. 36, electrodes can be placed at the (t), (7), (9), (p) keys and a 4 centimeter strip can be placed on the left end of the space-bar and a palm strip on the lower frame of the keyboard. Conductive rubber keys for the keyboard, at least at these locations, would be preferred. This embodiment on a keyboard would be appropriate for activation as opposed to continuous indication of the presence of an authorized user, since the user would not be able to maintain contact with all the electrodes continuously. The wiring from the electrodes on the keyboard can run with the normal keyboard wiring to the computer, or to the 9-pin or 25-pin connections.

Figure 37:
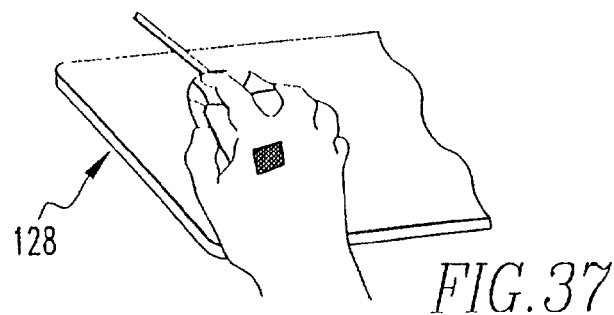
FIG. 37 is a schematic representation of a hand grasping a mouse having electrodes.
Figure 38:
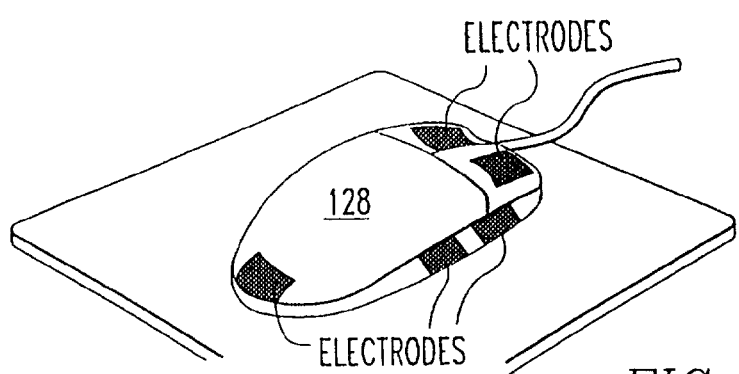
FIG. 38 is a schematic representation of a mouse having electrodes.

A mouse 128, as shown in FIGS. 37 and 38 could also be prepared for recognition. Conductive foil strips or imbedded conductive polymers that attach flat to the surface of the mouse for the palm and each finger tip would allow easy grasping over time of the mouse. A variation of requiring the user to continually hold the mouse along the foil strips can be established, where a time period exists which requires the user to grip the mouse at least once during each time period so the computer is not shut off. The keyboard and mouse preferably use Compac aluminized tape with conductive adhesive for the electrodes. The wiring from the electrodes on the mouse can run with the normal keyboard wiring to the computer, or to the 9-pin or 25-pin connections.

Figure 39:
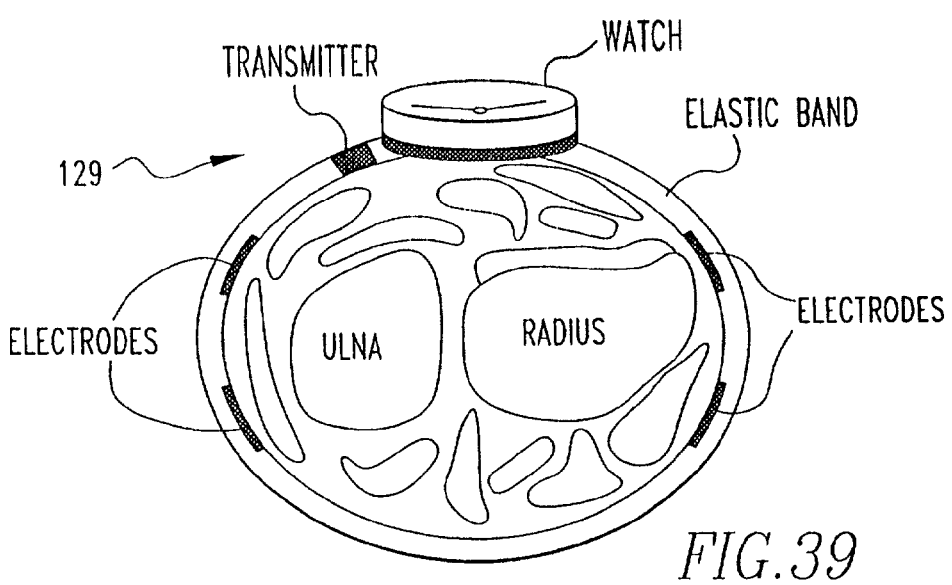
FIG. 39 is a side view of a wrist band having electrodes.

A wrist band 129, as shown in FIG. 39, made of elastic material can be used to simulate a wrist watch. Electrodes can be conductive foil attached to the inside of the band. A transmitter of the wrist band can transmit the individual's signature obtained with the electrodes by the push of a transmission button or by periodic automatic transmission. The transmission of the signature will then be received by a device that will have or has access to the person's known signature, and recognition will then be confirmed or denied for whatever the application or purpose. For instance, the watch can be activated by proximity to a wall unit. The wall unit recognizes the watch and gives entry. For this, the wall unit would recognize the watch on the person. Basically, the whole transmission is proximity detected. The watch has a transmitter and receiver. The wall unit emits a radio signal which is received by the receiver of the watch, causing the watch to transmit the biometric signal. The wall unit receiver receives it and compares it with known authorized signatures. If a match occurs, the wall unit allows current to flow to a lock mechanism in the door, disengaging the door lock so the door can be opened. The wrist band could be used with a personal area network, see "Personal Area Networks: Near-Field Intrabody Communicaion" by T. G. Zimmerman, Systems Journal, Vol. 35, No. 314, 1996, MIT Media Lab, incorporated by reference herein.

Figure 40:
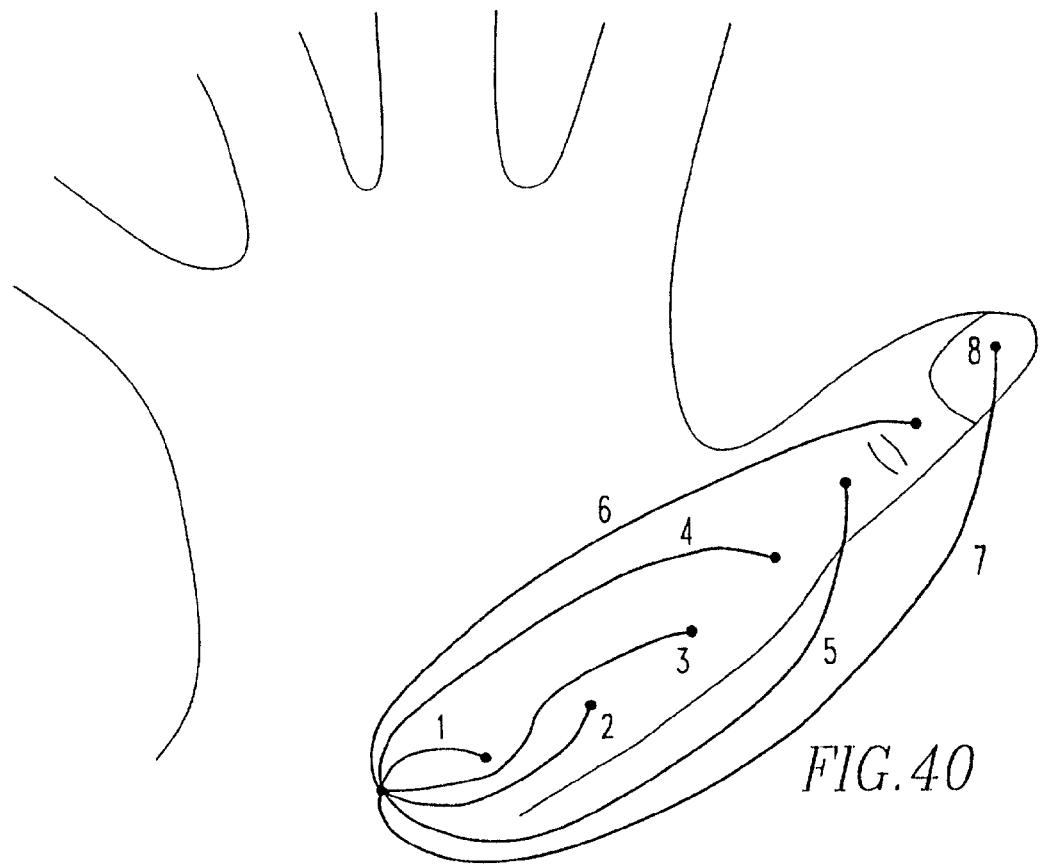
FIG. 40 is a schematic representation of electrode placement and current path of measurement from the palm to the thumb.
Figure 41:
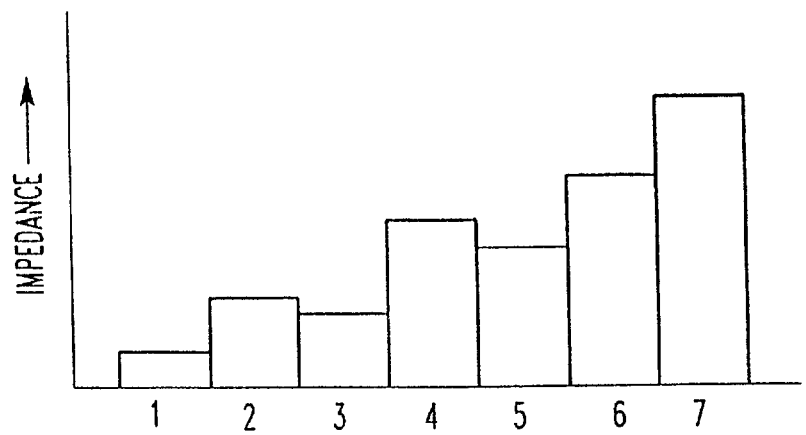
FIG. 41 is a two-dimensional impedance plot corresponding to the electrode placement of FIG. 40.
Figure 42:
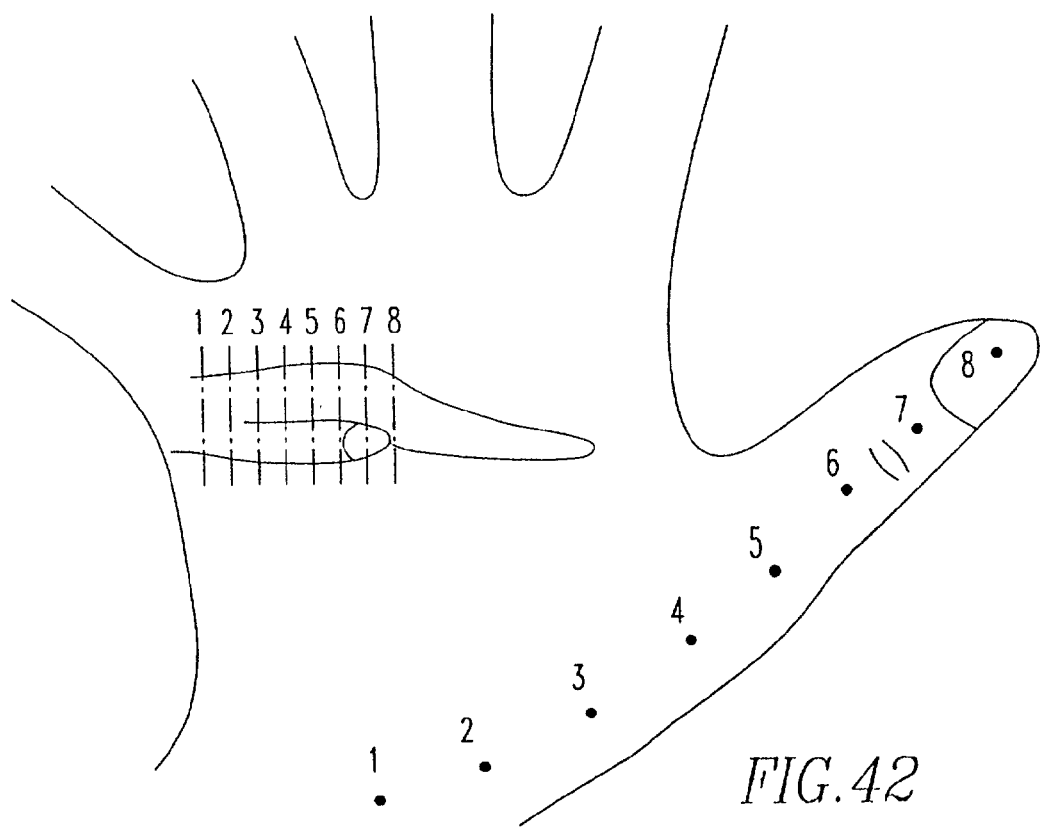
FIG. 42 is a schematic representation of measurement sites for back to front capacitive plate measurements from he palm to the thumb.
Figure 43:
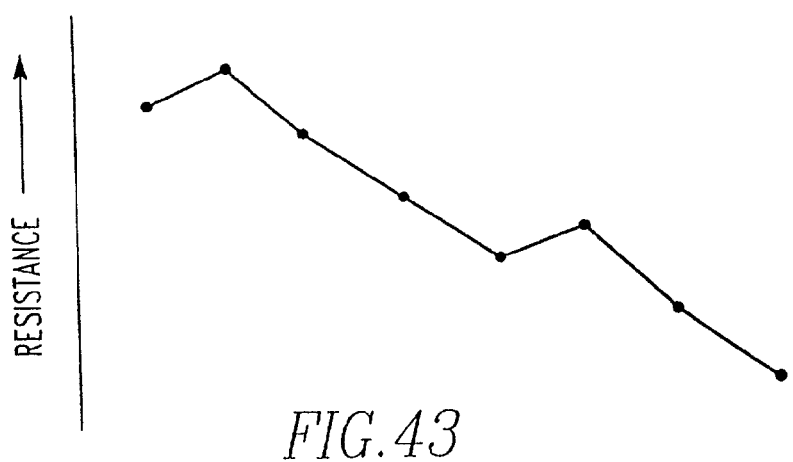
FIG. 43 is a two dimensional impedance plot regarding resistance at a single frequency corresponding to the measurement sites of FIG. 42.
Figure 44:
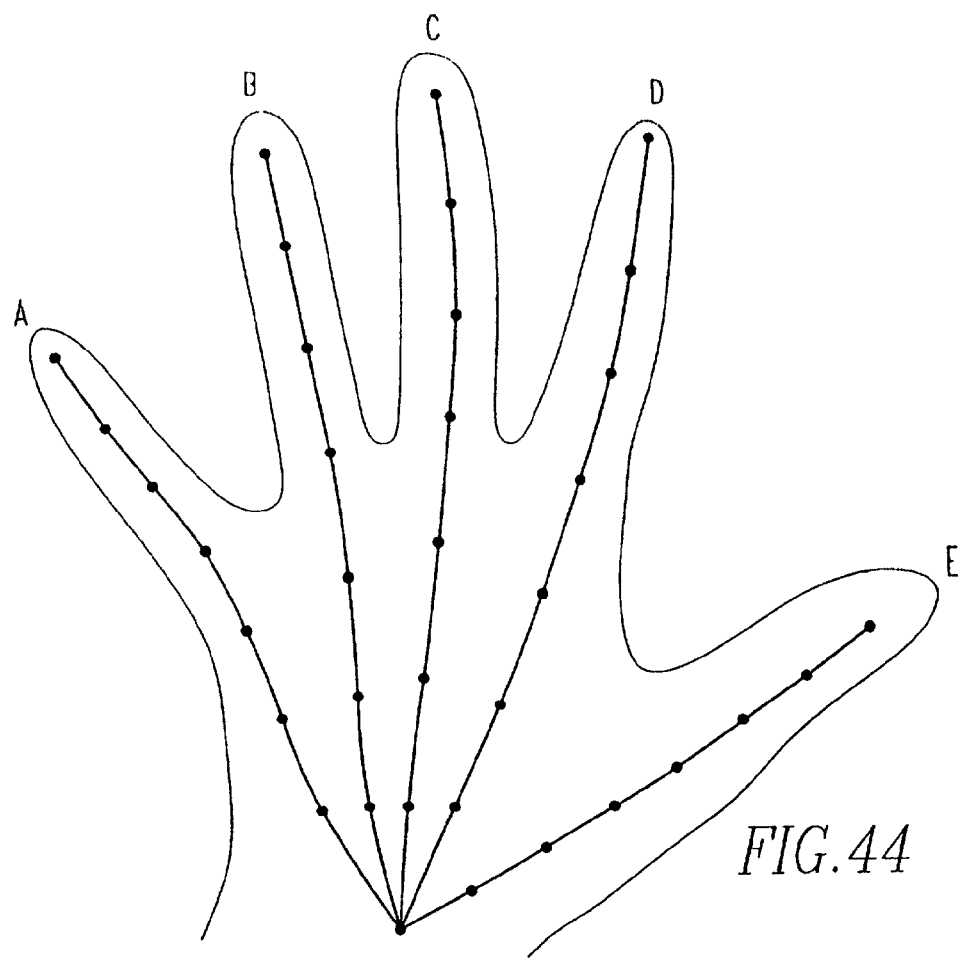
FIG. 44 is a schematic representation of measurement sites from the palm to each finger-tip.
Figure 45:
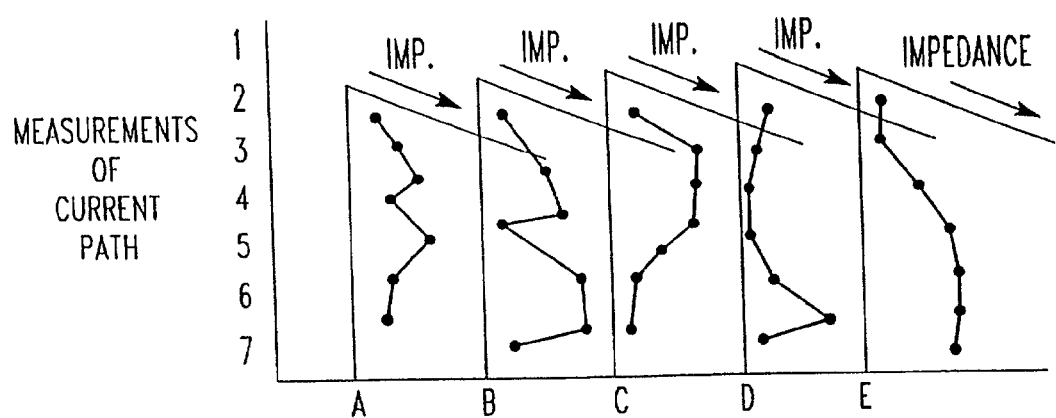
FIG. 45 is a three-dimensional plot at a single frequency regarding measurements from the measurement sites of FIG. 44.
Figure 46:
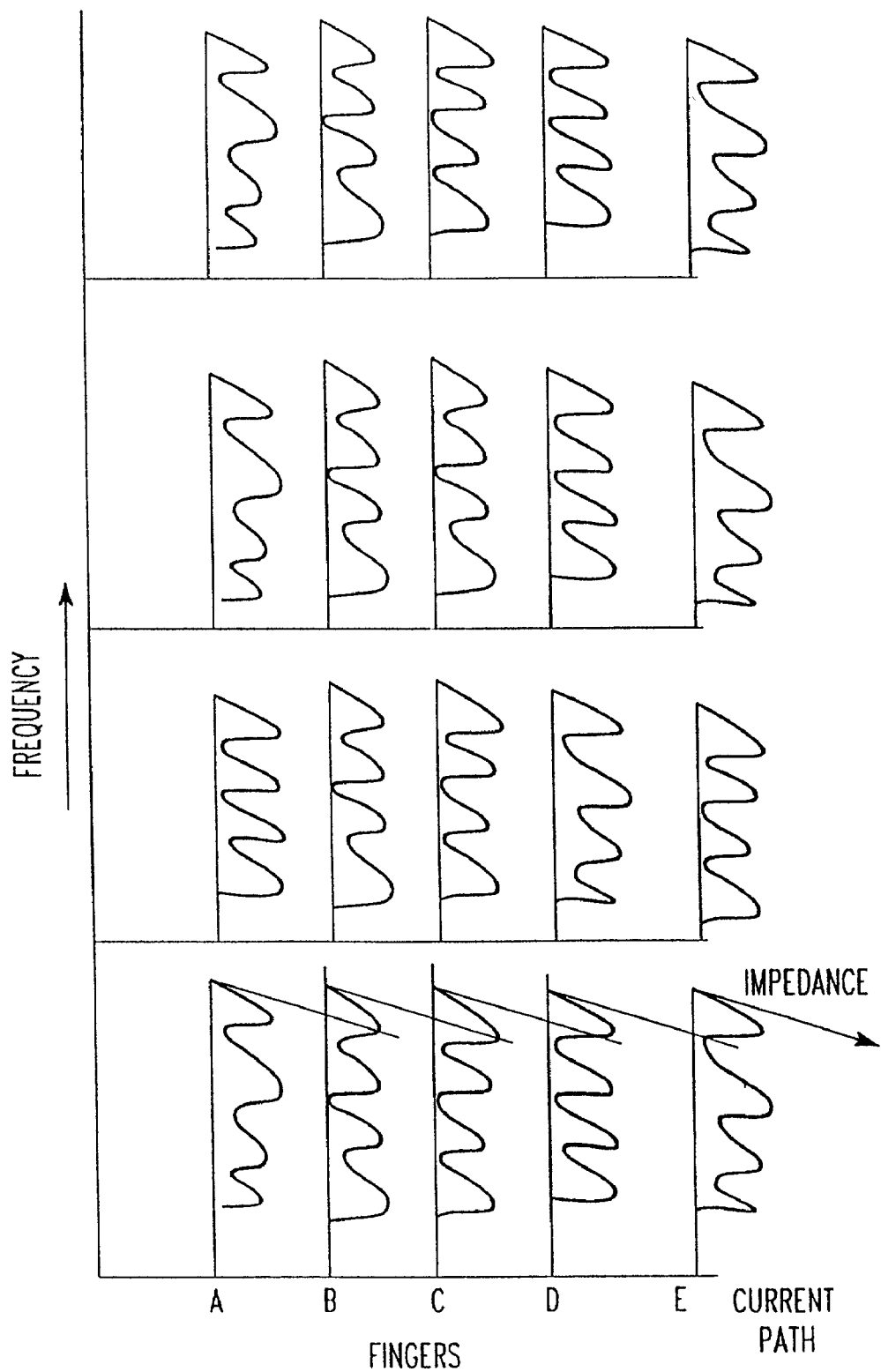
FIG. 46 is a four-dimensional plot at four different frequencies from the palm to each finger-tip.
Figure 47:
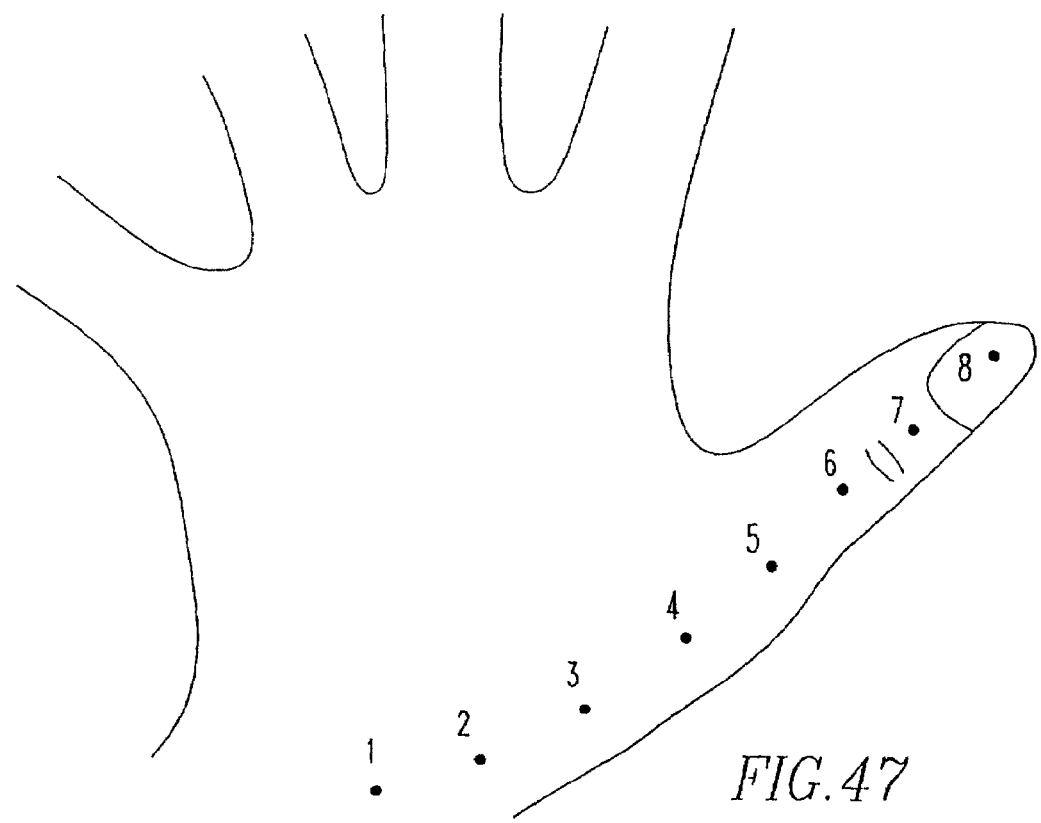
FIG. 47 is a schematic representation of electrodes for one finger.
Figure 48:
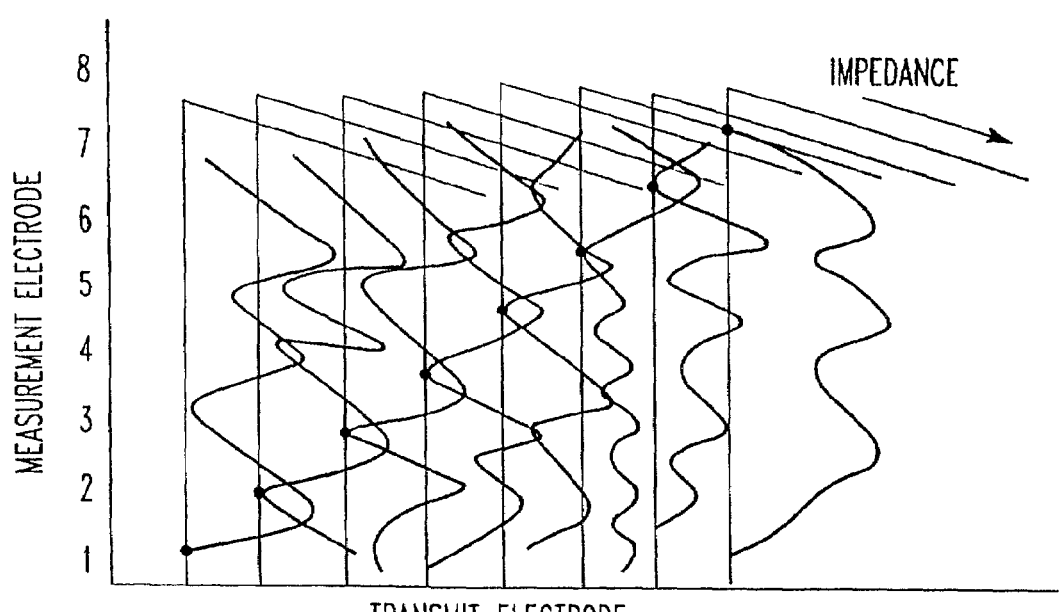
FIG. 48 is a three-dimensional plot at a single frequency from electrode to electrode for one finger as shown in FIG. 47.
Figure 49:
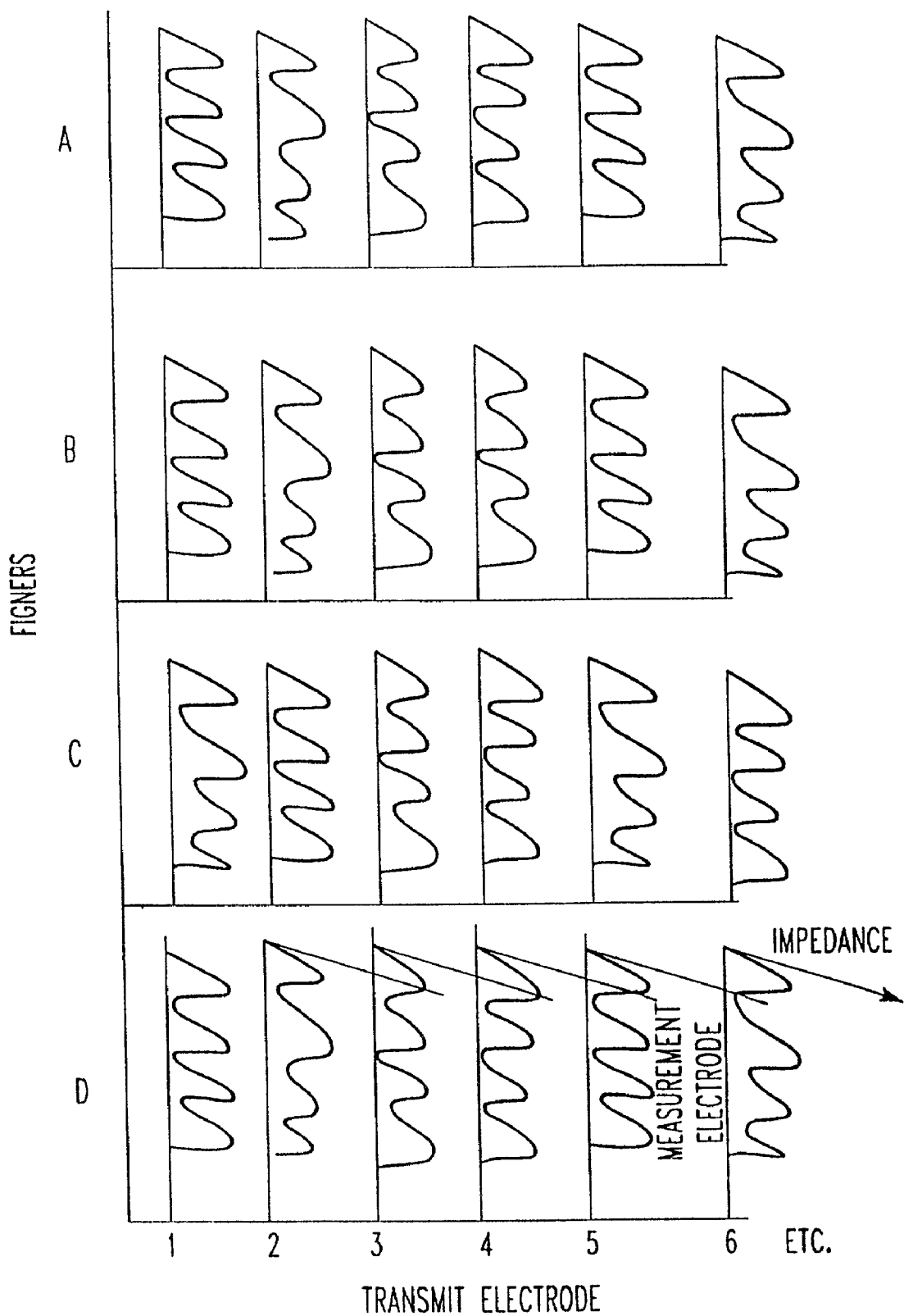
FIG. 49 is a four-dimensional plot at a single frequency from electrode to electrode for each finger.
Figure 55:
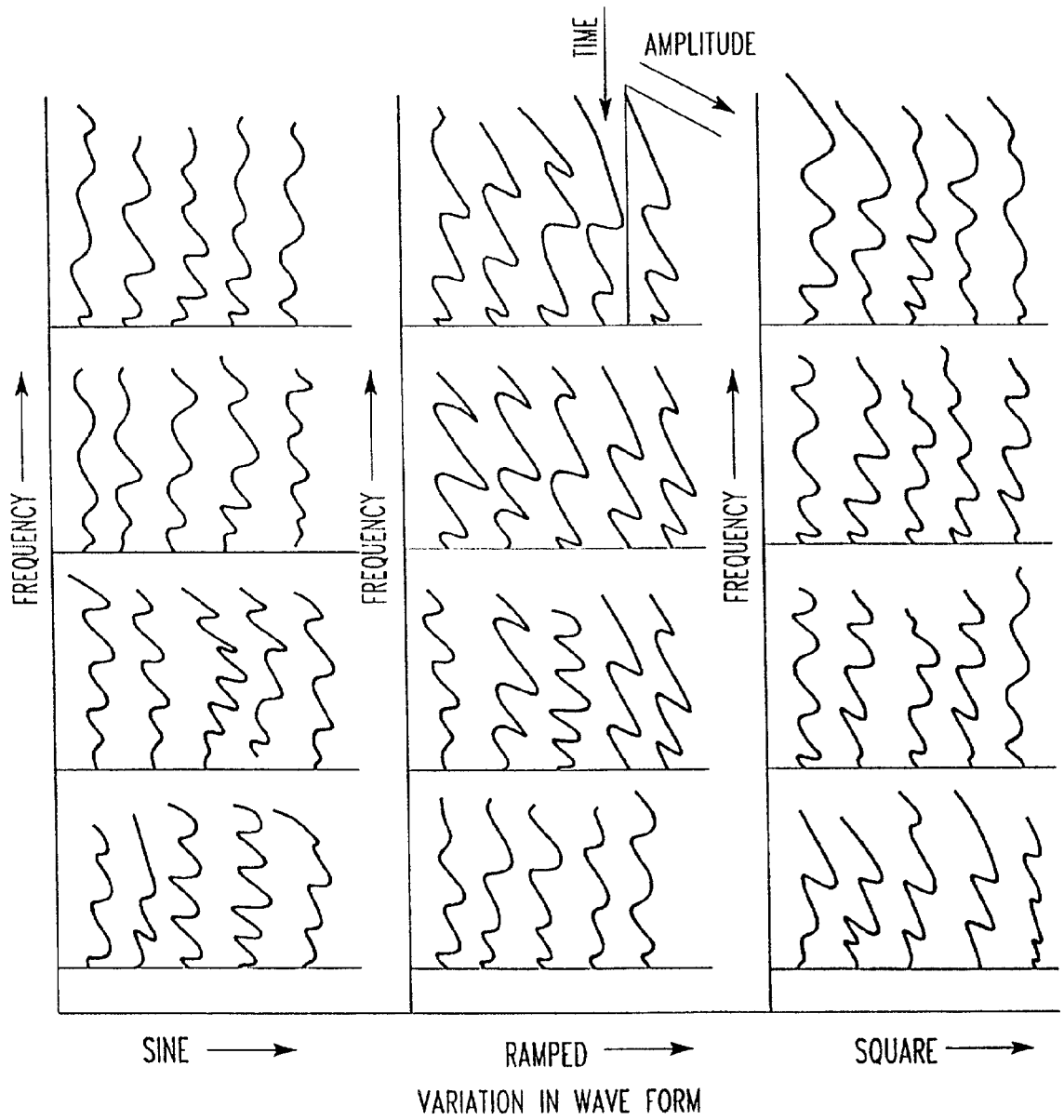
FIG. 55 is a five-dimensional plot with sine, square and ramped waveforms at four different frequencies through the side, center and other side of the thumb.
Figure 56:
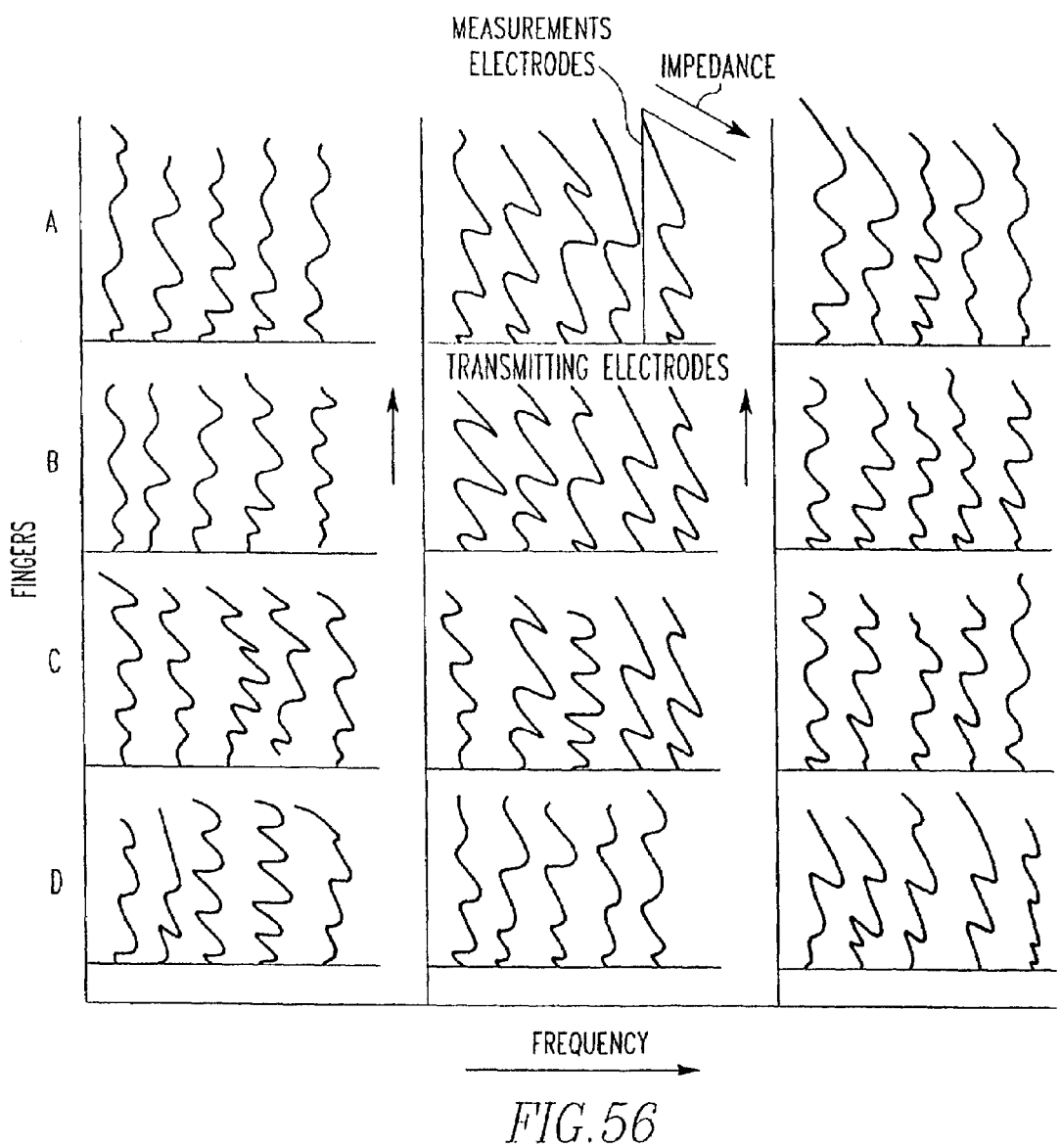
FIG. 56 is a five-dimensional plot at three different frequencies from electrode to electrode for each finger.
Figure 57:
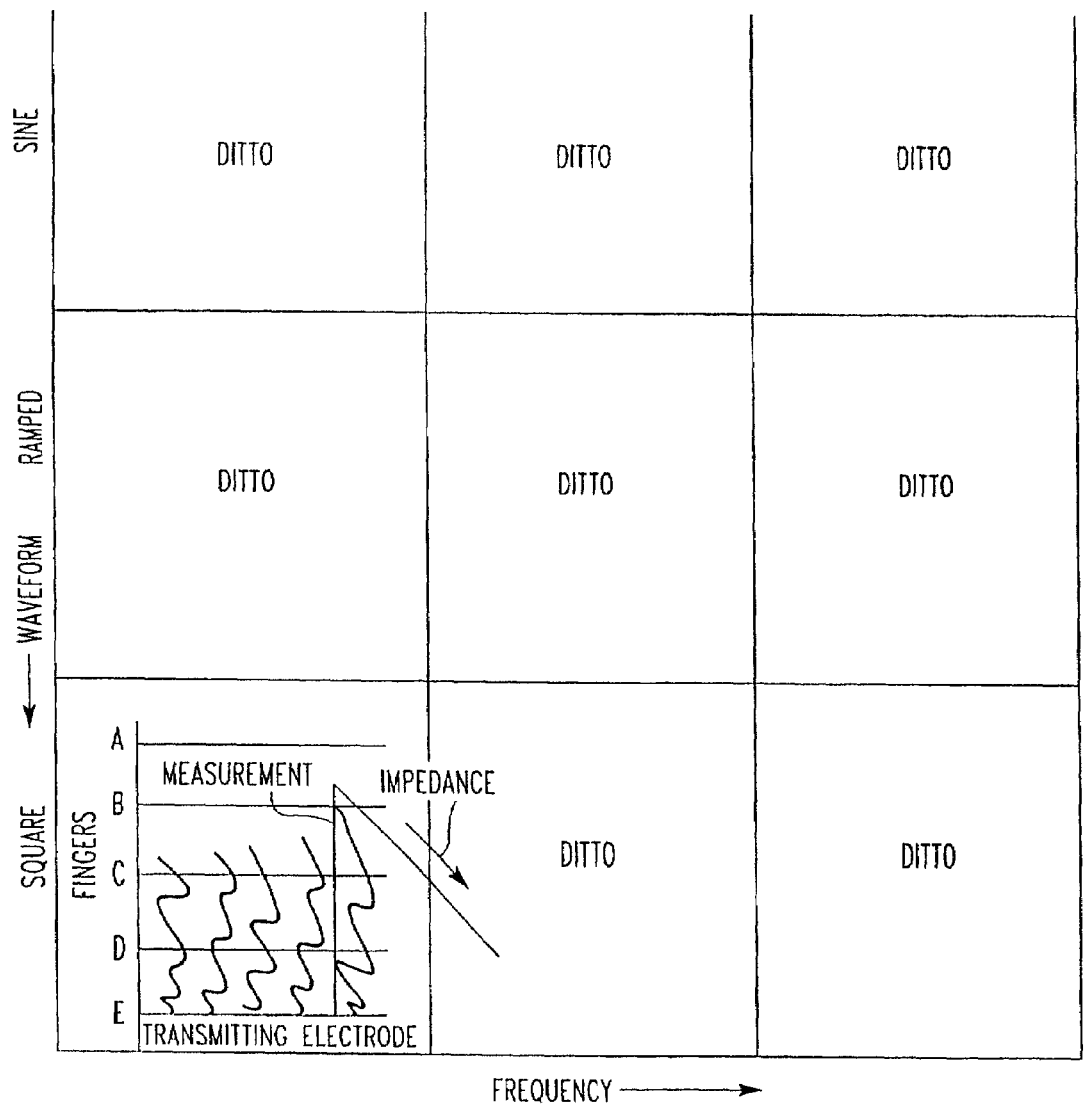

In a preferred embodiment, and referring to FIGS. 40-58, multidimensional matrices such as three and four dimensional matrices are formed for recognition purposes. Acoustic biometric scans can produce three-dimensional patterns at one frequency, and four-dimensional patterns at multiple frequencies. The electric/magnetic techniques described herein produced two-dimensional scans at a single frequency and three-dimensional matrices when multiple frequencies are used in regard to a single segment of the subject organism. In the electric/magnetic techniques, if there are multiple sensors along the current path, such as shown in FIGS. 40, 42 and 44 there would be for instance 8 different readings for the palm to thumb-tip current, at one frequency. That would produce a two-dimensional reading for the thumb and a three-dimensional plot for all five fingers. Extending this to multiple frequencies would yield a four-dimensional plot of the subject organism, as shown in FIGS. 46 and 49. By varying the waveform and switching patterns, five and six-dimensional matrices as shown in FIGS. 56-58 are attained.

Figure 50:
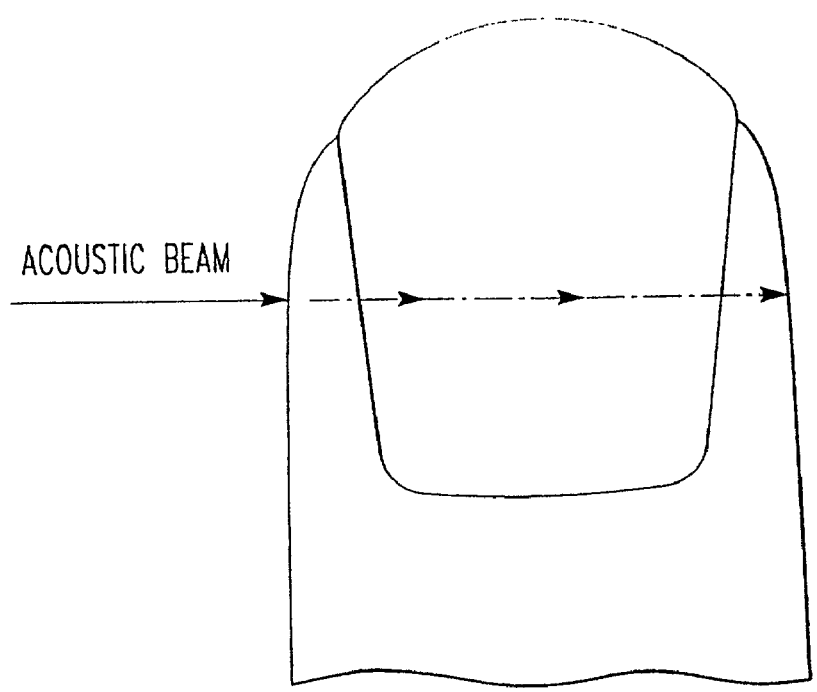
FIG. 50 is a schematic representation of an acoustic beam at a single frequency passing through the thumb from the side of the thumb.
Figure 51:
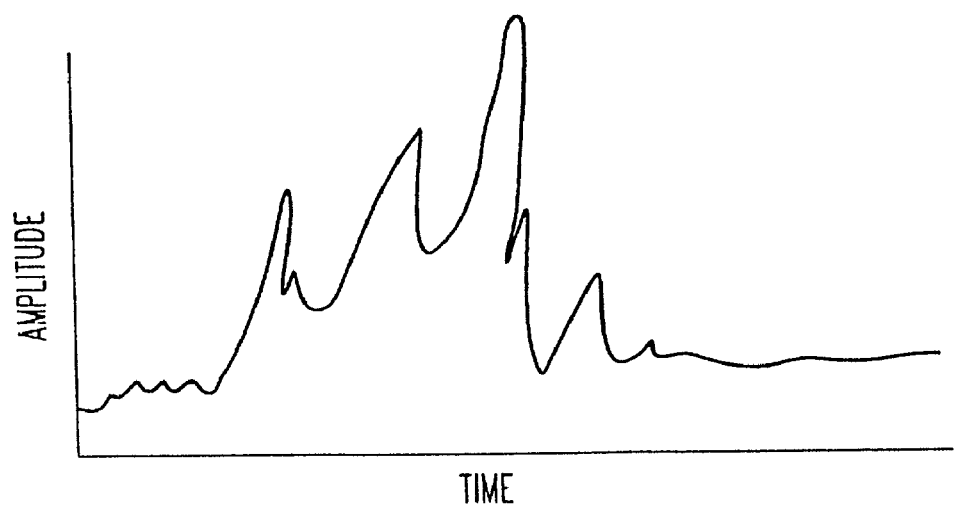
FIG. 51 is a two-dimensional acoustic plot at a single frequency regarding FIG. 50 where the plot is of amplitude versus time.

Scans on the thumb of several people all at a single frequency resulted in unique signatures corresponding with the individuals which allowed for easy identification of the individuals. For a single frequency scan, in its simplest form, a two-dimensional plot was obtained, with amplitude on the Y axis, and time on the x axis as shown in FIGS. 50 and 51. For a multiple frequency scan, a three-dimensional plot was obtained with frequency on the Z axis. The mode that was used to obtain the result was the "radar" type mode, with a single transducer working in what is known as the "pulse-echo mode". Preferably, only one transducer was used and excellent results were achieved, although more than one transducer could have been used.

In the radar type mode, the acoustic energy was transmitted by the single transducer in contact with the skin of the subject organism. The acoustic energy was released essentially in a well defined short burst and as the energy passed through the subject organism, portions of it over time were reflected as the energy moved through the soft and hard tissue of the subject organism. The echo or reflection of the energy back to the transducer over time yielded the signature of the subject organism.

Figure 54:
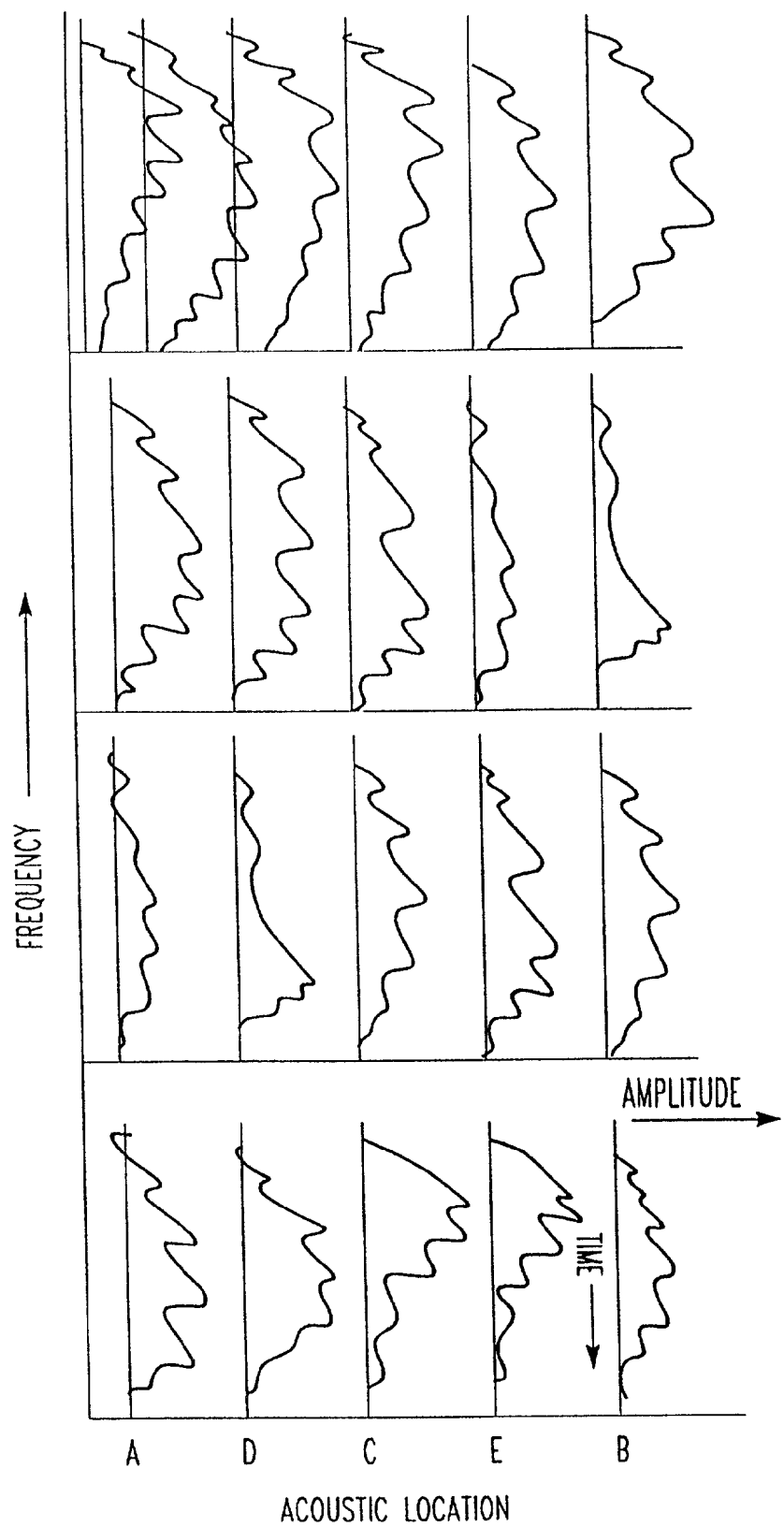
FIG. 54 is a four-dimensional plot at four different frequencies through the side, center and other side of the thumb.

In its more complex and preferable form, three-dimensional scans were produced at a single frequency. One side of the thumb was scanned to the other, for a total of 25-35 scans per person. Each single scale was two-dimensional, and when combined in a group, with location plotted on the Z axis, yielded a three-dimensional ultrasonic topography of the thumb, as shown in FIGS. 52 and 53. If the three-dimensional ultrasonic topography is extended to multiple frequencies, a four-dimensional plot results, with frequency on the W axis, as shown in FIG. 54. If waveform is varied, a five-dimensional plot results, as shown in FIG. 55.

In the preferred embodiment, medical frequencies in the low MHZ range (2.25 MHZ; 0.7 to 1.8 millimeters wavelength) were used and were able to detect all the detail necessary, and even actually more than necessary, to obtain a unique signature. This is why a two-dimensional scan at a single frequency is able to be obtained.

It should be appreciated that although the detection of induced current can be used for biometric recognition, the detection of induced current can be used for other purposes such as for diagnostic purposes including bone. In a normal bone, an induced current will flow through the bone since the bone is a conductor, as is well known in the art. See, "Radiofrequency Radiation Dosimetry Handbook", Fourth Edition, October, 1986; USAF School of Aerospace Medicine, Aerospace Medical Division (AFSC) Brooks Air Force Base, TX 78235-5301, incorporated by reference herein. See FIG. 59. However, when the bone has a fracture or break in it, the current will be interrupted due to the break or fracture and will prevent the current from flowing or substantially reduce the current from flowing that would have otherwise lowed if the bone did not have a break or fracture. As shown in FIG. 61, an apparatus for inducing an electric current in the bone, as described above, can have a galvanometer which reads the current flow which is induced in the bone, or in the case of a fracture or break, the lack thereof. FIG. 62 shows an apparatus to induce current in the bone with a galvanometer that shows expected and normal current flow through the bone.

The present invention pertains to an apparatus for identifying electric and/or magnetic properties of an individual living organism. The apparatus comprises a sensing mechanism for sensing the electric or magnetic properties. The apparatus comprises a mechanism for forming matrices corresponding to the organism having at least four-dimensions.

The present invention pertains to an apparatus for diagnosing a bone. The apparatus comprises a mechanism for inducing a current in the bone. The apparatus comprises a mechanism for detecting a fracture or break in the bone.

The present invention pertains to a method for diagnosing a bone. The method comprises the steps of inducing a current in the bone. Then there is the step of detecting the induced current in the bone. Next there is the step of detecting a fracture or break in the bone.

The present invention pertains to a method for sensing an induced current in an individual living organism. The method comprises the steps of inducing current in the organism. Then there is the step of detecting the current induced in the organism. Preferably, the detecting mechanism detects a characteristics of the organism associated with the induced current.

The present invention pertains to an apparatus for sensing an induced current in an individual living organism. The apparatus comprises a mechanism for inducing current in the organism. The apparatus comprises a mechanism for detecting the current induced in the organism. Preferably, the detecting mechanism detects a characteristics of the organism associated with the induced current.

The present invention pertains to an apparatus for sensing the electric and/or magnetic properties of an individual living organism. The apparatus comprises a mechanism for transmitting electric and/or magnetic energy into the organism. The apparatus comprises a mechanism for receiving the electric and/or magnetic energy after it has passed through the organism.

The present invention pertains to a method for using a computer. The method comprises the steps of sensing a non-visible attribute of an individual. Then there is the step of recognizing the individual. Next there is the step of accessing the computer by the individual.

The present invention pertains to a method for secure communication between an individual at a first location and a second location. The method comprises the steps of sensing a non-visible attribute of an individual. Then there is the step of recognizing the individual. Next there is the step of allowing thee individual to communicate with the second location.

The present invention pertains to an apparatus for sensing the electric and/or magnetic properties of an individual living organism. The apparatus comprises a mechanism for transmitting acoustic energy into the organism. The apparatus comprises a mechanism for receiving electric and/or magnetic energy generated in the organism due to the acoustic energy after is has interacted with the organism.

The present invention pertains to a method for sensing the electric and/or magnetic properties of an individual living organism. The method comprises the steps of transmitting acoustic energy into the organism. Then there is the step of receiving electric and/or magnetic energy generated in the organism, due to the acoustic energy after it has interacted with the organism.

Impedance and phase angle resonance frequencies can also be used for recognition. For instance, a person can grasp a transducer with the thumb and forefinger with the transducer providing a multifrequency scan point of the thumb and forefinger. Each organism for a given body segment has a unique impedance or phase angle resonance frequency that can be used to recognize the organism.

FIG. 67 shows the acoustic generation of direct current. An acoustic generating system provides energy to a piezoelectric material. The acoustic energy will travel through the body segments and a direct current will be generated. The direct current will be generated in the semi-conductor structures. FIG. 68 shows the acoustic generation of alternating current and magnetic fields. An alternating current will be generated in the semi-conductor structures whose natural oscillating frequency matches the acoustic frequency. This will in turn produce a magnetic field. FIG. 69 shows the detection of direct current or alternating current induced by acoustic energy. The acoustic generating system is connected to the piezoelectric material which results in acoustic energy traveling through the body segments. In turn direct current results which is detected by electric field detectors such as capacitors. FIG. 70 shows the detection of alternating current induced by acoustic energy. At a single frequency the locations are mapped out of the structures producing the alternating current, by detection with magnetic field detectors. FIG. 71 shows an acoustic wave induced by electric and/or magnetic energy. The acoustic analysis system receives induced acoustic waves from an acoustic transducer which results from electric/magnetic energy interacting with the body segments that have arisen from an electric and/or magnetic transmitter.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. A method for biometric recognition of an individual living organism comprising the steps of:

transmitting at least one of electric and magnetic energy into at least one body segment of the organism, whereby said body segment generates acoustic wave energy in response to reaction of said at least one of electric and magnetic energy with said body segment;

receiving and detecting said acoustic wave energy generated in the at least one body segment of the organism to form a detected acoustic biometric pattern; and comparing the detected acoustic biometric pattern to a reference biometric pattern.

2. The method of claim 1, wherein said at least one of electric and magnetic energy transmitted is selected from the group consisting of an electrical field and a magnetic field.

3. The method of claim 2, wherein said field oscillates.

4. The method of claim 3, wherein said oscillation is produced by a signal generator.

5. The method of claim 4, wherein said signal generator produces at least one signal having a waveform selected from the group consisting of sinusoidal, square wave, ramp and sawtooth.

6. The method of claim 4, wherein said at least one signal has a frequency in a range between about 40 Hz and about 400 MHz.

7. Apparatus for biometric recognition of an individual living organism, comprising:
   means for transmitting at least one of electric and magnetic energy into at least one body segment of the organism to interact with the at least one body segment, whereby at least one energy interacts with said body segment, thereby causing said body segment to generate acoustic wave energy;
   means for receiving and detecting the acoustic wave energy to generate a detected acoustic biometric pattern; and
   comparing the detected acoustic biometric pattern to a reference biometric pattern.

8. The apparatus of claim 7, wherein said means for detecting comprises an acoustic transducer and an acoustic analysis system.

9. The apparatus of claim 8, wherein at least a portion of said individual living organism is contacted to said detection means.

10. The apparatus of claim 7, wherein said means for transmitting comprises a frequency generator connected to and driving a transmitter of at least one field selected from the group consisting an electric field and a magnetic field.

11. The apparatus of claim 7, further comprising a test zone located between said transmitting and detecting means.

12. The apparatus of claim 11, wherein at least a portion of said at least one body segment of said individual living organism is placed into said test zone.

13. The apparatus of claim 12, wherein said body segment comprises a hand.

14. The apparatus of claim 12, wherein said body segment is directly contacted to said transmitting in cans.

15. The apparatus of claim 14, wherein said transmitting means comprises electrodes.

16. The apparatus of claim 12, wherein said body segment is not directly contacted to said transmitting means.

17. The apparatus of claim 7, wherein said body segment comprises bone.

18. Apparatus for biometric recognition of an individual living organism, comprising:
   a frequency generator, a transmitter of at least one of electric and magnetic energy, and a receiver/detector comprising, an acoustic transducer and an acoustic analysis system,
   wherein said transmitter and said acoustic transducer are disposed adjacent one another to define a test zone,
   further wherein said frequency generator is connected to said transmitter to control said transmitted energy,
   still further wherein said detector is connected to said receiver, and
   wherein said test zone is arranged to receive at least one body segment of said individual living organism, and further wherein said transmitter transmits at least one of electric and magnetic enemy into said test zone, whereby said at least one of electric and magnetic energy enters said body segment when said body segment is in said test zone, and further whereby at least a portion of said energy in said body segment interacts with said body segment to generate acoustic energy, and wherein at least a portion of said generated acoustic energy is received and detected by said acoustic transducer and by said acoustic analysis system.

19. A method for biometric recognition of an individual living organism, comprising the steps of:
   (a) transmitting at least one of electric and magnetic energy into at least one body segment of a testing organism whereby said body segment induces acoustic wave energy in response to interaction of said at least one of electric and magnetic energy with said body segment;
   (b) receiving and detecting said acoustic wave energy induced in the at least one body segment of the organism;
   (c) measuring at least one property of said received and detected acoustic wave energy;
   (d) changing at least one property of said electric and/or magnetic energy and repeating steps (a) through (c) to create a biometric pattern for said testing organism;
   (e) comparing said biometric pattern of said testing organism to a previously measured biometric pattern in a corresponding body segment of a known organism at the corresponding transmitted energy properties; and
   (f) making a determination whether the testing organism is the known organism.

20. Apparatus for biometric recognition of an individual, comprising:
   (a) means for transmitting at least one of electric and, magnetic energy into at least one body segment of the testing individual to interact with the at least one body segment, whereby at least one energy interacts with said body segment, thereby inducing said body segment to generate acoustic wave energy;
   (b) means for receiving and detecting the acoustic wave energy so generated;
   (c) means for measuring at least one property of said received and detected acoustic wave energy;
   means for altering at least one property of said electric and/or magnetic energy;
   means for storing information about said received and detected, acoustic wave energy corresponding to said initial and altered property of said electric and/or magnetic energy, thereby storing a biometric pattern of said testing individual; and
   means for comparing said stored biometric protein of said testing individual to a stored biometric pattern of a corresponding body segment of a known individual at the corresponding transmitted energy properties; and
   means for making a determination whether said testing individual is said known individual.

* * * * *